(12) United States Patent
Chandraratna et al.

(10) Patent No.: US 10,590,059 B2
(45) Date of Patent: Mar. 17, 2020

(54) COMPOUNDS AND SYNTHETIC METHODS FOR THE PREPARATION OF RETINOID X RECEPTOR-SPECIFIC RETINOIDS

(71) Applicant: Io Therapeutics, Inc., Santa Ana, CA (US)

(72) Inventors: Roshantha A. Chandraratna, San Juan Capistrano, CA (US); Vidyasagar Pradeep Vuligonda, Irvine, CA (US); Thomas Jacks, South Plainfield, NJ (US); Peter Wade, South Plainfield, NJ (US); Andrew Thompson, South Plainfield, NJ (US)

(73) Assignee: Io Therapeutics, Inc., Houston, TX (US)

( * ) Notice: Subject to any disclaimer, the term of this patent is extended or adjusted under 35 U.S.C. 154(b) by 0 days.

(21) Appl. No.: 16/194,141

(22) Filed: Nov. 16, 2018

(65) Prior Publication Data

US 2019/0152888 A1 May 23, 2019

Related U.S. Application Data

(60) Provisional application No. 62/671,137, filed on May 14, 2018, provisional application No. 62/588,163, filed on Nov. 17, 2017.

(51) Int. Cl.
| | |
|---|---|
| *C07C 57/50* | (2006.01) |
| *C07C 51/255* | (2006.01) |
| *C07C 29/44* | (2006.01) |
| *A61K 31/198* | (2006.01) |
| *C07C 33/38* | (2006.01) |
| *A61K 31/192* | (2006.01) |
| *C07C 33/36* | (2006.01) |

(52) U.S. Cl.
CPC ............ *C07C 57/50* (2013.01); *A61K 31/192* (2013.01); *A61K 31/198* (2013.01); *C07C 29/44* (2013.01); *C07C 33/36* (2013.01); *C07C 33/38* (2013.01); *C07C 51/255* (2013.01); *C07B 2200/07* (2013.01); *C07C 2601/02* (2017.05); *C07C 2602/10* (2017.05)

(58) Field of Classification Search
CPC ......... C07C 57/50; C07C 29/44; C07C 33/36; C07C 33/38; C07C 51/255; A61K 31/192; A61K 31/198
USPC ....................................................... 514/567
See application file for complete search history.

(56) References Cited

U.S. PATENT DOCUMENTS

| | | | | |
|---|---|---|---|---|
| 5,917,082 | A | * | 6/1999 | Vuligonda ............ A61K 31/20 560/100 |
| 6,048,873 | A | | 4/2000 | Vasudevan et al. |
| 6,720,423 | B2 | | 4/2004 | Vasudevan et al. |

| | | | |
|---|---|---|---|
| 2008/0300312 | A1 | 12/2008 | Chandraratna |
| 2013/0190395 | A1 | 7/2013 | Chandraratna et al. |
| 2015/0038585 | A1 | 2/2015 | Chandraratna et al. |
| 2017/0119714 | A1 | 5/2017 | Chandraratna |

FOREIGN PATENT DOCUMENTS

| | | |
|---|---|---|
| WO | 2017075607 | 5/2017 |
| WO | 2017075610 | 5/2017 |
| WO | 2017075612 | 5/2017 |
| WO | 2017155577 | 9/2017 |
| WO | 2017155578 | 9/2017 |

OTHER PUBLICATIONS

Vuligonda et al J. Med. Chem, 2001, 44, 2298-2303 (Year: 2001).*
Lebel et al Chem. Rev. 2003, 103, 977-1050 (Year: 2003).*
Masamune et al., Asymmetric Catalytic Cyclopropanation of Olefins: Bis-Oxazoline Copper Complexes, Tet. Letts. 31:6005-6008 (1990).
Masamune et al., Asymmetric Copper-Catalyzed Cycloporpanation of Trisubstituted and Unsymmetrical cis-1,2-Disubstituted Olefins: Modified Bis-Oxazoline Ligands, Tet. Letts. , 32:7373-7376 (1991).
Evans et al., Bis(oxazolines) as Chiral Ligands in Metal-Catalyzed Asymmetric Reacations. catalytic, Asymmetric Cyclopropanation of Olefins, JACS 113:726-728 (1991).
Callot & Metz, Rhodium(II)2,4,6-Triarylbenzoates: Improved Catalysts for the SYN Cyclopropanation of Z-Olifins, Tetrahedron 41(20):4495-4501 (1985).
Maxwell et al., Shape-Selective and Asymmetric Cyclopropanation of Alkenes Catalyzed by Rhodium Porphyrins, Organometallics 11:645-652 (1992).
Callot & Piechoeki, Cyclopropanation Using Rhodium(I-II)Porphyrins: Large CIS vs TRANS Selectivity,Tetrahedron Lett. 21:3489-3492 (1980).
Denmark et al., Catalytic Enatioselective Cyclopropanation with Bis(halomethyl)zinc Reagents. II. The Effect of Promoter Structure on Selectivity, Tetrahedron Letts. 36:2219-2222 (1995).
Denmark et al., New Vistas in Organoelement Chemistry, Pure Appl. Chem. 68:23-27 (1996).
Denmark & O'Connor, Catalytic, Enantioselective Cyclopropanation of Allylic Alcohols. Substrate Generality, J. Org. Chem. 62:584-594 (1997).
Takahashi et al., Novel retinoid X receptor antagonists: specific inhibition of retinoid synergism in RXR-RAR heterodimer actions. Journal of Medicinal Chemistry, vol. 45, No. 16, pp. 3327-3330 (2002).
Kagechika H et al., Synthetic retinoids: recent developments concerning structure and clinical utility. Journal of Medicinal Chemistry, vol. 48, No. 19: 5875-5883, (2005).
Kawata et al., RXR Partial Agonist Produced by Side Chain Repositioning of Alkoxy RXR Full Agonist Retains Antitype 2 Diabetes Activity without the Adverse Effects, J. Med. Chem. 58(2):912-926 (2015).
ISR and Written Opinion for PCT-US2018-061643.

(Continued)

*Primary Examiner* — Yevgeny Valenrod

(74) *Attorney, Agent, or Firm* — K&L Gates LLP; Louis C. Cullman; David Diamond

(57) ABSTRACT

Provided herein are compounds useful for the preparation of compounds that have retinoid-like biological activity. Also provided herein are processes for the preparation of compounds that have retinoid-like biological activity.

17 Claims, 6 Drawing Sheets

(56) References Cited

OTHER PUBLICATIONS

Vuligonda et al., Enatioselective Synthesis of Potent Retinoid X Receptor Ligands: Differential Biological Activities of Individual Antipodes, J. Med. Chem.44:2298-2303 (2001).
Radi et al., Discovery of Chiral Cyclopropyl Dihydro-Alkylthio-Benzyl-Oxopyrimidine (S-DABO) Derivatives as Potent HIV-1 Reverse Transcriptase Inhibitors with High Activity Against Clinically Relevant Mutants, J. Med. Chem. 52:840-851 (2009).
Zimmer et al., Enatioselective Synthesis of 1,2,3-Trisubstituted Cyclopropanes Using gem-Dizinc Reagents, JACS 131:15624-15626 (2009).
Charette et al., Catalytic Asymmetric Cyclopropanation of Allylic Alcohols with Titanium-TADDOLate:Scope of the Cyclopropanation Reaction, JACS 123:12168-12175 (2001).

* cited by examiner

COMPOUNDS AND SYNTHETIC METHODS FOR THE PREPARATION OF RETINOID X RECEPTOR-SPECIFIC RETINOIDS

RELATED APPLICATIONS

This application claims priority to U.S. Provisional Patent Application No. 62/671,137, filed on May 14, 2018, and U.S. Provisional Patent Application No. 62/588,163, filed on Nov. 17, 2017. The entire content of these applications is incorporated herein by reference.

STATEMENT REGARDING FEDERALLY SPONSORED RESEARCH OR DEVELOPMENT

This invention was made with government support under Grant Number 2R44AI112512-02A1 awarded by the National Institutes of Health. The government has certain rights in the invention.

BACKGROUND

Compounds which have retinoid-like biological activity have been described. Preclinical studies with rexinoids, which are agonists of retinoid X receptors (RXRs), suggest that selective activation of RXRs, which modulate functions associated with differentiation, inhibition of cell growth, apoptosis and metastasis, may be useful in treating a variety of diseases associated with the biochemical functions modulated by RXR.

SUMMARY

Provided herein are compounds useful for the preparation of compounds which have retinoid-like biological activity. In one embodiment, (2E,4E)-3-methyl-5-(1S,2S)-2-methyl-2-(5,5,8,8-tetramethyl-5,6,7,8-tetrahydronaphthalen-2-yl)cyclopropyl)penta-2,4-dienoic acid (Compound A) is described.

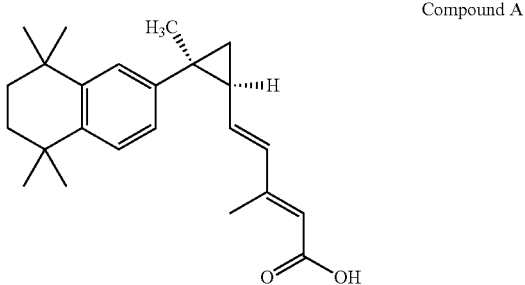 [SMILES: CC(/C=C/[C@@H]1C[C@]1(C)c1ccc2c(c1)C(C)(C)CCC2(C)C)=C\C(=O)O]

Compound A

Also provided herein are synthetic processes for the preparation of Compound A.

In one aspect, Compound 38 or Compound A is prepared by a process including one or more synthetic steps as shown in FIG. 2.

In another aspect, Compound 38 or Compound A is prepared by a process including one or more synthetic steps as shown in FIG. 3.

In still another aspect, Compound 38 or Compound A is prepared by a process including one or more synthetic steps as shown in FIG. 4.

In yet another aspect, Compound 38 or Compound A is prepared by a process including one or more synthetic steps as shown in FIG. 5.

In another aspect, Compound 38 or Compound A is prepared by a process including one or more synthetic steps as shown in FIG. 6.

DETAILED DESCRIPTION

Definitions

Figure 1:
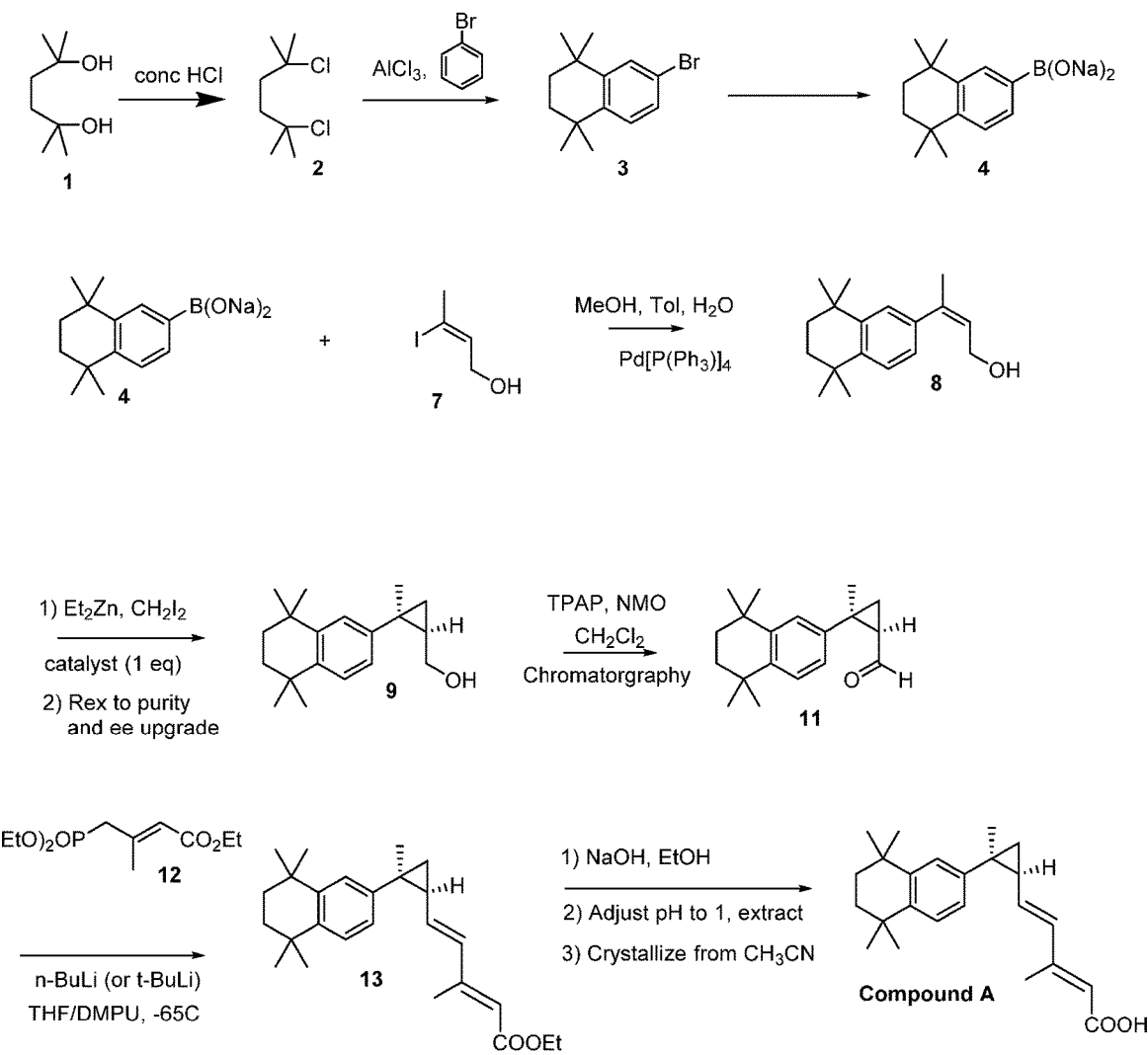
FIG. 1 shows a synthetic route for the preparation of Compound A.

"Administering" as used herein refers to administration of the compounds as needed to achieve the desired effect.

The term "alkyl" refers to a straight- or branched-chain saturated hydrocarbon having the number of carbon atoms designated. The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkenyl" refers to straight- or branched-chain unsaturated (e.g., at least one, at least two, at least three, or at least four unsaturations, i.e, carbon-carbon double-bonds) hydrocarbon moieties having the number of carbon atoms designated. The number of carbon atoms in an alkenyl substituent can be indicated by the prefix "$C_{x-y}$," where x is the minimum and y is the maximum number of carbon atoms in the substituent. Likewise, a $C_x$ chain means an alkenyl chain containing x carbon atoms.

The term "aryl" refers to mono- or poly-cyclic carbocyclic ring system comprising one or more aromatic ring systems having the number of carbon atoms designated. The number of carbon atoms in an aryl substituent can be indicated by the prefix "$C_{x-y}$," where x is the minimum and y is the maximum number of carbon atoms in the substituent. Likewise, a $C_x$ chain means an aryl chain containing x carbon atoms.

"Excipient" as used herein includes physiologically compatible additives useful in preparation of a pharmaceutical composition. Examples of pharmaceutically acceptable carriers and excipients can for example be found in Remington Pharmaceutical Science, 16$^{th}$ Ed.

"Halogen" or "halo" refers to fluoro, chloro, bromo or iodo moieties. Preferably, the halogen is fluoro, chloro, or bromo.

"Pharmaceutically acceptable carrier" means a carrier that is useful for the preparation of a pharmaceutical composition that is: generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

"Therapeutically effective amount" as used herein refers to a dosage of the compounds or compositions effective for influencing, reducing or inhibiting the activity of or preventing activation of a receptor as described herein. This term as used herein may also refer to an amount effective at bringing about a desired in vivo effect in an animal, preferably, a human, without substantial activation of an RAR.

Compounds (2E,4E)-3-methyl-5-((1S,2S)-2-methyl-2-(5,5,8,8-tetramethyl-5,6,7,8-tetrahydronaphthalen-2-yl)cyclopropyl) penta-2,4-dienoic acid is an RXR-specific retinoid (herein referred to as Compound A). Compound A has two chiral centers, and has an absolute stereochemistry of S,S. Synthetic processes for the preparation of Compound A, as well as uses of Compound A, have been previously described.

Although the literature provides processes for the preparation of Compound A, there is a continuing need for compounds and synthetic methods for the preparation of Compound A that result in an improvement of, at least, overall yield, enantiomeric excess, cost during synthesis, safety during synthesis, convenience during synthesis, or isolation of the compound.

Provided herein are compounds useful for the preparation of (2E,4E)-3-methyl-5-((1S,2S)-2-methyl-2-(5,5,8,8-tetramethyl-5,6,7,8-tetrahydronaphthalen-2-yl)cyclopropyl) penta-2,4-dienoic acid (Compound A).

Thus, in one aspect, provided herein is a compound, wherein the compound is:

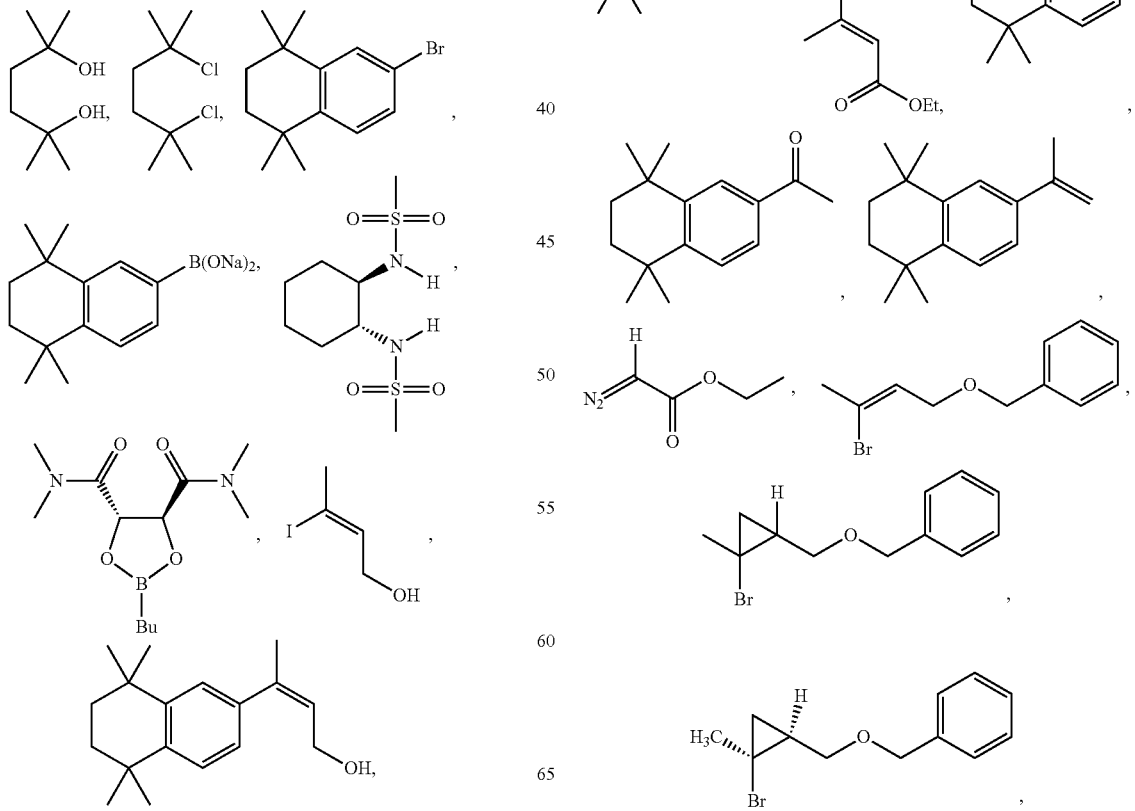

5
-continued

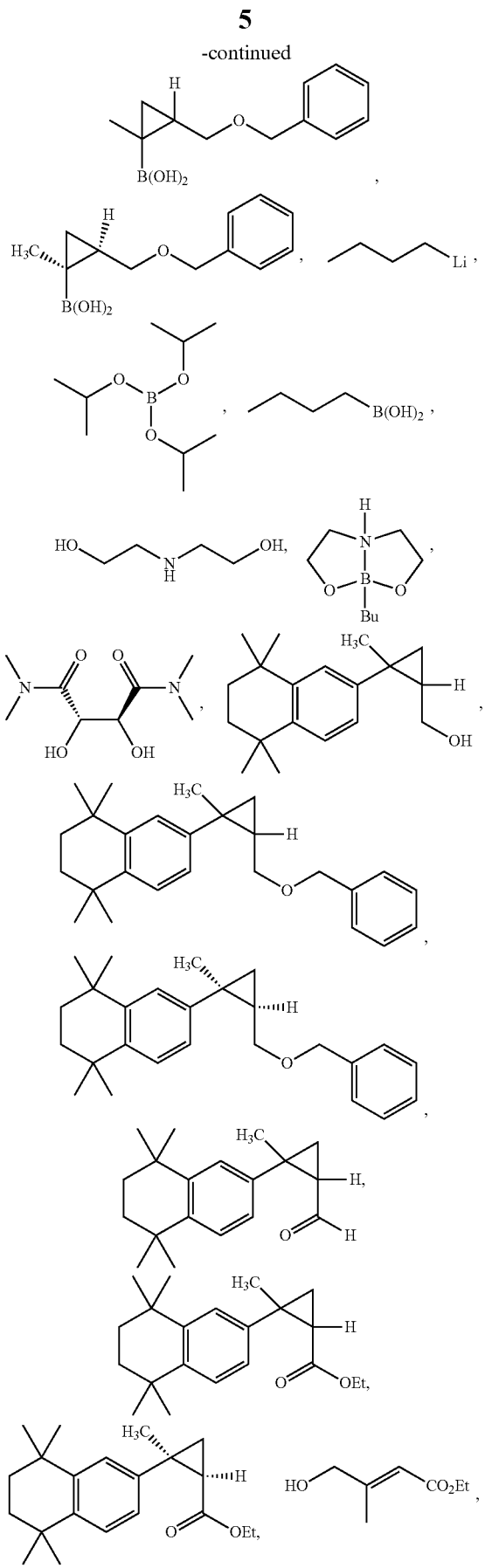

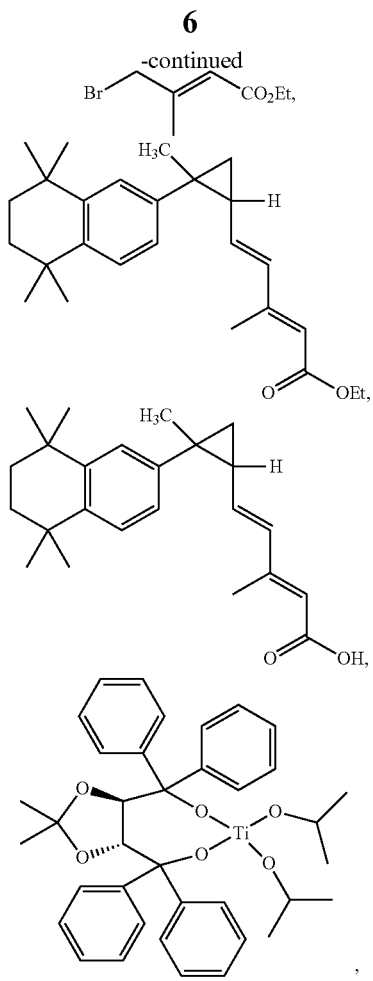

or a salt, hydrate, or solvate thereof.

In another aspect, provided herein is a compound of Formula I.

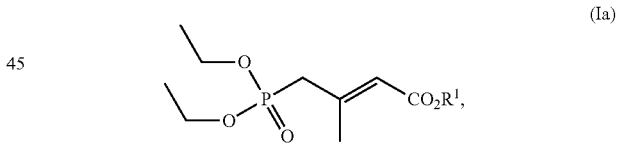

or a salt, hydrate, or solvate thereof.

wherein $R^1$ is $C_{1-20}$-alkyl; $C_{1-20}$-alkyl substituted with one or more substituents independently selected from —$NH_2$, —NH($C_{1-10}$-alkyl), —N($C_{1-10}$-alkyl)($C_{1-10}$-alkyl), —OH, halogen, —$C_{1-10}$-alkyl, —$C_{1-10}$-haloalkyl, —O—($C_{1-10}$-alkyl), or —O—($C_{1-10}$-haloalkyl); $C_{1-20}$-alkenyl; $C_{1-20}$-alkenyl substituted with one or more substituents independently selected from —$NH_2$, —NH($C_{1-10}$-alkyl), —N($C_{1-10}$-alkyl)($C_{1-10}$-alkyl), —OH, halogen, —$C_{1-10}$-alkyl, —$C_{1-10}$-haloalkyl, —O—($C_{1-10}$-alkyl), or —O—($O_{1-10}$-haloalkyl); $C_{6-14}$-aryl; or $C_{6-14}$-aryl substituted with one or more substituents independently selected from —$NH_2$, —NH($C_{1-10}$-alkyl), —N($C_{1-10}$-alkyl)($C_{1-10}$-alkyl), —OH, halogen, —$C_{1-10}$-alkyl, —$C_{1-10}$-haloalkyl, —O—($C_{1-10}$-alkyl), or —O—($C_{1-10}$-haloalkyl).

In another aspect, provided herein is a compound of Formula I:

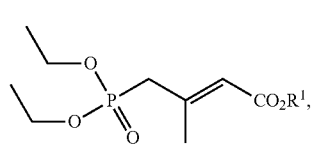
(I)

or a salt, hydrate, or solvate thereof, wherein $R^1$ is $C_{4-20}$-alkyl, $C_{1-20}$-alkenyl, or $C_{8-16}$-aryl.

In another aspect, provided herein is a compound of Formula

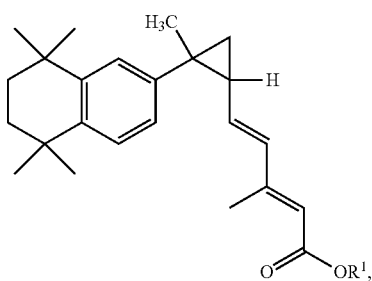
(II)

or a salt, hydrate, or solvate thereof, wherein $R^1$ is $C_{4-20}$-alkyl, $C_{1-20}$-alkenyl, or $C_{8-16}$-aryl.

In another aspect, provided herein is a compound of Formula III:

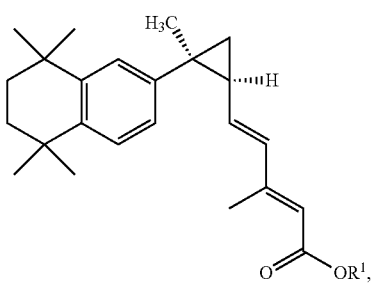
(IIIa)

or a salt, hydrate, or solvate thereof, wherein $R^1$ is $C_{1-20}$-alkyl; $C_{4-20}$-alkyl substituted with one or more substituents independently selected from —OH, halogen, —$C_{1-10}$-alkyl, —$C_{1-10}$-haloalkyl, —O—($C_{1-10}$-alkyl), or —O—($C_{1-10}$-haloalkyl); $C_{1-20}$-alkenyl; $C_{1-20}$-alkenyl substituted with one or more substituents independently selected from —OH, halogen, —$C_{1-10}$-alkyl, —$C_{1-10}$-haloalkyl, —$C_{1-10}$-haloalkyl, —O—($C_{1-10}$-alkyl), or —O—($C_{1-10}$-haloalkyl); $C_{6-14}$-aryl; or $C_{6-14}$-aryl substituted with one or more substituents independently selected from —OH, halogen, —$C_{1-10}$-alkyl, —$C_{1-10}$-haloalkyl, —O—($C_{1-10}$-alkyl), or —O—($C_{1-10}$-haloalkyl).

In another aspect, provided herein is a compound of Formula III:

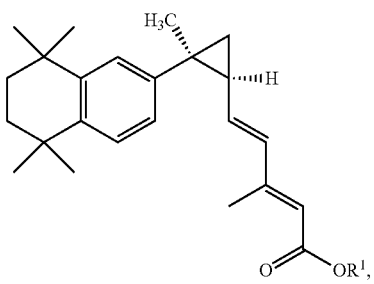
(III)

or a salt, hydrate, or solvate thereof, wherein $R^1$ is $C_{4-20}$-alkyl, $C_{1-20}$-alkenyl, or $C_{6-16}$-aryl.

In some embodiments of the Formulae provided herein, $R^1$ is $C_{4-10}$-alkyl, $C_{1-20}$-alkenyl, or $C_{6-14}$-aryl. In some embodiments, $R^1$ is $C_{4-10}$-alkyl, $C_{1-10}$-alkenyl, or $C_{6-14}$-aryl. In some embodiments, $R^1$ is $C_{1-20}$-alkenyl, or phenyl. In some embodiments, $R^1$ is $C_{1-10}$-alkenyl, or phenyl. In some embodiments, $R^1$ is $C_{4-20}$-alkyl. In some embodiments, $R^1$ is $C_{4-10}$-alkyl. In some embodiments, $R^1$ is $C_{4-8}$-alkyl. In some embodiments, $R^1$ is methyl. In some embodiments, $R^1$ is ethyl. In some embodiments, $R^1$ is propyl. In some embodiments, $R^1$ is $C_{1-20}$-alkenyl. In some embodiments, $R^1$ is $C_{1-10}$-alkenyl. In some embodiments, $R^1$ is $C_{1-6}$alkenyl. In some embodiments, $R^1$ is $C_{6-16}$-aryl. In some embodiments, $R^1$ is $C_{6-14}$-aryl. In some embodiments, $R^1$ is $C_{6-10}$-aryl. In some embodiments, $R^1$ is phenyl.

In another aspect, provided herein is a compound of Formula IV:

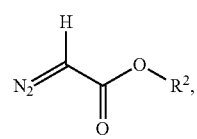
(IV)

or a salt, hydrate, or solvate thereof, wherein $R^2$ is $C_{1-20}$-alkyl, $C_{1-20}$-alkenyl, or $C_{8-16}$-aryl.

In another aspect, provided herein is a compound of Formula V:

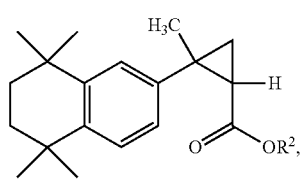
(V)

or a salt, hydrate, or solvate thereof, wherein $R^2$ is $C_{1-20}$-alkyl, $C_{1-20}$-alkenyl, or $C_{6-16}$-aryl.

In another aspect, provided herein is a compound of Formula VI:

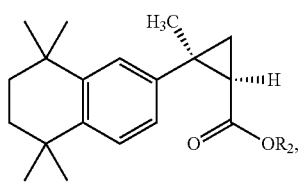

(VI)

or a salt, hydrate, or solvate thereof, wherein $R^2$ is $C_{1-20}$-alkyl, $C_{1-20}$-alkenyl, or $C_{6-16}$-aryl.

In some embodiments of the Formulae provided herein, $R^2$ is $C_{1-10}$-alkyl, $C_{1-10}$-alkenyl, or $C_{6-14}$-aryl. In some embodiments, $R^2$ is $C_{1-20}$-alkenyl, or $C_{6-14}$-aryl. In some embodiments, $R^2$ is $C_{1-10}$-alkenyl, or $C_{6-14}$-aryl. In some embodiments, $R^2$ is $C_{1-20}$-alkyl. In some embodiments, $R^2$ is $C_{1-10}$-alkyl. In some embodiments, $R^2$ is $C_{1-8}$-alkyl. In some embodiments, $R^2$ is $C_{1-4}$-alkyl. In some embodiments, $R^2$ is $C_{4-10}$-alkyl. In some embodiments, $R^2$ is ethyl. In some embodiments, $R^2$ is $C_{1-20}$-alkenyl. In some embodiments, $R^2$ is $C_{1-10}$-alkenyl. In some embodiments, $R^2$ is $C_{1-8}$-alkenyl. In some embodiments, $R^2$ is $C_{8-14}$-aryl. In some embodiments, $R^2$ is $C_{6-10}$-aryl. In some embodiments, $R^2$ is phenyl.

In another aspect, provided herein is a compound of Formula VII:

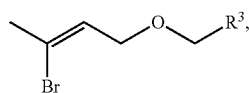

(VII)

or a salt, hydrate, or solvate thereof, wherein $R^3$ is aryl.

In another aspect, provided herein is a compound of Formula VIII:

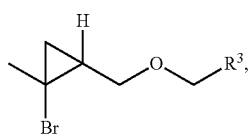

(VIIIa)

or a salt, hydrate, or solvate thereof, wherein $R^3$ is aryl, or aryl substituted with one or more substituents independently selected from —OH, halogen, —$C_{1-10}$-alkyl, —$C_{1-10}$-haloalkyl, or —O—($C_{1-10}$-alkyl), In another aspect, provided herein is a compound of Formula VIII:

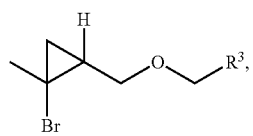

(VIII)

or a salt, hydrate, or solvate thereof, wherein $R^3$ is aryl.

In another aspect, provided herein is a compound of Formula IX:

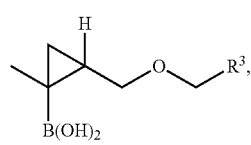

(IXa)

or a salt, hydrate, or solvate thereof, wherein $R^3$ is aryl, or aryl substituted with one or more substituents independently selected from —OH, halogen, —$C_{1-13}$-alkyl, —$C_{1-10}$-haloalkyl, or —O—($C_{1-10}$-alkyl).

In another aspect, provided herein is a compound of Formula IX:

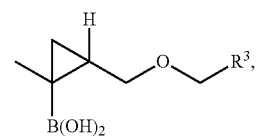

(IX)

or a salt, hydrate, or solvate thereof, wherein $R^3$ is aryl.

In another aspect, provided herein is a compound of Formula X:

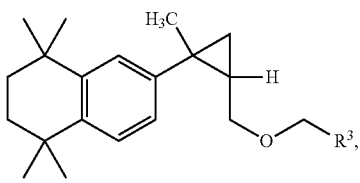

(Xa)

or a salt, hydrate, or solvate thereof, wherein $R^3$ is aryl, wherein $R^3$ is aryl, or aryl substituted with one or more substituents independently selected from —OH, halogen, —$C_{1-10}$-alkyl, —$C_{1-10}$-haloalkyl, or —O—($C_{1-13}$-alkyl).

In another aspect, provided herein is a compound of Formula X:

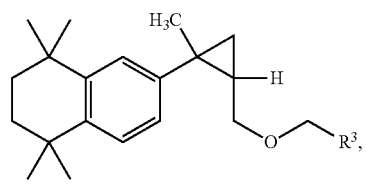

(X)

or a salt, hydrate, or solvate thereof, wherein $R^3$ is aryl.

In some embodiments, $R^3$ is $C_{6-14}$-aryl. In some embodiments, $R^3$ is $C_{6-14}$-aryl. In some embodiments, $R^3$ is $C_{14}$-aryl. In some embodiments, $R^3$ is $C_{10}$-aryl. In some embodiments, $R^3$ is phenyl.

In some embodiments, the compound is:

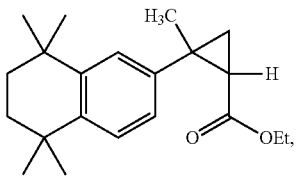 [SMILES: CCOC(=O)C1CC1(C)c1ccc2c(c1)C(C)(C)CCC2(C)C]

or a salt, hydrate, or solvate thereof.
In some embodiments, the compound is:

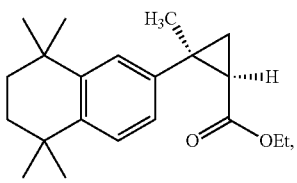 [SMILES: CCOC(=O)[C@@H]1C[C@]1(C)c1ccc2c(c1)C(C)(C)CCC2(C)C]

or a salt, hydrate, or solvate thereof.
In some embodiments, the compound is:

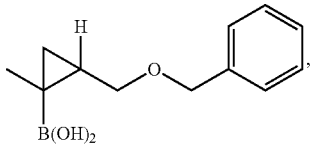 [SMILES: CC1(B(O)O)CC1COCc1ccccc1]

or a salt, hydrate, or solvate thereof.
In some embodiments, the compound is:

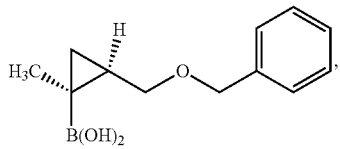 [SMILES: C[C@]1(B(O)O)C[C@H]1COCc1ccccc1]

or a salt, hydrate, or solvate thereof.
In some embodiments, the compound is:

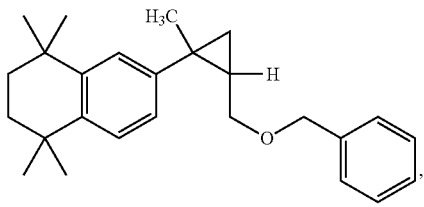 [SMILES: CC1(C)CCC(C)(C)c2cc(C3(C)CC3COCc3ccccc3)ccc21]

or a salt, hydrate, or solvate thereof.

In some embodiments, the compound is:

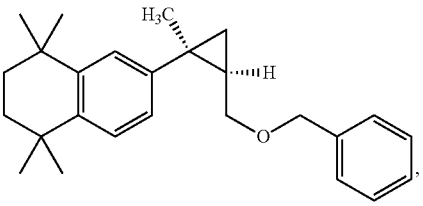 [SMILES: CC1(C)CCC(C)(C)c2cc([C@@]3(C)C[C@H]3COCc3ccccc3)ccc21]

or a salt, hydrate, or solvate thereof.
In some embodiments, the compound is Formula (XIa), (XIa)

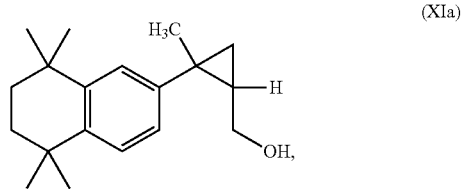 [SMILES: CC1(C)CCC(C)(C)c2cc(C3(C)CC3CO)ccc21]

or a hydrate or a solvate thereof,
wherein the compound has an enantiomeric excess of a compound of Formula (XI), (XI)

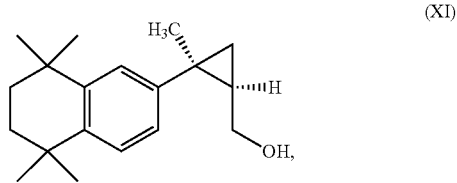 [SMILES: CC1(C)CCC(C)(C)c2cc([C@@]3(C)C[C@H]3CO)ccc21]

or a hydrate or a solvate thereof,
of at least about 80.0%.
In some embodiments, the compound is Compound 38, Compound 38

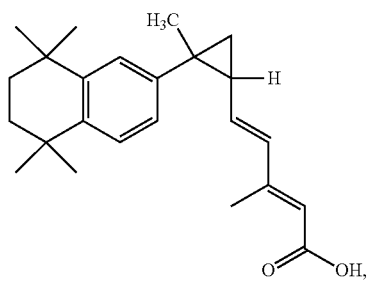

or a pharmaceutically acceptable salt thereof, wherein:

Compound 38 has an enantiomeric excess of Compound A,

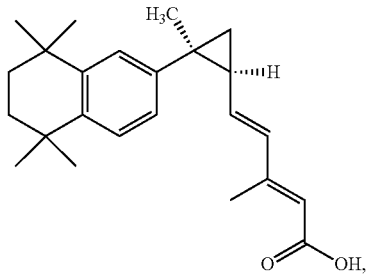

Compound A of least about 98.0%; and the compound is prepared by a synthetic process, and the synthetic process includes a process of preparing an intermediate compound, wherein the intermediate compound is Formula (XIa),

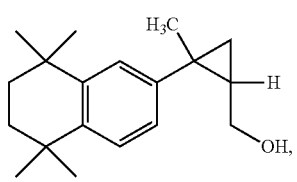

(XIa)

or a hydrate or a solvate thereof, wherein the intermediate compound has an enantiomeric excess of a compound of Formula (XI),

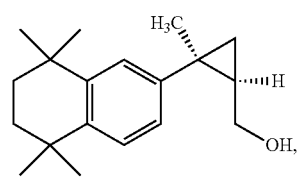

(XI)

or a hydrate or a solvate thereof,
of at least about 80.0%

In some embodiments, the enantiomeric excess is at least about 98.0%.

In some embodiments, the process of preparing the intermediate compound (e.g., Formula (XIa)), comprises:

contacting a compound of Formula (XII),

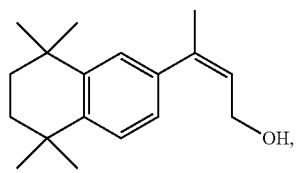

(XII)

or a solvate thereof, with $CH_2I_2$, $Et_2Zn$, $ZnI_2$, and

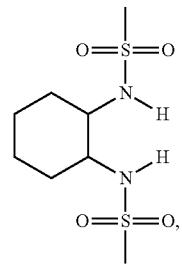

or a solvate thereof, such that the intermediate compound is formed.

In some embodiments, the

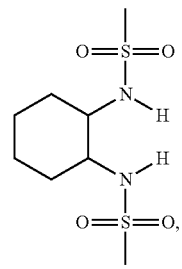

or a solvate thereof, is

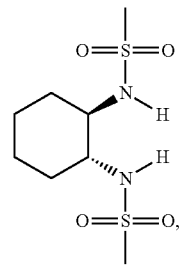

or a solvate thereof.

In some embodiments, the process of preparing the intermediate compound (e.g., Formula (XIa)), comprises:

(i) contacting a compound of Formula (XII),

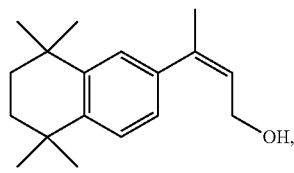

(XII)

or a solvate thereof, with a compound of Formula (XIII),

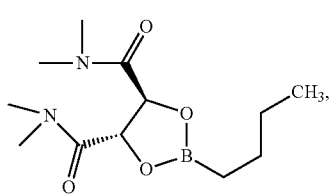
(XIII)

or a solvate thereof,
in a solution in the presence of CH$_2$I$_2$ and Et$_2$Zn to form a reaction product of the compound of Formula (XII), or a solvate thereof; and (ii) subsequently, contacting reaction product of the compound of Formula (XII), or a solvate thereof, of step (i) with H$_2$O$_2$, such that the intermediate compound is prepared.

In some embodiments, the process of preparing the intermediate compound (e.g., Formula (XIa)), comprises: contacting a compound of Formula (XII),

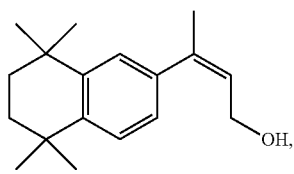
(XII)

or a solvate thereof,
with a compound of Formula (XIV) or its enantiomer,

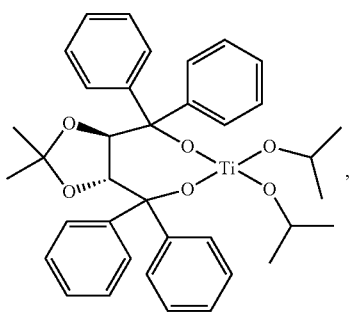
(XIV)

or a solvate thereof,
in the presence of CH$_2$I$_2$ and dialkylzinc such that the intermediate compound is prepared.

In some embodiments, the process of preparing the intermediate compound (e.g., Formula (XIa)), comprises: contacting a compound of Formula (XII),

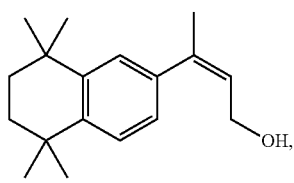
(XII)

or a solvate thereof, with a compound of Formula (XV) or its enantiomer,

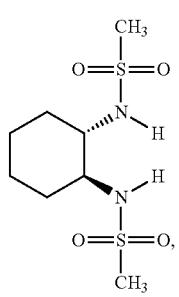
(XV)

or a solvate thereof,
in the presence of CH$_2$I$_2$ and Et$_2$Zn at about 0° C. such that the intermediate compound is prepared.

In some embodiments, the Formulae or compounds provided herein (e.g., Compounds 5, 6, 9, 10, 11, 13, 19, 20, 21, 22, 28, 29, 30, 31, 32, 33, 34, 37, 38, 39, or 40, or Formulae II, III, V, VI, VIII, IX, or X; e.g., Compounds 5, 6, 9, 10, 11, 13, 20, 22, 28, 31, 34, or 39, or Formulae III or VI) have an enantiomeric excess of at least 90%. In some embodiments, the Formulae or compounds provided herein have an enantiomeric excess of at least 95%. In some embodiments, the Formulae or compounds provided herein have an enantiomeric excess of at least 98%. In some embodiments, the Formulae or compounds provided herein have an enantiomeric excess of at least 99%. In some embodiments, the Formulae or compounds provided herein have an enantiomeric excess of at least 99.5%. In some embodiments, the Formulae or compounds provided herein have an enantiomeric excess of at least 99.9%. In some embodiments, the Formulae or compounds provided herein have an enantiomeric excess of at least 99.95%. In some embodiments, the Formulae or compounds provided herein have an enantiomeric excess of at least 99.99%. In some embodiments, the Formulae or compounds provided herein have an enantiomeric excess of about 90%, 91%, 92%, 93%, 94%, 95%, 96%, 97%, 98%, 99%, 99.2%, 99.4%, 99.5%, 99.6%, 99.8%, 99.9%, 99.95%, 99.99%, or a range bounded by any two of these values.

In some embodiments, Compound 38 (i.e., Compound A) has an enantiomeric excess of Compound A that essentially eliminates, or reduces to an undetectable level, an enantiomer of Compound A (e.g., Compound B).

In some embodiments, the compounds provided herein are provided as a suspension or solvent thereof.

In some embodiments, provided herein are compositions, comprising a compound provided herein.

In some embodiments, provided herein are pharmaceutical compositions, comprising a compound provided herein, and a pharmaceutically acceptable excipient or carrier.

Processes

Provided herein are processes for the preparation of (2E,4E)-3-methyl-5-((1S,2S)-2-methyl-2-(5,5,8,8-tetramethyl-5,6,7,8-tetrahydronaphthalen-2-yl)cyclopropyl)penta-2,4-dienoic acid (Compound A). Certain of the compounds useful in the processes provided herein are shown in Table 1. Certain of the compounds useful in the processes provided herein are provided herein as Formula I, Formula II, Formula III, Formula IV, Formula V, Formula VI, Formula VII, Formula VIII, Formula IX, or Formula X.

TABLE 1

| Compound | Structure name |
|---|---|
| Compound 1 | 2,5-dimethyl-hexane-2,5-diol |
| Compound 2 | 2,5-dichloro-2,5-dimethyl-hexane |
| Compound 3 | 6-bromo-1,1,4,4-tetramethyl-1,2,3,4-tetrahydronaphthalene |
| Compound 4 | sodium (5,5,8,8-tetramethyl-5,6,7,8-tetrahydronaphthalen-2-yl)boronate |
| Compound 5 | N,N'-((1S,2S)-cyclohexane-1,2-diyl)dimethanesulfonamide |
| Compound 6 | (4S,5S)-2-butyl-N4,N4,N5,N5-tetramethyl-1,3,2-dioxaborolane-4,5-dicarboxamide |
| Compound 7 | (Z)-3-iodobut-2-en-1-ol |
| Compound 8 | (Z)-3-(5,5,8,8-tetramethyl-5,6,7,8-tetrahydronaphthalen-2-yl)but-2-en-1-ol |
| Compound 9 | ((1R,2S)-2-methyl-2-(5,5,8,8-tetramethyl-5,6,7,8-tetrahydronaphthalen-2-yl)cyclopropyl)methanol |
| Compound 10 | (4S)-4-(tert-butyl)-2-(2-((S)-4-(tert-butyl)-4,5-dihydrooxazol-2-yl)propan-2-yl)oxazolidin-3-o trifluoromethanesulfonato copper(II) |

TABLE 1-continued

Compound 11

(1R,2S)-2-methyl-2-(5,5,8,8-
tetramethyl-5,6,7,8-
tetrahydronaphthalen-2-
yl)cyclopropanecarbaldehyde Compound 12

(E)-ethyl 4-(diethoxyphosphoryl)-3-
methylbut-2-enoate

Compound 13

(2E,4E)-ethyl 3-methyl-5-((1S,2S)-2-methyl-2-
(5,5,8,8-tetramethyl-5,6,7,8-
tetrahydronaphthalen-2-yl)cyclopropyl)penta-
2,4-dienoate Compound 14

1,1,4,4-
tetramethyl-1,2,3,4-
tetrahydronaphthalene

Compound 15

1-(5,5,8,8-tetramethyl-
5,6,7,8-
tetrahydronaphthalen-2-
yl)ethanone

Compound 16

1,1,4,4-tetramethyl-6-(prop-
1-en-2-yl)-1,2,3,4-
tetrahydronaphthalene

TABLE 1-continued

Compound 17 ethyl 2-diazoacetate

Compound 18

(Z)-(((3-bromobut-2-en-1-
yl)oxy)methyl)benzene

Compound 19

(((2-bromo-2-
methylcyclopropyl)methoxy)
methyl)benzene

Compound 20

((((1S,2S)-2-bromo-2-
methylcyclopropyl)methoxy)
methyl)benzene

Compound 21

(2-((benzyloxy)methyl)-1-
methylcyclopropyl)boronic acid

Compound 22

((1R,2R)-2-((benzyloxy)methyl)-1-
methylcyclopropyl)boronic acid

Compound 23 butyllithium

TABLE 1-continued

| Structure | Name | Compound |
|---|---|---|
| triisopropyl borate | triisopropyl borate | Compound 24 |
| butylboronic acid | butylboronic acid | Compound 25 |
| 2,2'-azanediyldiethanol | 2,2'-azanediyldiethanol | Compound 26 |
| 8-butylhexahydro-[1,3,2]oxazaborolo[2,3-b][1,3,2]oxazaborol-4-ium-8-uide | 8-butylhexahydro-[1,3,2]oxazaborolo[2,3-b][1,3,2]oxazaborol-4-ium-8-uide | Compound 27 |
| (2S,3S)-2,3-dihydroxy-N1,N1,N4,N4-tetramethylsuccinamide | (2S,3S)-2,3-dihydroxy-N1,N1,N4,N4-tetramethylsuccinamide | Compound 28 |
| (2-methyl-2-(5,5,8,8-tetramethyl-5,6,7,8-tetrahydronaphthalen-2-yl)cyclopropyl)methanol | (2-methyl-2-(5,5,8,8-tetramethyl-5,6,7,8-tetrahydronaphthalen-2-yl)cyclopropyl)methanol | Compound 29 |
| 6-(2-((benzyloxy)methyl)-1-methylcyclopropyl)-1,1,4,4-tetramethyl-1,2,3,4-tetrahydronaphthalene | 6-(2-((benzyloxy)methyl)-1-methylcyclopropyl)-1,1,4,4-tetramethyl-1,2,3,4-tetrahydronaphthalene | Compound 30 |
| 6-((1S,2R)-2-((benzyloxy)methyl)-1-methylcyclopropyl)-1,1,4,4-tetramethyl-1,2,3,4-tetrahydronaphthalene | 6-((1S,2R)-2-((benzyloxy)methyl)-1-methylcyclopropyl)-1,1,4,4-tetramethyl-1,2,3,4-tetrahydronaphthalene | Compound 31 |
| 2-methyl-2-(5,5,8,8-tetramethyl-5,6,7,8-tetrahydronaphthalen-2-yl)cyclopropanecarbaldehyde | 2-methyl-2-(5,5,8,8-tetramethyl-5,6,7,8-tetrahydronaphthalen-2-yl)cyclopropanecarbaldehyde | Compound 32 |
| ethyl 2-methyl-2-(5,5,8,8-tetramethyl-5,6,7,8-tetrahydronaphthalen-2-yl)cyclopropanecarboxylate | ethyl 2-methyl-2-(5,5,8,8-tetramethyl-5,6,7,8-tetrahydronaphthalen-2-yl)cyclopropanecarboxylate | Compound 33 |
| (1R,2S)-ethyl 2-methyl-2-(5,5,8,8-tetramethyl-5,6,7,8-tetrahydronaphthalen-2-yl)cyclopropanecarboxylate | (1R,2S)-ethyl 2-methyl-2-(5,5,8,8-tetramethyl-5,6,7,8-tetrahydronaphthalen-2-yl)cyclopropanecarboxylate | Compound 34 |
| (E)-ethyl 4-hydroxy-3-methylbut-2-enoate | (E)-ethyl 4-hydroxy-3-methylbut-2-enoate | Compound 35 |
| (E)-ethyl 4-bromo-3-methylbut-2-enoate | (E)-ethyl 4-bromo-3-methylbut-2-enoate | Compound 36 |

TABLE 1-continued

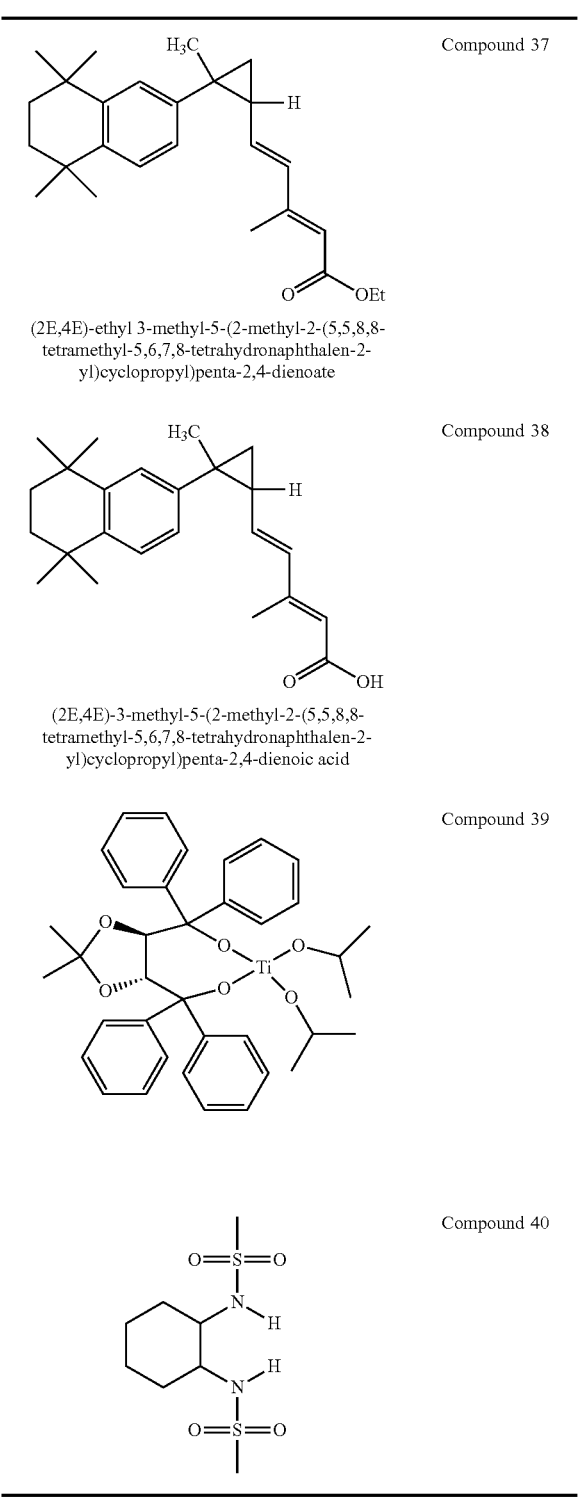

Compound 37

(2E,4E)-ethyl 3-methyl-5-(2-methyl-2-(5,5,8,8-tetramethyl-5,6,7,8-tetrahydronaphthalen-2-yl)cyclopropyl)penta-2,4-dienoate Compound 38

(2E,4E)-3-methyl-5-(2-methyl-2-(5,5,8,8-tetramethyl-5,6,7,8-tetrahydronaphthalen-2-yl)cyclopropyl)penta-2,4-dienoic acid Compound 39

Compound 40

It has been found that a catalytic amount of an enantioselectivity inducer (a compound provided herein that is a catalyst suitable for enantioselective inducement, e.g., Compound 39, Compound 40, or Compound 5), about 1.0 to about 1.2 equivalents of $CH_2I_2$, about 1.0 to about 1.2 equivalents of $Et_2Zn$, and about 1.0 equivalents of $ZnI_2$ react with Compound 8 to form Compound 9 according to the following scheme.

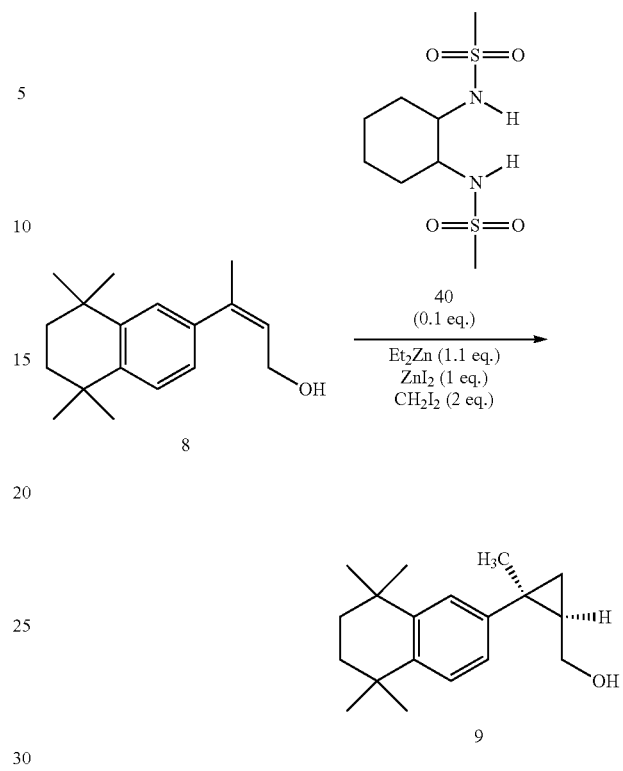

Thus, provided herein is a process of preparing Compound 9:

(Compound 9)

or a salt, hydrate, or solvate thereof, comprising:

contacting Compound 8, (Compound 8)

or a salt, hydrate, or solvate thereof, with $CH_2I_2$, $Et_2Zn$, $ZnI_2$, and a catalytic amount of Compound 40, (Compound 40)

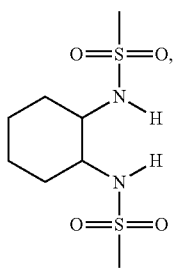

or a salt, hydrate, or solvate thereof,
such that Compound 9 or a salt, hydrate, or solvate thereof is formed.

In some embodiments, the molar ratio of Compound 8 to Compound 40 is about 1.0:0.1. In some embodiments, the molar ratio of Compound 8 to $CH_2I_2$ is about 1.0:(1.0-1.2). In some embodiments, the molar ratio of Compound 8 to $Et_2Zn$ is about 1.0:(1.0-1.2). In some embodiments, the molar ratio of Compound 8 to $ZnI_2$ is about 1.0:1.0.

Thus, also provided herein is a process of preparing Compound 9:

(Compound 9)

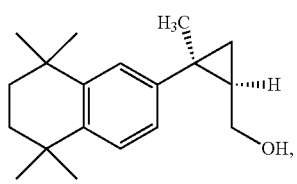

or a salt, hydrate, or solvate thereof,
comprising:
contacting Compound 8, (Compound 8)

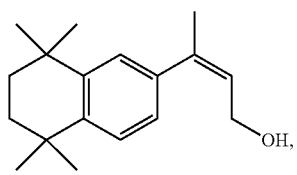

or a salt, hydrate, or solvate thereof,
with $CH_2I_2$, $Et_2Zn$, $ZnI_2$, and a catalytic amount of Compound 5, (Compound 5)

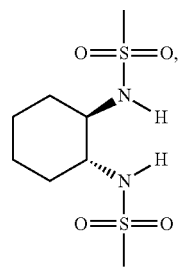 [SMILES: CS(=O)(=O)N[C@@H]1CCCC[C@H]1NS(C)(=O)=O]

or a salt, hydrate, or solvate thereof,
such that Compound 9 or a salt, hydrate, or solvate thereof is formed.

In some embodiments, the molar ratio of Compound 8 to Compound 5 is about 1.0:0.1. In some embodiments, the molar ratio of Compound 8 to $CH_2I_2$ is about 1.0:(1.0-1.2). In some embodiments, the molar ratio of Compound 8 to $Et_2Zn$ is about 1.0:(1.0-1.2). In some embodiments, the molar ratio of Compound 8 to $ZnI_2$ is about 1.0:1.0.

It has been found that a catalytic amount of an enantioselectivity inducer (a compound provided herein that is a catalyst suitable for enantioselective inducement, e.g., Compound 39), about 1.0 to about 1.2 equivalents of $CH_2I_2$, and about 1.0 to about 1.2 equivalents of $Et_2Zn$ react with Compound 8 to form Compound 9 according to the following scheme.

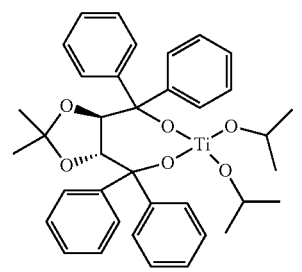

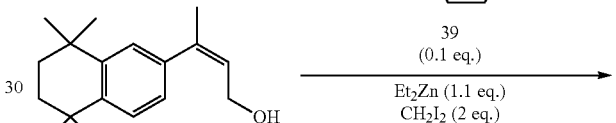

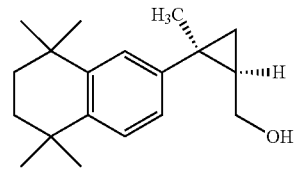

Thus, provided herein is a process of preparing Compound 9:

(Compound 9)

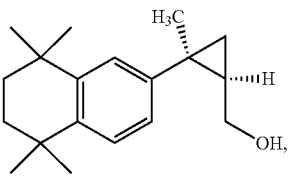

or a salt, hydrate, or solvate thereof,
comprising:
contacting Compound 8, (Compound 8)

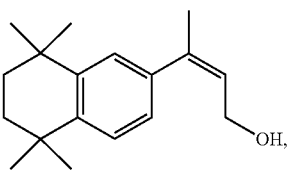

or a salt, hydrate, or solvate thereof, with CH₂I₂, Et₂Zn, and a catalytic amount of Compound 39,

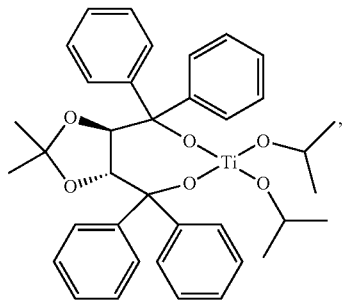
(Compound 39)

or a salt, hydrate, or solvate thereof, such that Compound 9 or a salt, hydrate, or solvate thereof is formed.

In some embodiments Compound 9 has an enantiomeric excess of at least about 80.0% (e.g., at least about 85%, 90%, 91%, 92%, 93%, 94%, 95%, 96%, 97%, 98%, or 99%). In some embodiments Compound 9 has an enantiomeric excess of at least about 98.0 (e.g., at least about 98.5%, 99.0%, 99.5%, 99.6%, 99.7%, 99.8%, 99.9%, 99.99%, or 99.999%).

In some embodiments, the molar ratio of Compound 8 to Compound 39 is about 1.0:0.1. In some embodiments, the molar ratio of Compound 8 to CH₂I₂ is about 1.0:(1.0-1.2). In some embodiments, the molar ratio of Compound 8 to Et₂Zn is about 1.0:(1.0-1.2).

It has been found that KOBu$^t$, which is cheaper and easier to handle than an alternative reagent n-BuLi, reacts in concert with Compound 12 to convert Compound 11 to Compound 13 according to the following scheme.

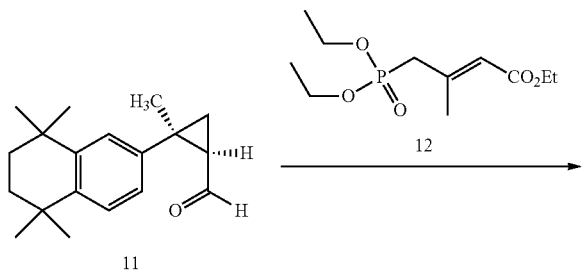

Thus, provided herein is a process of preparing Compound 13

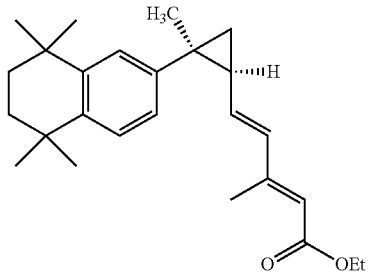
(Compound 13)

or a salt, hydrate, or solvate thereof, comprising:
contacting Compound 11

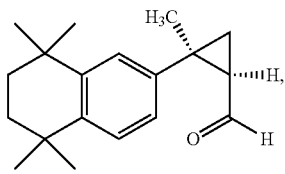
(Compound 11)

or a salt, hydrate, or solvate thereof,
with potassium t-butoxide and Compound 12,

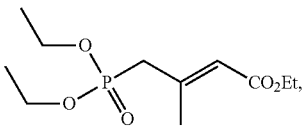
(Compound 12)

or a salt, hydrate, or solvate thereof,
such that Compound 13 or a salt, hydrate, or solvate thereof is formed.

In some embodiments Compound 13 has an enantiomeric excess of at least about 80.0% (e.g., at least about 85%, 90%, 91%, 92%, 93%, 94%, 95%, 96%, 97%, 98%, or 99%), In some embodiments Compound 13 has an enantiomeric excess of at least about 98.0 (e.g., at least about 98.5%, 99.0%, 99.5%, 99.6%, 99.7%, 99.8%, 99.9%, 99.99%, or 99.999%).

Compound 13 may then undergo hydrolysis upon contact with KOH to form Compound A.

Similarly, KOBu$^t$ reacts in concert with a compound of Formula I to convert Compound 11 to a compound of Formula III according to the following scheme.

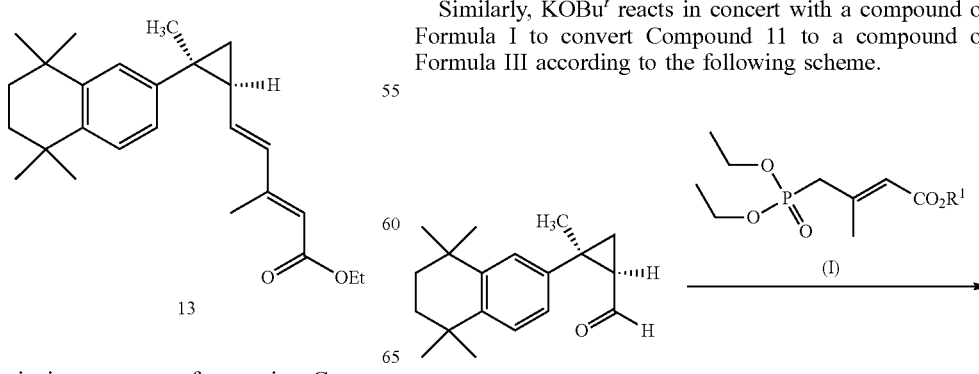

-continued

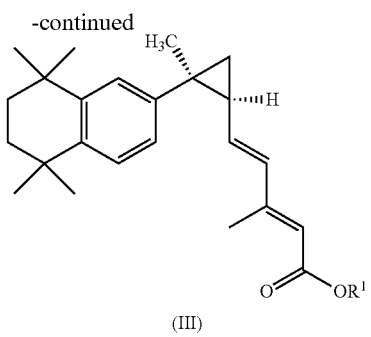

(III)

Thus, provided herein is a process of preparing a compound of Formula III:

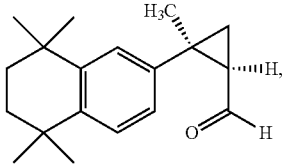
(III)

or a salt, hydrate, or solvate thereof,
comprising:
contacting Compound 11,

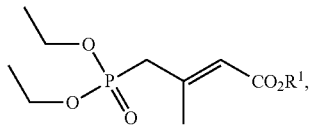
(Compound 11)

or a salt, hydrate, or solvate thereof,
with potassium t-butoxide and a compound of Formula I, (I)

or a salt, hydrate, or solvate thereof,
such that a compound of Formula III or a salt, hydrate, or solvate thereof is formed,
wherein $R^1$ is $C_{1-20}$-alkyl; $C_{1-20}$-alkyl substituted with one or more substituents independently selected from —$NH_2$, —$NH(C_{1-10}$-alkyl), —$N(C_{1-10}$-alkyl)($C_{1-10}$-alkyl), —OH, halogen, —$C_{1-10}$-alkyl, —$C_{1-10}$-haloalkyl, —O—($C_{1-10}$-alkyl), or —O—($C_{1-10}$-haloalkyl); $C_{1-20}$-alkenyl; $C_{1-20}$-alkenyl substituted with one or more substituents independently selected from —$NH_2$, —$NH(C_{1-10}$-alkyl), —$N(C_{1-10}$-alkyl)($C_{1-10}$-alkyl), —OH, halogen, —$C_{1-10}$-alkyl, —$C_{1-10}$-haloalkyl, —O—($C_{1-10}$-alkyl), or —O—($C_{1-10}$-haloalkyl); $C_{6-14}$-aryl; or $C_{6-14}$-aryl substituted with one or more substituents independently selected from —$NH_2$, —$NH(C_{1-10}$-alkyl), —$N(C_{1-10}$-alkyl)($C_{1-10}$-alkyl), —OH, halogen, —$C_{1-10}$-alkyl, —$C_{1-10}$-haloalkyl, —O—($C_{1-10}$-alkyl), or —O—($C_{1-10}$-haloalkyl).

In some embodiments, $R^1$ is $C_{4-20}$-alkyl; $C_{4-20}$-alkyl substituted with one or more substituents independently selected from —$NH_2$, —$NH(C_{1-10}$-alkyl), —$N(C_{1-10}$-alkyl)($C_{1-10}$-alkyl), —OH, halogen, —$C_{1-10}$-alkyl, —$C_{1-10}$-haloalkyl, —O—($C_{1-10}$-alkyl), or —O—($C_{1-10}$-haloalkyl); $C_{1-20}$-alkenyl; $C_{1-20}$-alkenyl substituted with one or more substituents independently selected from —$NH_2$, —$NH(C_{1-10}$-alkyl), —$N(C_{1-10}$-alkyl)($C_{1-10}$-alkyl), —OH, halogen, —$C_{1-10}$-alkyl, —$C_{1-10}$-haloalkyl, —O—($C_{1-10}$-alkyl), or —O—($C_{1-10}$-haloalkyl); $C_{6-14}$-aryl; or $C_{6-14}$-aryl substituted with one or more substituents independently selected from —$NH_2$, —$NH(C_{1-10}$-alkyl), —$N(C_{1-10}$-alkyl)($C_{1-10}$-alkyl), —OH, halogen, —$C_{1-10}$-alkyl, —$C_{1-10}$-haloalkyl, —O—($C_{1-10}$-alkyl), or —O—($C_{1-10}$-haloalkyl).

In some embodiments, $R^1$ is $C_{4-20}$-alkyl; $C_{4-20}$-alkyl substituted with one or more substituents independently selected from —OH, halogen, —$C_{1-10}$-alkyl, —$C_{1-10}$-haloalkyl, —O—($O_{1-10}$-alkyl), or —O—($C_{1-10}$-haloalkyl); $C_{1-20}$-alkenyl; $C_{1-20}$-alkenyl substituted with one or more substituents independently selected from —OH, halogen, —$C_{1-10}$-alkyl, —$C_{1-10}$-haloalkyl, —O—($C_{1-10}$-alkyl), or —O—($C_{1-10}$-haloalkyl); $C_{6-14}$-aryl; or $C_{6-14}$-aryl substituted with one or more substituents independently selected from —OH, halogen, —$C_{1-10}$-alkyl, —$C_{1-10}$-haloalkyl, —O—($C_{1-10}$-alkyl), or —O—($C_{1-10}$-haloalkyl).

In some embodiments, $R^1$ is $C_{4-10}$-alkyl; $C_{4-10}$-alkyl substituted with one or more substituents independently selected from —$NH_2$, —$NH(C_{1-6}$-alkyl), —$N(C_{1-6}$-alkyl)($C_{1-6}$-alkyl), —OH, halogen, —$C_{1-3}$-alkyl, —$C_{1-3}$-haloalkyl, —O—($C_{1-3}$-alkyl), or —O—($C_{1-3}$-haloalkyl); $C_{1-10}$-alkenyl; $C_{1-10}$-alkenyl substituted with one or more substituents independently selected from —$NH_2$, —$NH(C_{1-6}$-alkyl), —$N(C_{1-6}$-alkyl)($C_{1-6}$-alkyl), —OH, halogen, —$C_{1-3}$-alkyl, —$C_{1-3}$-haloalkyl, —O—($C_{1-3}$-alkyl), or —O—($C_{1-3}$-haloalkyl); $C_{6-10}$-aryl; or $C_{6-10}$-aryl substituted with one or more substituents independently selected from —$NH_2$, —$NH(C_{1-6}$-alkyl), —$N(C_{1-6}$-alkyl)($C_{1-6}$-alkyl), —OH, halogen, —$C_{1-3}$-alkyl, —$C_{1-3}$-haloalkyl, —O—($C_{1-3}$-alkyl), or —O—($C_{1-3}$-haloalkyl).

In some embodiments, $R^1$ is $C_{4-10}$-alkyl; $C_{4-10}$-alkyl substituted with one or more substituents independently selected from —$NH_2$, —$NH(C_{1-3}$-alkyl), —$N(C_{1-3}$-alkyl)($C_{1-3}$-alkyl), —OH, halogen, —$C_{1-3}$-alkyl, —$C_{1-3}$-haloalkyl, —O—($C_{1-3}$-alkyl), or —O—($C_{1-3}$-haloalkyl); $C_{1-10}$-alkenyl; $C_{1-10}$-alkenyl substituted with one or more substituents independently selected from —$NH_2$, —$NH(C_{1-3}$-alkyl), —$N(C_{1-3}$-alkyl)($C_{1-3}$-alkyl), —OH, halogen, —$C_{1-3}$-alkyl, —$C_{1-3}$-haloalkyl, —O—($C_{1-3}$-alkyl), or —O—($C_{1-3}$-haloalkyl); $C_{6-10}$-aryl; or $C_{6-10}$-aryl substituted with one or more substituents independently selected from —$NH_2$, —$NH(C_{1-3}$-alkyl), —$N(C_{1-3}$-alkyl)($C_{1-3}$-alkyl), —OH, halogen, —$C_{1-3}$-alkyl, —$C_{1-3}$-haloalkyl, —O—($C_{1-3}$-alkyl), or —O—($C_{1-3}$-haloalkyl).

In some embodiments, $R^1$ is $C_{4-10}$-alkyl; $C_{4-10}$-alkyl substituted with one or more substituents independently selected from —OH, halogen, —$C_{1-3}$-alkyl, —$C_{1-3}$-haloalkyl, —O—($C_{1-3}$-alkyl), or —O—($C_{1-3}$-haloalkyl); $C_{1-10}$-alkenyl; $C_{1-10}$-alkenyl substituted with one or more substituents independently selected from —OH, halogen, —$C_{1-3}$-alkyl, —$C_{1-3}$-haloalkyl, —O—($C_{1-3}$-alkyl), or —O—($C_{1-3}$-haloalkyl); $C_{6-10}$-aryl; or $C_{6-10}$-aryl substituted with one or more substituents independently selected from —OH, halogen, —C$_{1-3}$-alkyl, —C$_{1-3}$-haloalkyl, —O—(C$_{1-3}$-alkyl), or —O—(C$_{1-3}$-haloalkyl).

In some embodiments, R$^1$ is C$_{4-10}$-alkyl; C$_{4-10}$-alkyl substituted with one or more substituents independently selected from F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$; C$_{1-10}$-alkenyl; C$_{1-10}$-alkenyl substituted with one or more substituents independently selected from F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$; C$_{6-10}$-aryl; or C$_{6-10}$-aryl substituted with one or more substituents independently selected from F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$.

In some embodiments, R$^1$ is C$_{4-6}$-alkyl; C$_{4-6}$-alkyl substituted with one or more substituents independently selected from —NH$_2$, —NH(C$_{1-3}$-alkyl), —N(C$_{1-3}$-alkyl)(C$_{1-3}$-alkyl), F, Cl, Br, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$; C$_{1-4}$-alkenyl; C$_{1-4}$-alkenyl substituted with one or more substituents independently selected from —NH$_2$, —NH(C$_{1-3}$-alkyl), —N(C$_{1-3}$-alkyl)(C$_{1-3}$-alkyl), F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$; phenyl; or phenyl substituted with one or more substituents independently selected from —NH$_2$, —NH(C$_{1-3}$-alkyl), —N(C$_{1-3}$-alkyl)(C$_{1-3}$-alkyl), F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$.

In some embodiments, R$^1$ is C$_{1-4}$-alkyl; or C$_{1-4}$-alkyl substituted with one or more substituents independently selected from —NH$_2$, —NH(C$_{1-3}$-alkyl), —N(C$_{1-3}$-alkyl)(C$_{1-3}$-alkyl), F, Cl, Br, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$.

In some embodiments, R$^1$ is C$_{1-4}$-alkenyl; or C$_{1-4}$-alkenyl substituted with one or more substituents independently selected from —NH$_2$, —NH(C$_{1-3}$-alkyl), —N(C$_{1-3}$-alkyl)(C$_{1-3}$-alkyl), F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$.

In some embodiments, R$^1$ is phenyl; or phenyl substituted with one or more substituents independently selected from —NH$_2$, —NH(C$_{1-3}$-alkyl), —N(C$_{1-3}$-alkyl)(C$_{1-3}$-alkyl), F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$.

In some embodiments, R$^1$ is C$_{4-6}$-alkyl; C$_{4-6}$-alkyl substituted with one or more substituents independently selected from F, Cl, Br, —CH$_2$F, —CHF$_2$, —CF$_3$, —CH$_2$Cl, —CHCl$_2$Cl$_2$, —CCl$_3$, —O-methyl, —O—CH$_2$F, —O—CHF$_2$, —O—CF$_3$, —O—CHCl$_2$, or —O—CCl$_2$; C$_{1-4}$-alkenyl; C$_{1-4}$-alkenyl substituted with one or more substituents independently selected from F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$; phenyl; or phenyl substituted with one or more substituents independently selected from F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$.

In some embodiments, R$^1$ is C$_{1-4}$-alkyl; or C$_{1-4}$-alkyl substituted with one or more substituents independently selected from F, Cl, Br, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$.

In some embodiments, R$^1$ is C$_{1-4}$-alkenyl; or C$_{1-4}$-alkenyl substituted with one or more substituents independently selected from F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$.

In some embodiments, R$^1$ is phenyl; or phenyl substituted with one or more substituents independently selected from F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —OCF$_3$, —O—CH$_2$Cl, —O—CHCl$_2$, or —O—CCl$_3$.

In some embodiments, R$^1$ is C$_{4-20}$-alkyl, C$_{1-20}$-alkenyl, or C$_{6-14}$-aryl.

In some embodiments, R$^1$ is C$_{1-20}$-alkenyl or C$_{6-14}$-aryl.
In some embodiments, R$^1$ is C$_{1-10}$-alkenyl or C$_{6-10}$-aryl.
In some embodiments, R$^1$ is C$_{1-10}$-alkenyl or phenyl.
In some embodiments, R$^1$ is C$_{1-10}$-alkyl.
In some embodiments, R$^1$ is C$_{1-6}$-alkyl.
In some embodiments, R$^1$ is methyl, ethyl, propyl, isopropyl, butyl, isobutyl, or tert-butyl.

In some embodiments the compound of Formula (III) has an enantiomeric excess of at least about 80.0% (e.g., at least about 85%, 90%, 91%, 92%, 93%, 94%, 95%, 96%, 97%, 98%, or 99%). In some embodiments the compound of Formula (III) has an enantiomeric excess of at least about 98.0% (e.g., at least about 98.5%, 99.0%, 99.5%, 99.6%, 99.7%, 99.8%, 99.9%, 99.99%, or 99.999%).

A compound of Formula III may then undergo hydrolysis upon contact with KOH to form Compound A.

In some embodiments Compound A has an enantiomeric excess of at least about 80.0% (e.g., at least about 85%, 90%, 91%, 92%, 93%, 94%, 95%, 96%, 97%, 98%, or 99%). In some embodiments Compound A has an enantiomeric excess of at least about 98.0% (e.g., at least about 98.5%, 99.0%, 99.5%, 99.6%, 99.7%, 99.8%, 99.9%, 99.99%, or 99.999%).

It has been found that contacting Compound 16 with Compound 17 and a catalyst produces Compound 33 as shown in the following scheme.

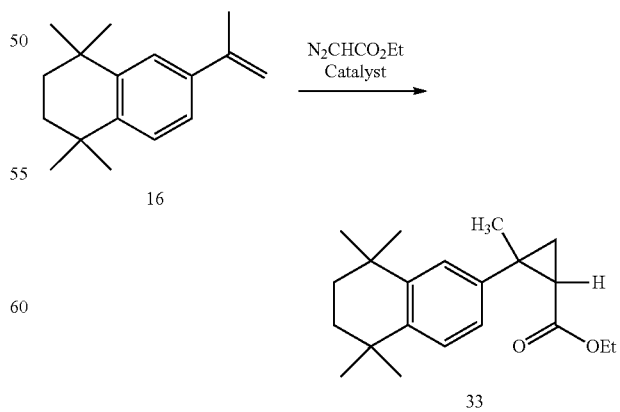

Thus, provided herein is a process of preparing Compound 33:

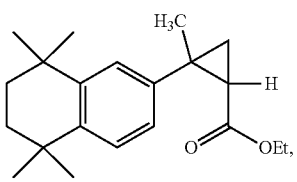

(Compound 33)

or a salt, hydrate, or solvate thereof, comprising:
contacting Compound 16,

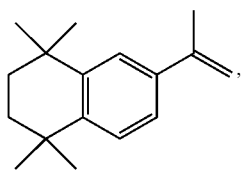

(Compound 16)

or a salt, hydrate, or solvate thereof, with a catalyst and Compound 17,

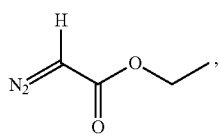

(Compound 17)

or a salt, hydrate, or solvate thereof, such that Compound 33 or a salt, hydrate, or solvate thereof is formed.

In some embodiments Compound 33 has an enantiomeric excess of at least about 80.0% (e.g., at least about 85%, 90%, 91%, 92%, 93%, 94%, 95%, 96%, 97%, 98%, or 99%). In some embodiments Compound 33 has an enantiomeric excess of at least about 98.0% (e.g., at least about 98.5%, 99.0%, 99.5%, 99.6%, 99.7%, 99.8%, 99.9%, 99.99%, or 99.999%).

It has been found that contacting Compound 19 with n-BuLi and B(OMe)$_3$ produces Compound 21 as shown in the following scheme.

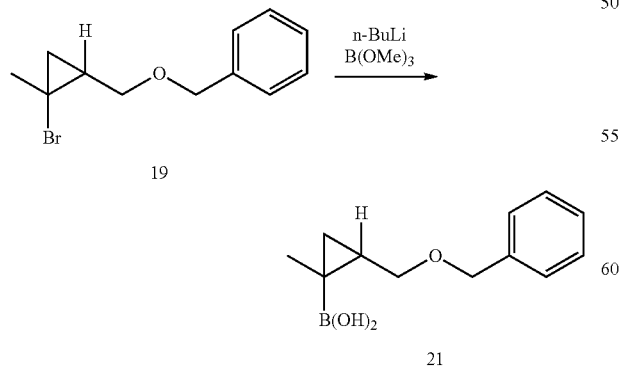

Thus, provided herein is a process of preparing Compound 21:

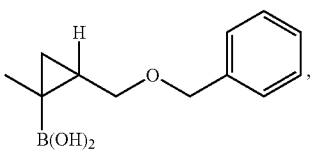

(Compound 21)

or a salt, hydrate, or solvate thereof, comprising:
contacting Compound 19,

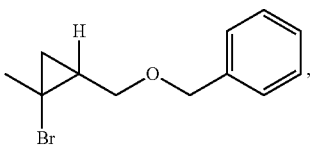

(Compound 19)

or a salt, hydrate, or solvate thereof,
with n-BuLi or t-BuLi, and B(OMe)$_3$,
such that Compound 21 or a salt, hydrate, or solvate thereof is formed.

In some embodiments Compound 21 has an enantiomeric excess of at least about 80.0% (e.g., at least about 85%, 90%, 91%, 92%, 93%, 94%, 95%, 96%, 97%, 98%, or 99%). In some embodiments Compound 21 has an enantiomeric excess of at least about 98.0% (e.g., at least about 98.5%, 99.0%, 99.5%, 99.6%, 99.7%, 99.8%, 99.9%, 99.99%, or 99.999%).

Similarly, contacting a compound of Formula VIII with n-BuLi and a B(OMe)$_3$ produces a compound Formula IX as shown in the following scheme,

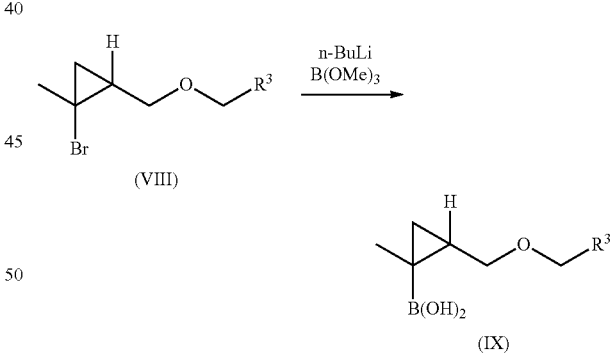

Thus, provided herein is a process of preparing a compound of Formula IX:

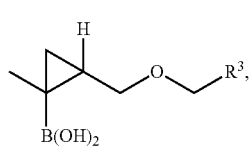

(IX)

or a salt, hydrate, or solvate thereof, comprising:

contacting a compound of Formula VIII,

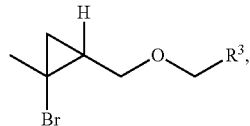
(VIII)

or a salt, hydrate, or solvate thereof,
with n-BuLi or t-BuLi, and B(OMe)$_3$,
such that a compound of Formula IX or a salt, hydrate, or solvate thereof is formed,
wherein R$^3$ is aryl, or aryl substituted with one or more substituents independently selected from —OH, halogen, —C$_{1-10}$-alkyl, —C$_{1-10}$-haloalkyl, or —O—(C$_{1-13}$-alkyl).

In some embodiments, R$^3$ is C$_{6-14}$-aryl, or C$_{6-14}$-aryl substituted with one or more substituents independently selected from —OH, halogen, —C$_{1-10}$-alkyl, —O—(C$_{1-10}$-alkyl), or —O—(C$_{1-10}$-haloalkyl).

In some embodiments, R$^3$ is phenyl, or phenyl substituted with one or more substituents independently selected from —OH, halogen, —C$_{1-10}$-alkyl, —C$_{1-10}$-haloalkyl, —O—(C$_{1-10}$-alkyl), or —O—(C$_{1-10}$-haloalkyl).

In some embodiments, R$^3$ is phenyl, or phenyl substituted with one or more substituents independently selected from —OH, halogen, —C$_{1-3}$-alkyl, —C$_{1-3}$-haloalkyl, —O—(C$_{1-3}$-alkyl), or —O—(C$_{1-3}$-haloalkyl).

In some embodiments, R$^3$ is phenyl, or phenyl substituted with one or more substituents independently selected from F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CH$_2$Cl, —O—CHCl$_2$, or —O—CCl$_3$, In some embodiments the compound of Formula (IX) has an enantiomeric excess of at least about 80.0% (e.g., at least about 85%, 90%, 91%, 92%, 93%, 94%, 95%, 96%, 97%, 98% or 99%). In some embodiments the compound of Formula (IX) has an enantiomeric excess of at least about 98.0% (e.g., at least about 98.5%, 99.0%, 99.5%, 99.6%, 99.7%, 99.8%, 99.9%, 99.99%, or 99.999%).

It has been found that contacting Compound 21 with Compound 3 and Pd$_{(0)}$ produces Compound 30 as shown in the following scheme.

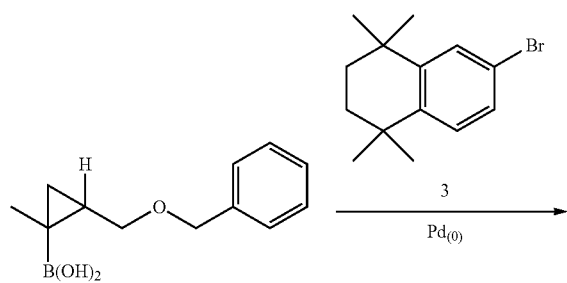

-continued

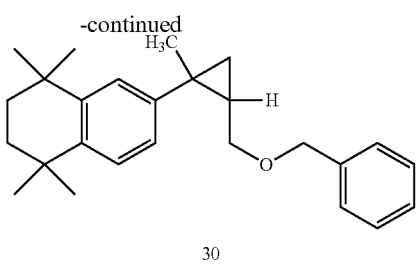
30

Thus, provided herein is a process of preparing Compound 30:

(Compound 30)

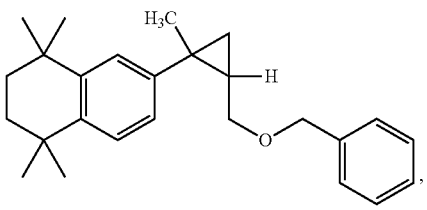

or a salt, hydrate, or solvate thereof,
comprising:
contacting Compound 21, (Compound 21)

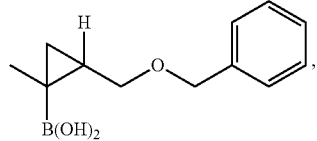

or a salt, hydrate, or solvate thereof,
with Pd$_{(0)}$ and Compound 3, (Compound 3)

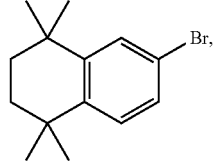

or a salt, hydrate, or solvate thereof,
such that Compound 30 or a salt, hydrate, or solvate thereof is formed, In some embodiments Compound 30 has an enantiomeric excess of at least about 80.0% (e.g., at least about 85%, 90%, 91%, 92%, 93%, 94%, 95%, 96%, 97%, 98%, or 99%). In some embodiments Compound 30 has an enantiomeric excess of at least about 98.0% (e.g., at least about 98.5%, 99.0%, 99.5%, 99.6%, 99.7%, 99.8%, 99.9%, 99.99%, or 99.999%).

Similarly, contacting a compound of Formula IX with Compound 3 and Pd$_{(0)}$ produces a compound of Formula X as shown in the following scheme.

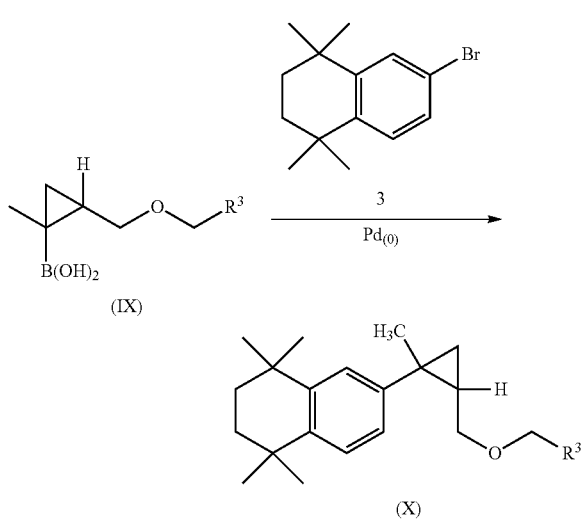

Thus, provided herein is a process of preparing a compound of Formula X

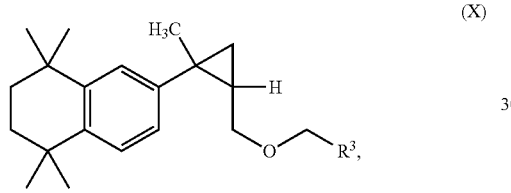

or a salt, hydrate, or solvate thereof,
comprising:
contacting a compound of Formula IX,

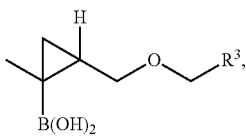

or a salt, hydrate, or solvate thereof,
with Pd$_{(0)}$ and Compound 3,

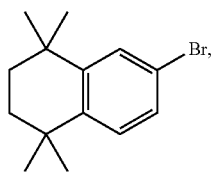

(Compound 3)

or a salt, hydrate, or solvate thereof,
such that a compound of Formula X or a salt, hydrate, or solvate thereof is formed,
wherein R$^3$ is aryl, or aryl substituted with one or more substituents independently selected from —OH, halogen, —C$_{1-10}$-alkyl, —C$_{1-10}$-haloalkyl, or —O—(C$_{1-10}$-alkyl).

In some embodiments, R$^3$ is C$_{6-14}$-aryl, or C$_{6-14}$-aryl substituted with one or more substituents independently selected from —OH, halogen, —C$_{1-10}$-alkyl, —C$_{1-10}$-haloalkyl, —O—(C$_{1-10}$-alkyl), or —O—(C$_{1-10}$-haloalkyl).

In some embodiments, R$^3$ is phenyl, or phenyl substituted with one or more substituents independently selected from —OH, halogen, —C$_{1-10}$-alkyl, —C$_{1-10}$-haloalkyl, —O—(C$_{1-10}$-alkyl), or —O—(C$_{1-10}$-haloalkyl).

In some embodiments, R$^3$ is phenyl, or phenyl substituted with one or more substituents independently selected from —OH, halogen, —C$_{1-3}$-alkyl, —C$_{1-3}$-haloalkyl, —O—(C$_{1-3}$-alkyl), or —O—(C$_{1-3}$-haloalkyl).

In some embodiments, R$^3$ is phenyl, or phenyl substituted with one or more substituents independently selected from F, Cl, Br, methyl, —CH$_2$F, —CHF$_2$, —CF$_3$, —CH$_2$Cl, —CHCl$_2$, —CCl$_3$, —O-methyl, —O—CH$_2$F, —O—CHF$_2$, —O—CF$_3$, —O—CH$_2$Cl, —O—CHCl$_2$, or —O—CCl$_3$.

In some embodiments the compound of Formula (X) has an enantiomeric excess of at least about 80.0% (e.g., at least about 85%, 90%, 91%, 92%, 93%, 94%, 95%, 96%, 97%, 98%, or 99%). In some embodiments the compound of Formula (X) has an enantiomeric excess of at least about 98.0% (e.g., at least about 98.5%, 99.0%, 99.5%, 99.6%, 99.7%, 99.8%, 99.9%, 99.99%, or 99.999%).

It has been found that contacting compound 8 with compound 6 produces compound 9 as shown in the following scheme.

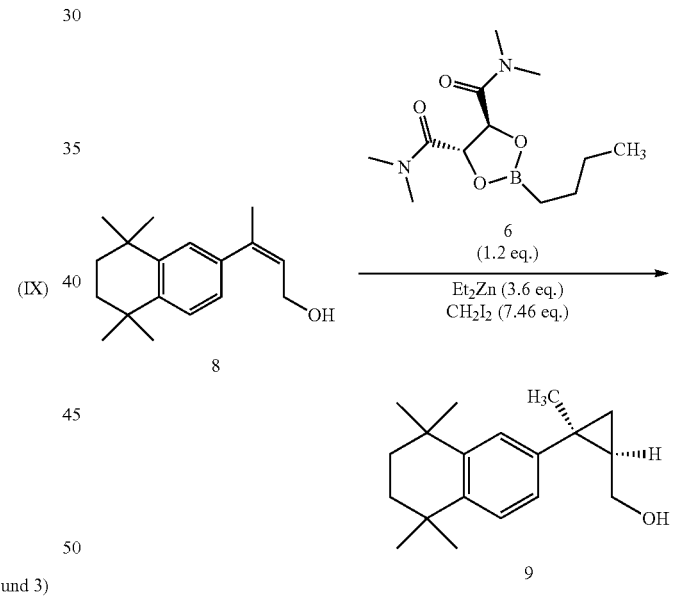

Thus, provided herein are processes of preparing a compound of Formula (XI):

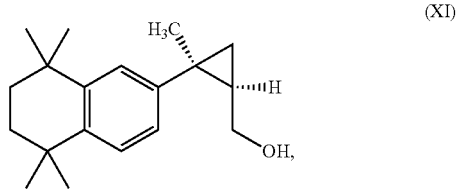 [SMILES: CC1(C)CCC(C)(C)c2cc([C@@]3(C)C[C@H]3CO)ccc21]

or a solvate thereof, comprising:

(i) contacting a compound of Formula (XII),

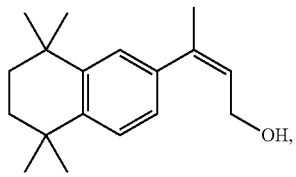
(XII)

or a solvate thereof,
with a compound of Formula (XIII),

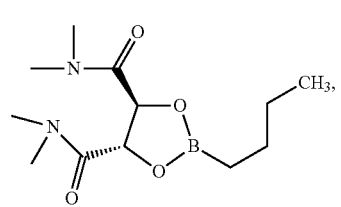
(XIII)

or a solvate thereof,
in a solution in the presence of CH$_2$I$_2$ and Et$_2$Zn; and (ii) subsequently, contacting the solution of step (i) with H$_2$O$_2$, such that a compound of Formula (XI) or a solvate thereof is prepared, wherein the compound of Formula (XI) has an enantiomeric excess of at least 80.0%.

It has been found that contacting compound 8 with a catalytic amount of compound 41 (or its enantiomer) produces compound 9 as shown in the following scheme.

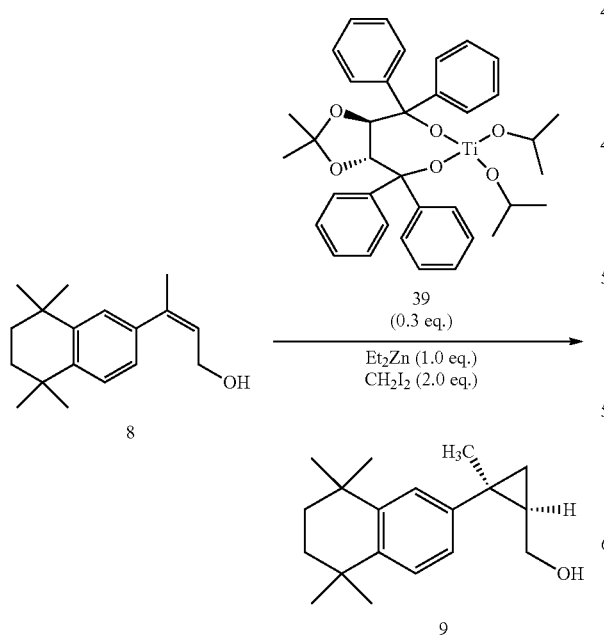

Thus, provided herein are processes of preparing a compound of formula (XI):

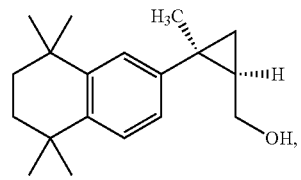
(XI)

or a solvate thereof,
comprising:
contacting a compound of Formula (XII),

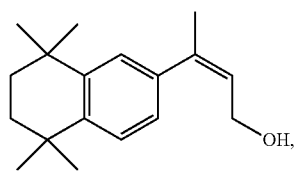
(XII)

or a solvate thereof,
with a compound of Formula (XIV) or its enantiomer,

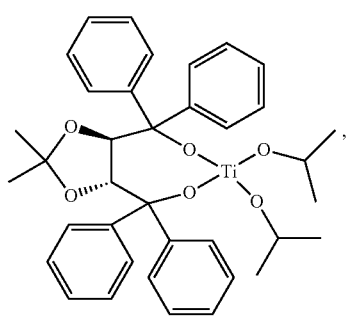
(XIV)

or a solvate thereof,
in the presence of CH$_2$I$_2$ and dialkylzinc such that a compound of Formula (XI) or a solvate thereof is prepared.

In some embodiments, the dialkylzinc is ZnEt$_2$.

In some embodiments the compound of Formula (XI) has an enantiomeric excess of at least about 80.0% (e.g., at least about 85%, 90%, 91%, 92%, 93%, 94%, 95%, 96%, 97%, 98% or 99%). In some embodiments the compound of Formula (XI) has an enantiomeric excess of at least about 98.0% (e.g., at least about 98.5%, 99.0%, 99.5%, 99.6%, 99.7%, 99.8%, 99.9%, 99.99%, or 99.999%).

It has been found that contacting compound 8 with a catalytic amount of compound 40 (or its enantiomer) produces compound 9 as shown in the following scheme.

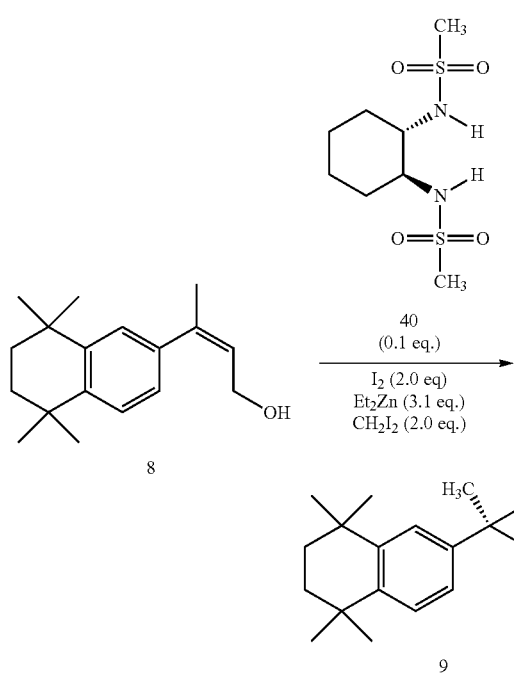

Thus, provided herein are processes of preparing a compound of Formula (XI):

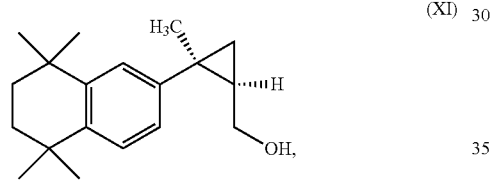
(XI)

or a solvate thereof,
comprising:
contacting a compound of Formula (XII),

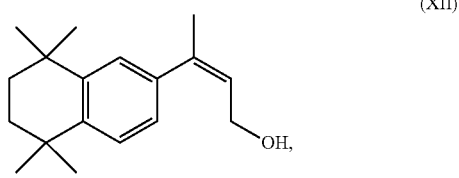
(XII)

or a solvate thereof,
with a compound of Formula (XV) or its enantiomer,

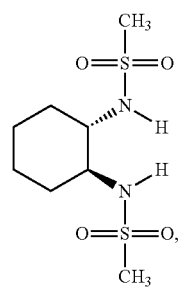
(XV)

or a solvate thereof, in the presence of CH$_2$I$_2$ at about 0° C. such that the compound of Formula (XI) or a solvate thereof is prepared.

In some embodiments, the molar ratio of Formula (XII) to Formula (XV) is about 1.0:0.05 to about 1.0:0.3, In some embodiments, the molar ratio of Formula (XII) to Formula (XV) is about 1.0:0.1.

It has been found that contacting compound 4 with compound 7 produces compound 8 as shown in the following scheme.

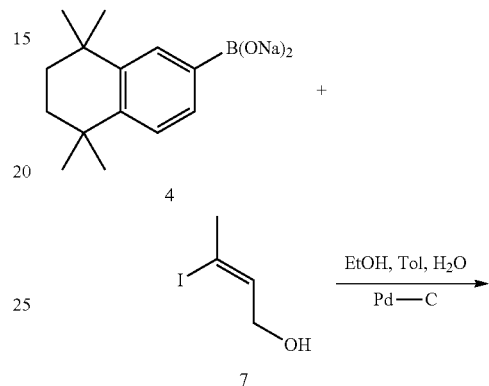

Thus, provided herein are processes of preparing a compound of Formula (XII):

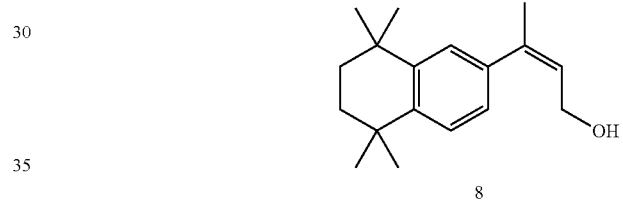
(XII)

or a solvate thereof,
comprising:
contacting a compound of Formula (XVI),

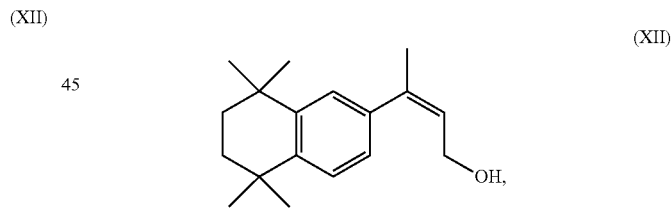
(XVI)

or a solvate thereof, with a compound of Formula (XVII),

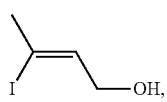

(XVII)

or a solvate thereof,
in the presence of Pd/C and a base, such that the compound of Formula (XII) or a solvate thereof is prepared.
In some embodiments the base is $K_2CO_3$.

It has been found that contacting compound 16 with compound 10 produces compound 33 as shown in the following scheme.

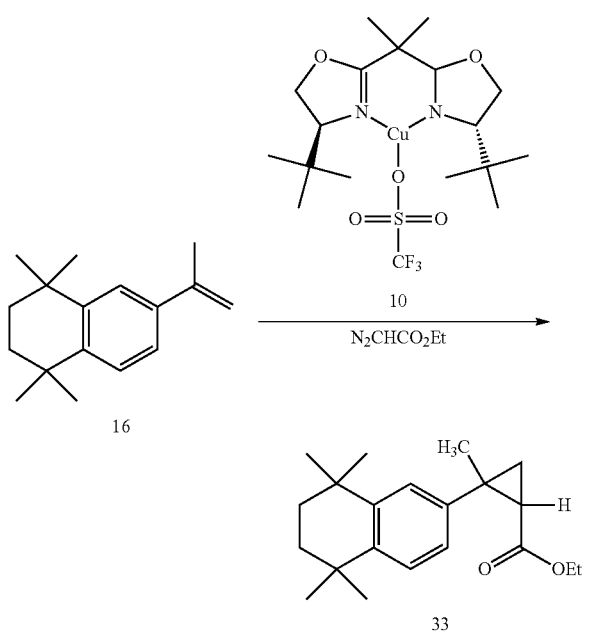

Thus, provided herein are processes of preparing a compound of Formula (XVII):

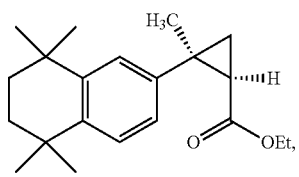

(XVII)

or a solvate thereof,
comprising:
contacting a compound of Formula (XVIII),

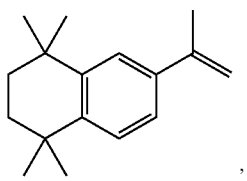

(XVIII)

or a solvate thereof, with a compound of Formula (XIX) or its enantiomer,

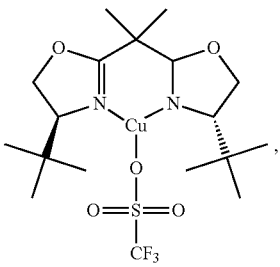

(XIX)

or a solvate thereof,
in the presence of $N_2CH_2CO_2Et$ such that a compound of Formula (XVII) or a solvate thereof is prepared.

In some embodiments the compound of Formula (XVII) has an enantiomeric excess of at least about 80.0% (e.g., at least about 85%, 90%, 91%, 92%, 93%, 94%, 95%, 96%, 97%, 98%, or 99%). In some embodiments the compound of Formula (XVII) has an enantiomeric excess of at least about 98.0% (e.g., at least about 98.5%, 99.0%, 99.5%, 99.6%, 99.7%, 99.8%, 99.9%, 99.99%, or 99.999%).

In some embodiments, the processes provided herein are performed in the presence of a solvent or a combination of solvents (e.g., at least one solvent, e.g., one solvent, two solvents, three solvents, or four or more solvents).

In some embodiments, the solvent is a non-polar solvent or a polar non-aqueous solvent, an aqueous solvent, or a combination thereof.

In some embodiments, the solvent is acetonitrile, chloroform, dichloromethane, 1,3-dimethyl-3,4,5,6-tetrahydro-2(1H)-pyrimidinone, ethanol, ethyl ether, $H^+_{(aq)}$ (e.g., $HCl_{(aq)}$, $HBr_{(aq)}$, $HOOAc_{(aq)}$, etc.), heptane, hexane, isopropanol, methanol, methyl tert-butyl ether, 2-methyl-tetrahydrofuran, $(OH)^-_{(aq)}$ (e.g., $NaOH_{(aq)}$, $KOH_{(aq)}$, $NH_3 \cdot H_2O_{(aq)}$, etc.), tetrahydrofuran, toluene, water.

In some embodiments, the processes provided herein are performed in the presence of sieves as a dehydrating agent (e.g., 4 Å sieves or 3 Å sieves).

In some embodiments, Compound A is prepared as shown in FIG. 1. As may be apparent to one of skill in the art, certain of the Formulae provided herein may be substituted for certain of the intermediate compounds of the scheme shown in FIG. 1 in order to arrive at alternative processes of preparing Compound A.

Figure 2:
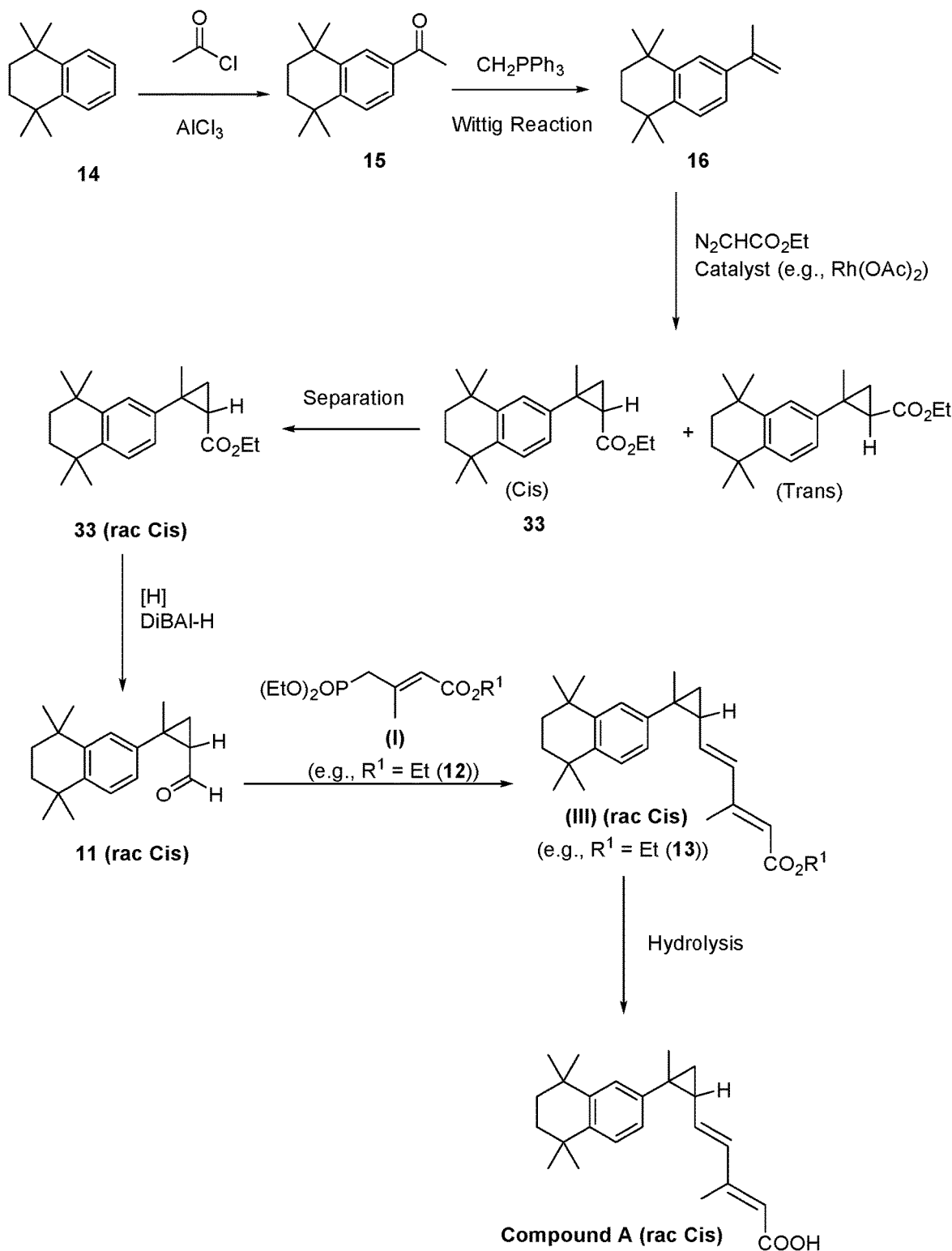
FIG. 2 shows a synthetic route for the preparation of Compound A.

In some embodiments, Compound A is prepared as shown in FIG. 2. As may be apparent to one of skill in the art, certain of the Formulae provided herein may be substituted for certain of the intermediate compounds of the scheme shown in FIG. 2 in order to arrive at alternative processes of preparing Compound A.

Figure 3:
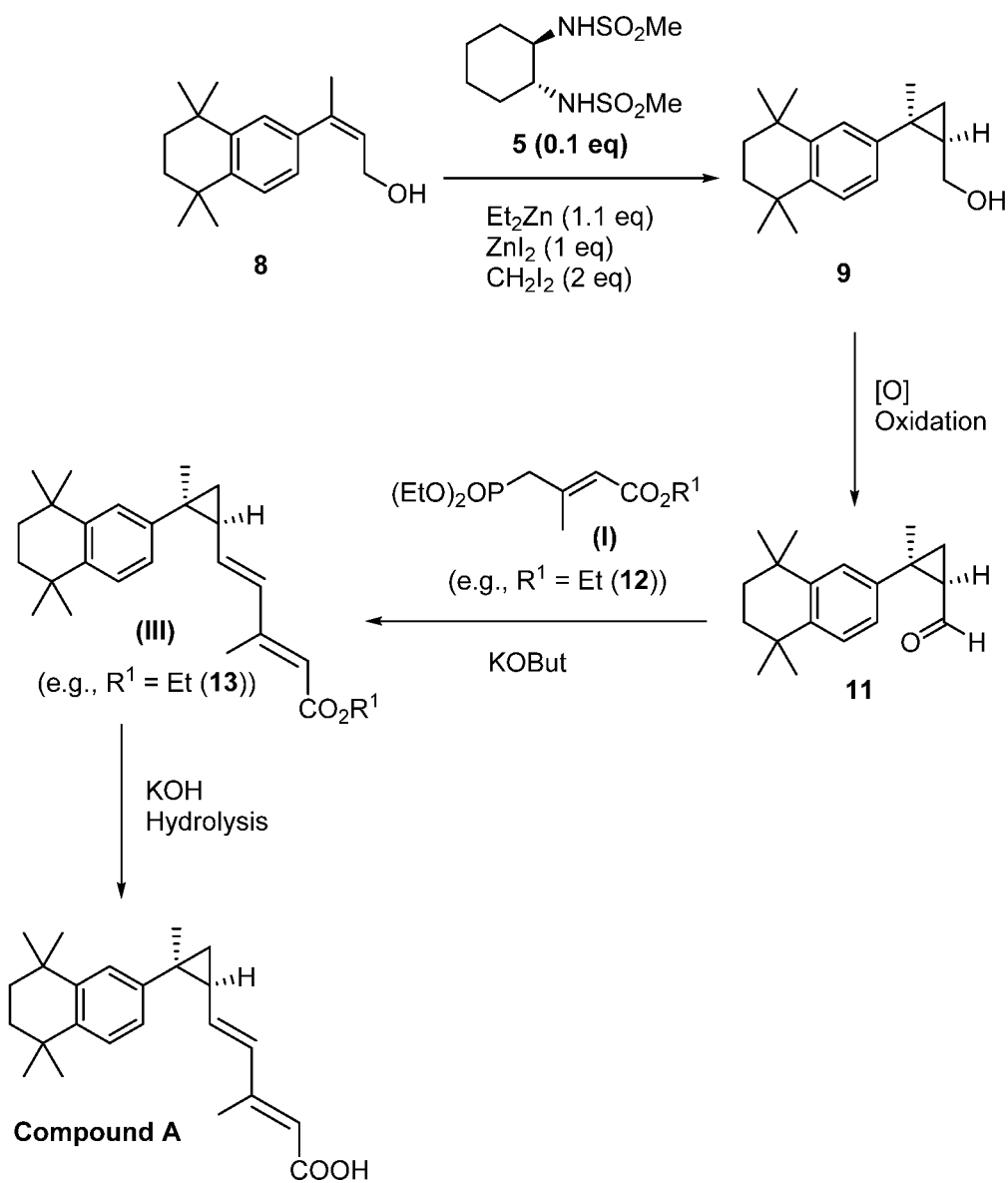
FIG. 3 shows a synthetic route for the preparation of Compound A.

In some embodiments, Compound A is prepared as shown in FIG. 3. As may be apparent to one of skill in the art, certain of the Formulae provided herein may be substituted for certain of the intermediate compounds of the scheme shown in FIG. 3 in order to arrive at alternative processes of preparing Compound A.

Figure 4:
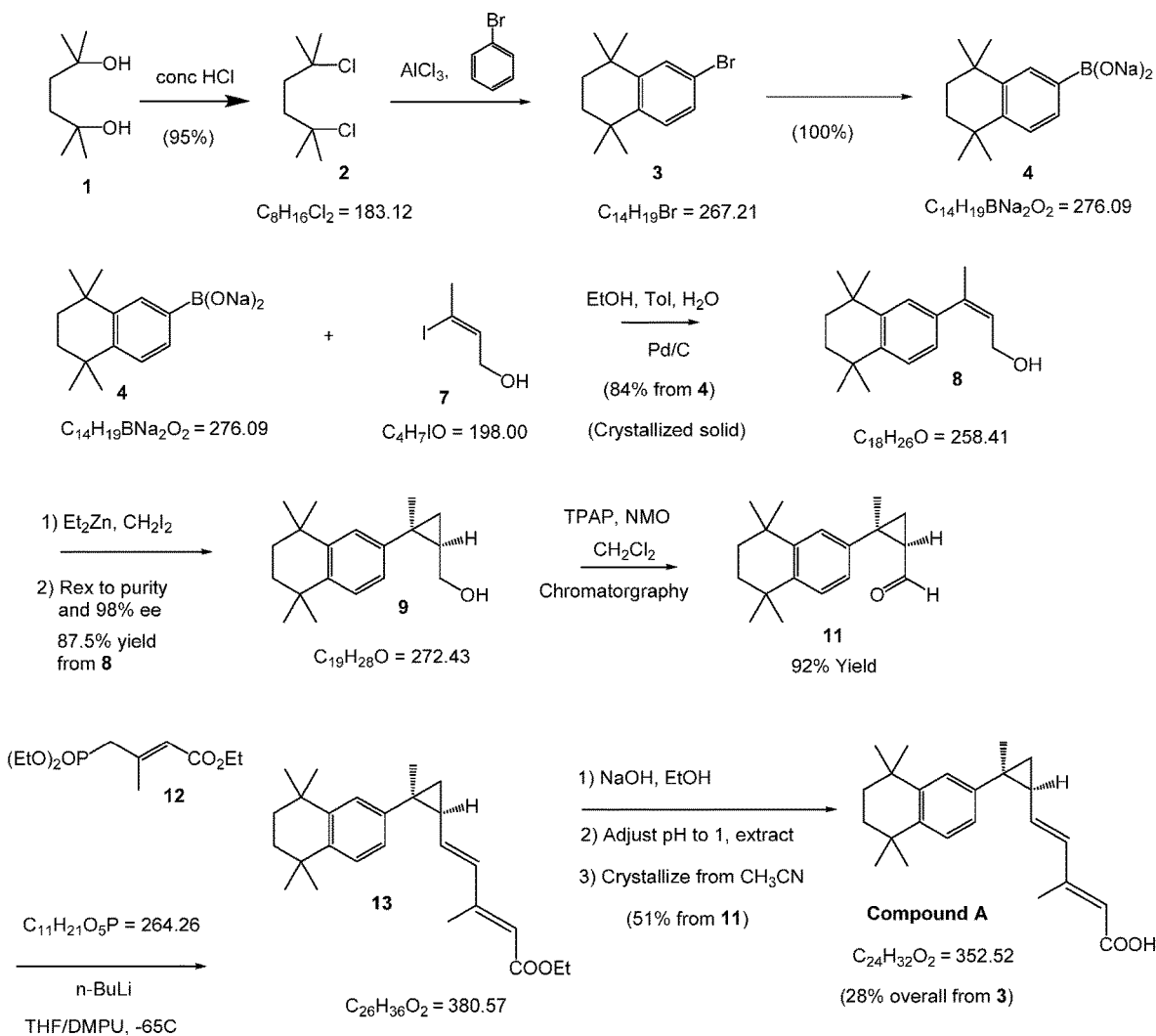
FIG. 4 shows a synthetic route for the preparation of Compound A.

In some embodiments, Compound A is prepared as shown in FIG. 4. As may be apparent to one of skill in the art, certain of the Formulae provided herein may be substituted for certain of the intermediate compounds of the scheme shown in FIG. 4 in order to arrive at alternative processes of preparing Compound A.

Figure 5:
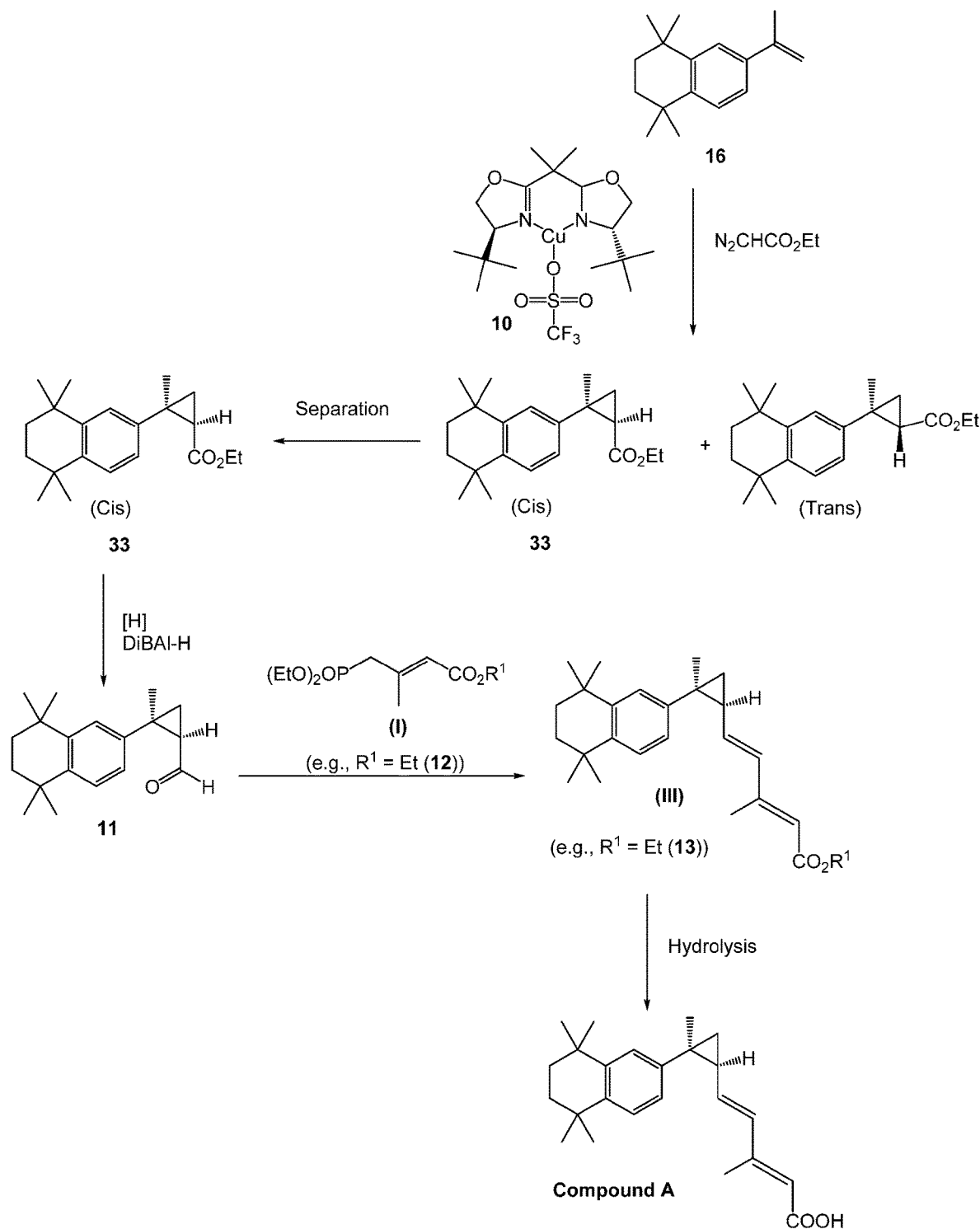
FIG. 5 shows a synthetic route for the preparation of Compound A.

In some embodiments, Compound A is prepared as shown in FIG. 5. As may be apparent to one of skill in the art, certain of the Formulae provided herein may be substituted for certain of the intermediate compounds of the scheme shown in FIG. 5 in order to arrive at alternative processes of preparing Compound A.

Figure 6:
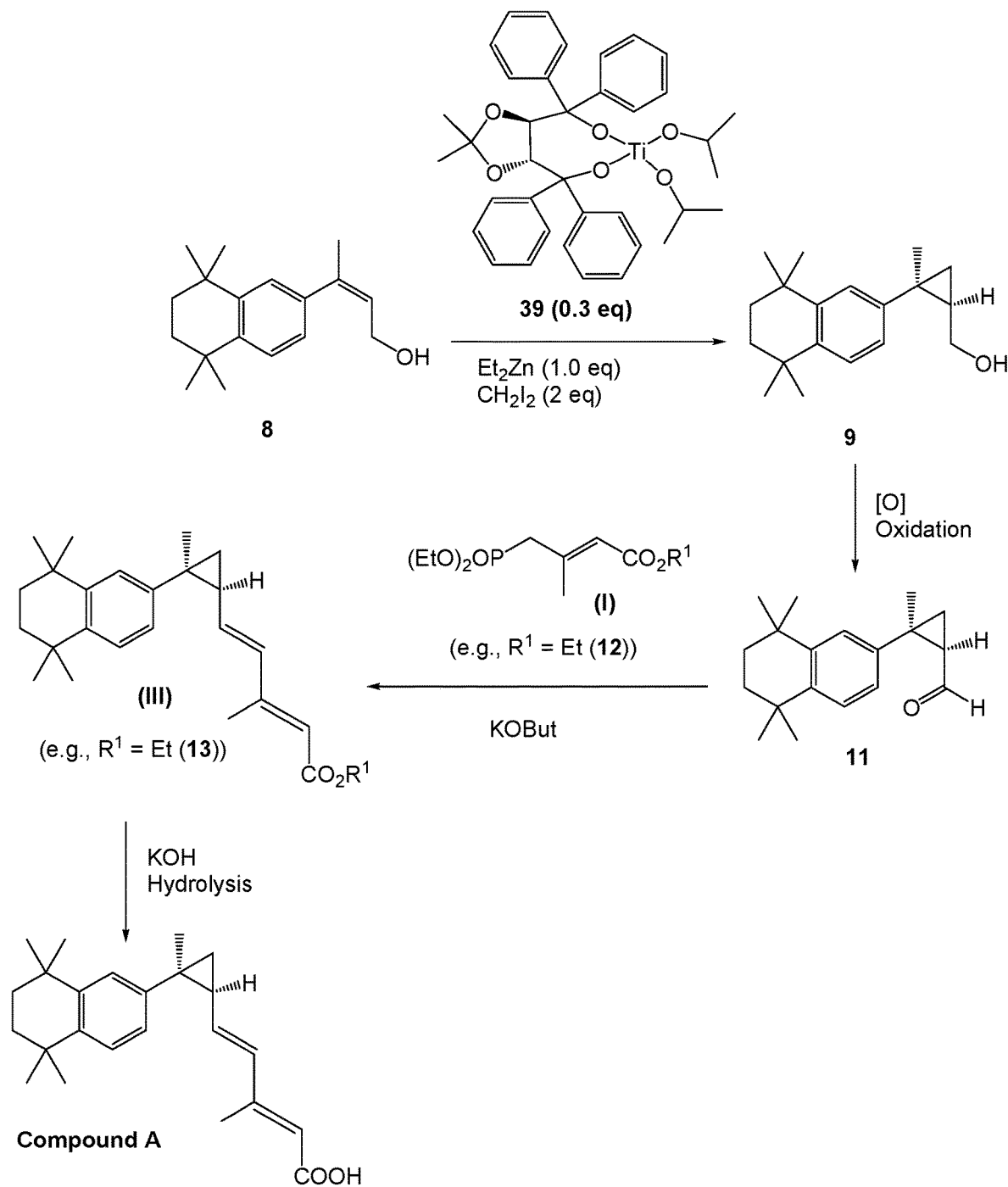
FIG. 6 shows a synthetic route for the preparation of Compound A.

In some embodiments, Compound A is prepared as shown in FIG. 6. As may be apparent to one of skill in the art, certain of the Formulae provided herein may be substituted for certain of the intermediate compounds of the scheme shown in FIG. 6 in order to arrive at alternative processes of preparing Compound A.

Methods

RXR agonists have diverse activities in the regulation of cellular growth and differentiation. Compound A is an RXR selective agonist that has been found to be useful in the treatment of several classes of disease or disorder, including cancer, nervous system disorders, muscular disorders, demyelinating diseases, and autoimmune diseases. Improved and synergistic effects have been obtained by also administering thyroid hormone.

As a selective RXR agonist Compound A activates RXR homo- and heterodimeric receptors at a substantially lower concentration than it activates retinoic acid receptors (RAR). This is important because activation of RAR can bring about unwanted and toxic side effects and can potentially counteract the beneficial effects arising from the RXR agonist activity. As seen in Table 2 and Table 3 Compound A activates RXR to 90% of maximum ($EC_{90}$) at concentration of 0.1 to 1 nM, depending on receptor subtype, yet induces only minimal (10%) activation ($EC_{10}$) of RAR as substantially higher concentrations of 200-300 nM, depending on receptor subtype. Compound A is a potent and specific RXR agonist with nanomolar binding affinities to the RXRs, whereas Compound B is a significantly less potent RXT agonist with significant RAR activity (see Table 4). RAR activation has been shown to be deleterious to survival of dopaminergic neurons, the neurons which are dying in Parkinson's disease. Additionally, RAR activation may counteract the beneficial effects of RXR activation in treating cancers.

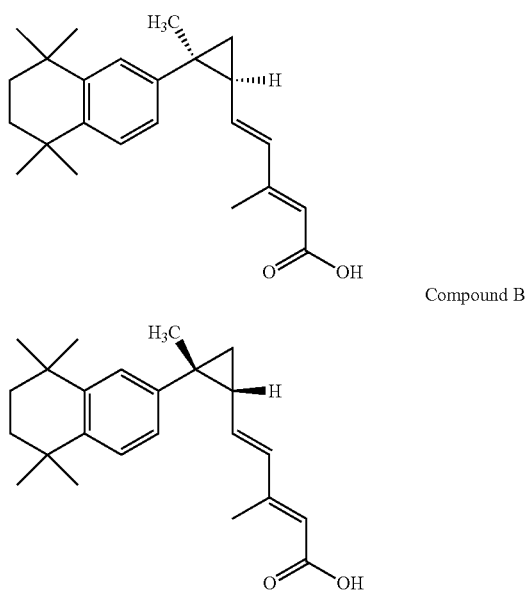

Compound A

Compound B

TABLE 2

RXR $EC_{90}$ and RAR $EC_{10}$ values of Compound A.

| RXR $EC_{90}$ (nM) | | | RAR $EC_{10}$ (nM) | | |
|---|---|---|---|---|---|
| α | β | γ | α | β | γ |
| 0.1 | 1 | 0.1 | 300 | 200 | 200 |

TABLE 3

Ratio of RXR $EC_{90}$ to RAR $EC_{10}$ for Compound A.

| RXR $EC_{90}$:RAR $EC_{10}$ ratio | | | |
|---|---|---|---|
| α | β | γ | Mean |
| 3000 | 200 | 2000 | 1730 |

TABLE 4

RXR and RAR activity of Compound A and Compound B.

| Compound Number | RARα nM | | RARβ nM | | RARγ nM | |
|---|---|---|---|---|---|---|
| | $EC_{50}$ | Kd | $EC_{50}$ | Kd | $EC_{50}$ | Kd |
| Compound A | NA | >30K | NA | >30K | NA | >30K |
| Compound B | >500 | 5750 | >500 | 6200 | >500 | >10K |

| Compound Number | RXRα nM | | RXRβ nM | | RXRγ nM | |
|---|---|---|---|---|---|---|
| | $EC_{50}$ | Kd | $EC_{50}$ | Kd | $EC_{50}$ | Kd |
| Compound A | 0.2 | 0.4 | 0.8 | 3.6 | 0.08 | 3.8 |
| Compound B | >500 | 60 | >500 | 210 | >500 | 180 |

Oral doses of 20 mg/m² do not exceed systemic concentrations of 200 nM and oral doses of about 0.014 mg/m² can produce transient systemic concentrations of about 0.1 nM. Thus some embodiments entail doses in the range of 0.014 to 20 mg/m². Nasal doses may be as much as 10-fold lower.

RXR agonists regulate gene expression leading to inhibition of growth or regression of some cancers. Compound A has shown activity against a variety of cancer types in vitro or in animal models, including hematologic cancers such as leukemia, and cutaneous T cell lymphoma, lung cancer (small cell and non-small cell), breast cancer (estrogen receptor positive and negative), cervical cancer, pancreatic cancer, and prostate cancer. Further description of the use of Compound A in the treatment of cancer can be found in U.S. Pat. No. 8,101,662, Treatment of Cancer with Specific RXR Agonists, and WO2017/075612 Treatment of Cancer with Combinations of RXR Agonists and Thyroid Hormone, each of which is incorporated by reference for all that it teaches about such use.

Compound A has also been found to have immunomodulatory effects, especially the regulation of Th17/Treg ratios in favor of Treg cells leading to a dampening of immune responses and of inflammation. Further Compound A has been found to have neuroprotective effects and to promote oligodendrocyte differentiation and remyelination. Thus Compound A can be useful in the treatment of a variety of diseases with neurodegenerative and/or autoimmune components including muscular and nervous system disorders. Exemplary diseases that can be treated with Compound A include Parkinson's disease, Alzheimer's disease, multiple sclerosis, schizophrenia, amyotrophic lateral sclerosis, ischemic injury, traumatic injury, a depressive disorder, or age-related neurodegeneration. In some embodiments appropriate dosages are in the range of 0.001 to 100 mg/kg/day. In other embodiments the dosage can be 0.001 to 0.2 mg/kg/day or 0.1 to 3 mg/kg/day. Further description of the use of Compound A in the treatment of neurodegenerative and autoimmune diseases can be found in: U.S. Pat. No. 10,034,854, Autoimmune Disorder Treatment using RXR Agonists; USPPN 2015-0038585, Treatment of Diseases by Concurrently Eliciting Remyelination Effects and Immunomodulatory Effects Using Selective RXR Agonists; U.S. Pat. No. 9,877,941, Treatment of Nervous System Disorders Using Combinations of RXR Agonists and Thyroid Hormones; WO2017/155577, Treatment of Autoimmune Diseases with Combinations of RXR Agonists and Thyroid Hormones; WO2017/155578, Treatment of Muscular Disorders with Combinations of RXR Agonists and Thyroid Hormones; each of which is incorporated by reference for all that it teaches about such uses.

Thus, in some embodiments provided herein are methods of treating cancer comprising administering to a subject in need thereof an effective amount of Compound 38, or a pharmaceutically acceptable salt thereof, wherein: Compound 38 has an enantiomeric excess of Compound A, of at least about 98.0%; and the compound is prepared by a synthetic process, and the synthetic process includes a process of preparing an intermediate compound as described herein. In some embodiments, the intermediate compound is Formula (XIa). In some embodiments, Formula (XIa) is prepared by a process provided herein.

In some embodiments, provided herein are methods of treating cancer comprising, administering to a subject in need thereof a compound (i.e., an RXR agonist, e.g., Compound 38 having an enantiomeric excess of at least about 98% (e.g., at least about 99.0%, e.g., at least about 99.5%) of Compound A, Compound A having an enantiomeric excess of at least about 98% (e.g., at least about 99.0%, e.g., at least about 99.5%), a composition thereof, or a pharmaceutical composition thereof), at a therapeutically effective dose from about 0.1 to about 20 mg/m²/day.

In some embodiments, the therapeutically effective dose of the RXR agonist is a dose below the retinoic acid receptor (RAR) activating threshold and at or above the RXR effective dose.

In some embodiments, the cancer is a hematologic malignancy, lung cancer, prostate cancer, breast cancer, pancreatic cancer, colon cancer, or cervical cancer.

In some embodiments, the treating further comprises administration of thyroid hormone to the subject.

Also provided herein are methods of treating a nervous system disorder, a muscular disorder, a demyelinating disease, or an autoimmune disease in a subject in need thereof, comprising, administering to the subject a therapeutically effective amount of a compound (i.e., an RXR agonist, e.g., Compound 38 having an enantiomeric excess of at least about 98% (e.g., at least about 99.0%, e.g., at least about 99.5%) of Compound A, Compound A having an enantiomeric excess of at least about 98% (e.g., at least about 99.0%, e.g., at least about 99.5%), a composition thereof, or a pharmaceutical composition thereof), wherein the therapeutically effective amount is from 0.001 mg/kg/day to about 100 mg/kg/day.

In some embodiments, the nervous system disorder is Parkinson's disease, Alzheimer's disease, multiple sclerosis, schizophrenia, amyotrophic lateral sclerosis, ischemic injury, traumatic injury, a depressive disorder, or age-related neurodegeneration.

In some embodiments, the treating further comprises administration of thyroid hormone.

In some embodiments, the therapeutically effective amount is about 0.001 mg/kg/day to about 0.2 mg/kg/day.

In some embodiments, the therapeutically effective amount is about 0.1 mg/kg/day to about 3.0 mg/kg/day.

In some embodiments, the RXR agonist is administered at a therapeutically effective dose, wherein the dose is below the retinoic acid receptor (RAR) activating threshold and at or above the RXR effective dose.

In some embodiments, the RXR agonist has an enantiomeric excess of Compound A that essentially eliminates, or reduces to an undetectable level, RAR activation by an enantiomer of Compound A (e.g., Compound B).

Kits and Articles of Manufacture

Also provided herein are kits, comprising a compound provided herein.

Also provided herein are articles of manufacture, comprising a compound provided herein.

In some embodiments, the kit or article of manufacture further comprises instructions for use thereof.

EXAMPLES

Example 1: Synthesis of Compound 29

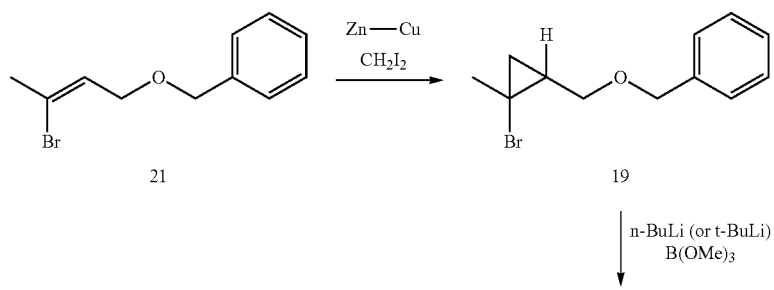

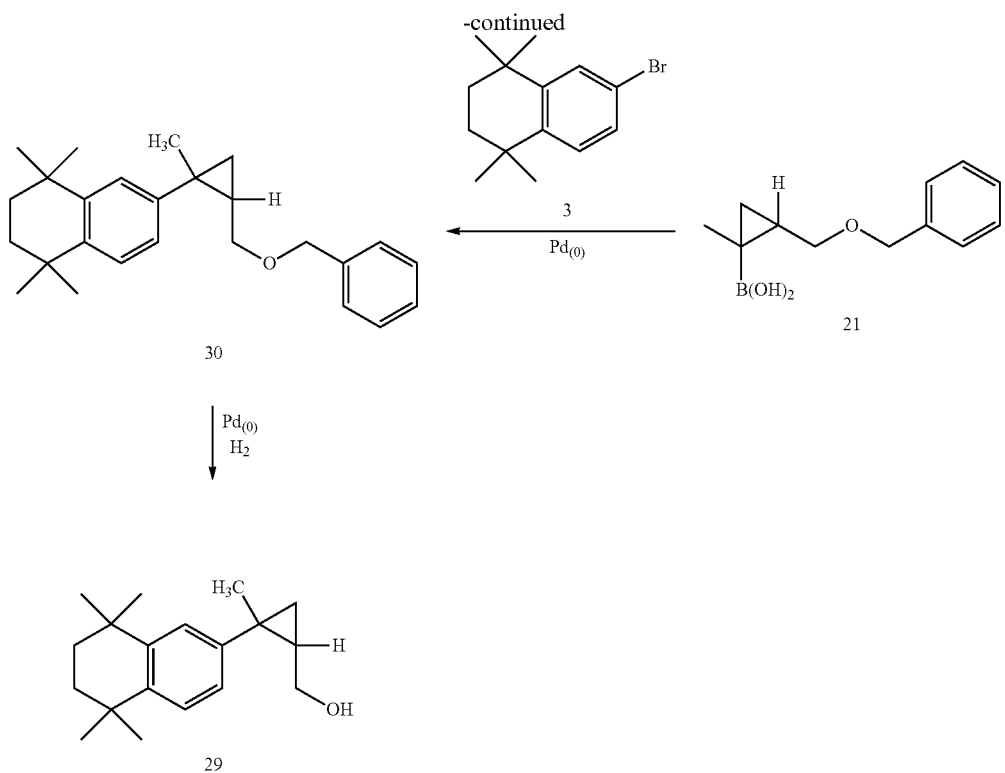

Compound 18 (1 eq) in dry THF or dry ether (10 mL), on treatment with Zn—Cu couple (1-3 eq) or similar reagents in the presence of diiodomethane (1-3 eq) and stirred at appropriate temperature for several hours and reaction is quenched with water. The solid Zn—Cu mixture is filtered off, and the organic layer is separated and solvent is removed. The crude product is purified, this gives the cyclopropyl product 19.

The cyclopropyl product 19 (1 eq) in anhydrous THF (10 mL) on reaction with n-BuLi or sec-BuLi or t-BuLi at appropriate temperature and for an appropriate length of time stirred then on treatment with trimethyl borate or similar borate reagent followed by quenching the reaction with dilute acid followed by reaction with $NaOH_{(aq)}$ gives the borate product 21.

The borate Compound 21 (1 eq) in DME or THF (10 mL) and some MeOH in the presence of bromotetralin Compound 3 (1 eq) in the presence of $Pd(PPh_3)_4$ (catalytic amount) and 1 eq of $K2CO_3$ and heated for appropriate time and at appropriate temp for appropriate length of time gives the crude cyclopropyl-tetralin Compound 30. The crude reaction is extracted with Ethylacetate and dried and purified giving Compound 30.

Compound 30 (1 eq) on reaction with Pd—C (catalytic amount) in Ethyl acetate or MeOH (10 mL) under hydrogen atmosphere at appropriate pressure gives the cyclopropyl alcohol 29. The Pd—C solid is filtered off on removal of solvent followed by purification gives cyclopropyl alcohol 29.

As is apparent to one of skill in the art, certain of the Formulae provided herein may be substituted for certain of the intermediate compounds of the scheme shown in Example 1 in order to arrive at alternative processes of preparing Compound 29.

Example 2: Synthesis of Compound 37

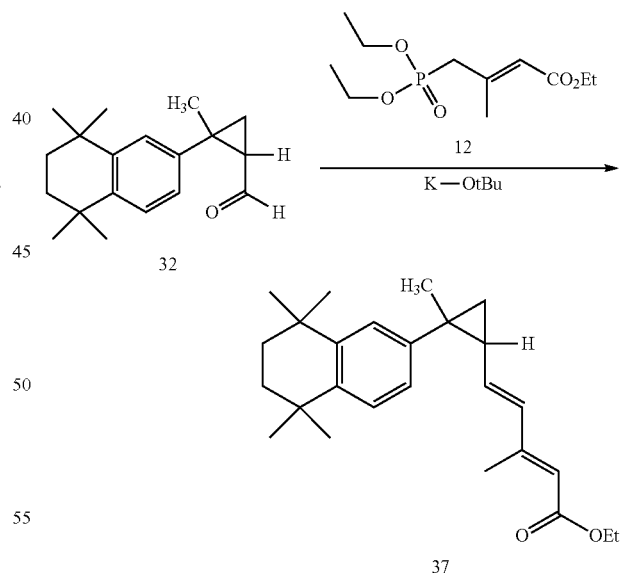

Compound 12 (1.1 eq) in THF at appropriate temperature is treated with KOt-Bu (1.1 eq) under inert (nitrogen or argon) atmosphere for appropriate length of time. Then to this mixture is added Compound 32 (1 eq) in THF or ether solvent, at appropriate temperature and stirred for appropriate length of time, followed by quenching the reaction with water and extracted with ethyl acetate. The ethyl acetate layer on drying and purification gives product 37.

Example 3: Synthesis of Compound 34

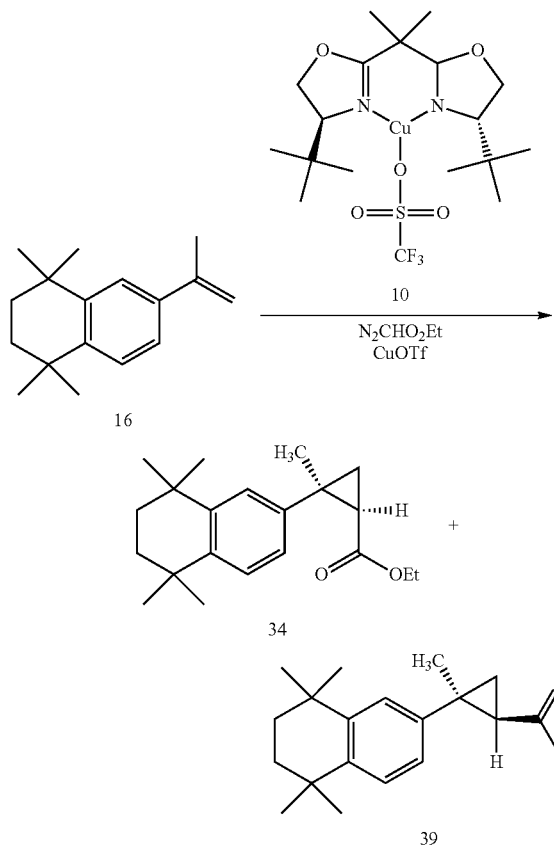

To a suspension of copper triflate (CuOTf, 6.8 mg, 0.027 mmol), is added a solution of chiral catalyst (8.1 mg, 0.028 mmol) in chloroform (9 mL) to form chiral catalyst Compound 10. After one hour the solution is passed through a canula, comprised of a needle and a hub packed with glass wool. To this mixture is added Compound 16 (3.19 g, 14 mmol) and N₂CHCO₂Et (309 mg, 2.71 mmol) in anhydrous chloroform (10 mL) slowly (over a period of 1.5 hours). After 14 hours the mixture is concentrated under vacuum. The mixture is purified by silicagel column chromatography. The desired Compound 34 is isolated by chiral chromatography or MPLC (Masamune et al Tet. Letts, 1990, 31, 6005; Evans et al J. A. C. S. 1991, 113, 726; Masamune et al Tet. Letts, 1991, 32, 7373).

Example 4: Synthesis of Compound 11

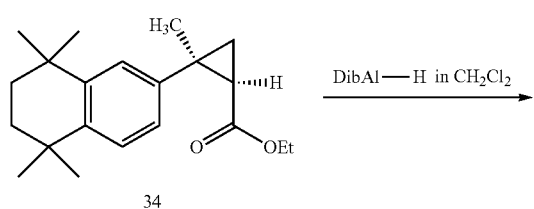

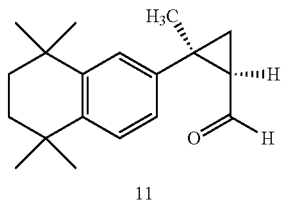

To a cold (−78° C.) solution of Compound 34 (312 mg, 1 mmol) in anhydrous dichloromethane (6 mL) is added diisobutylaluminium hydride in dichloromethane (1 M solution, 1.1 mL) slowly (over 5 min). The cold reaction is stirred for 4 hours or until the reaction is complete. The reaction is quenched by adding water (1 mL), diluted with dichloromethane (10 mL), washed with dilute (5%) aq. HCl or NaHCO₃ solution (5 mL), dried and solvent distilled off. Compound 11 is isolated and used in the next step.

Example 5: Synthesis of Compound 13

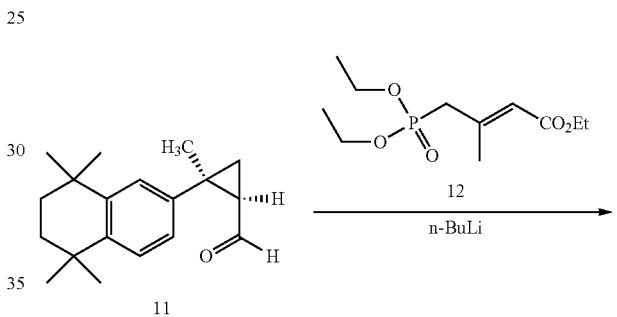

To a cold (−78° C.) solution of Compound 12 (290 mg, 1.1 mmol) in anhydrous tetrahydrofuran (6 mL) is added n-BuLi (1.6 M solution, 0.7 mL). The cold reaction is stirred for 20 min, then a solution of Compound 11 (264 mg, 1 mmol) in anhydrous tetrahydrofuran (3 mL) is added and stirred the mixture for 3 hours or until the reaction is complete. The reaction is quenched by adding water (1 mL), diluted with ethylacetate (30 mL), washed with brine (5 mL) dried and solvent is distilled off. Compound 13 is isolated after column chromatographic purification.

Example 6: Synthesis of Compound A

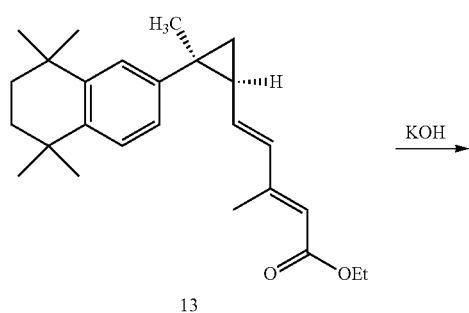

To a solution of Compound 13 (290 mg, 1.1 mmol) in methanol (2 mL), is added KOH$_{(aq)}$ (1 M solution, 3 mL) and heated to 80° C. for 2 hours or until the reaction is complete. The reaction mixture is cooled to ambient temperature and acidified with dilute HCl in water (10%, 3 mL). The reaction is extracted with Ethylacetate (3×10 mL), dried and solvent is distilled off. Compound A is isolated by recrystallization or chromatographic purification.

Example 7: Synthesis of Compound 33

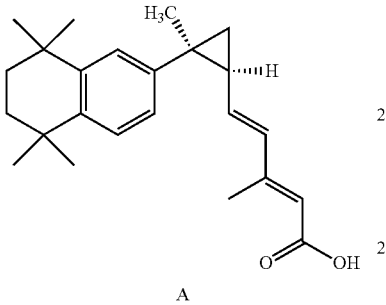

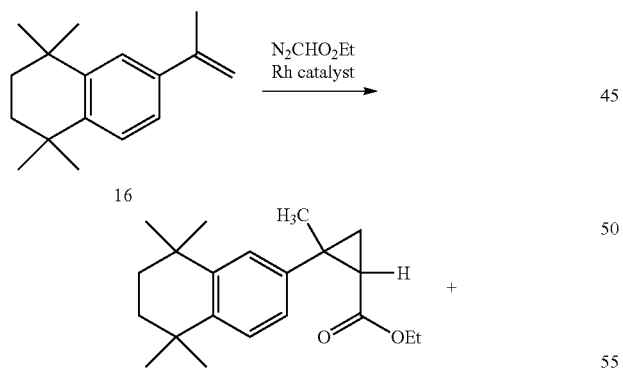

A solution of N$_2$CHCO$_2$Et (228 mg, 2 mmol) in anhydrous dichloromethane (3 mL) is added slowly (over a period of 5 hours) to a solution of Compound 16 (2.28 g, 10 mmol), Rhodium catalyst (4.4 mg, 0.01 mmol) and dichloromethane at ambient temperature. The mixture is stirred for two hours or until the reaction is complete, and passed through a short column of alumina with dichloromethane as eluent to remove the Rh(OAc)$_2$ catalyst. Then, solvent and excess Compound 16 is removed by distillation. A mixture of the cis isomer 33 and trans isomer 40 is isolated and separated by chromatography. Compound 33 is used in the next step (Callot, H. J.; Metz, F.; Tetrahedron 1985, 41, 4495; Maxwell, J. L. et al Organometallics 92, 11, 645; Callot, H. J.; Piechoeki, C.; Tetrahedron Lett. 1980, 21, 3489).

Example 8: Synthesis of Compound 32

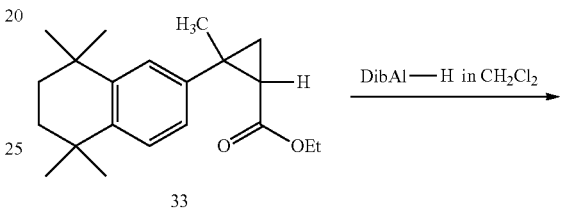

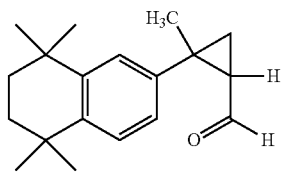

To a cold (−78° C.) solution of Compound 33 (312 mg, 1 mmol) in anhydrous dichloromethane (6 mL) is added diisobutylaluminium hydride in dichloromethane (1 M solution, 1.1 mL) slowly (over 5 min). The cold reaction is stirred for 4 hours or until the reaction is complete. The reaction is quenched by adding water (1 mL), diluted with dichloromethane (10 mL), washed with dilute (5%) aq. HCl solution (5 mL), dried and solvent distilled off, Compound 32 is isolated and used in the next step.

Example 9: Synthesis of Compound 37

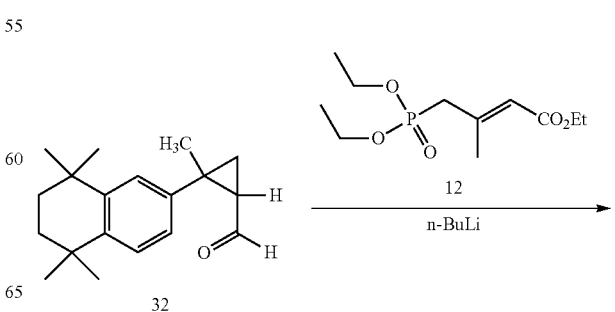

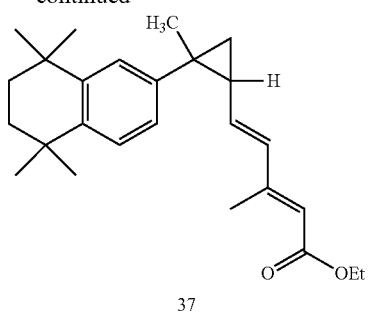

37

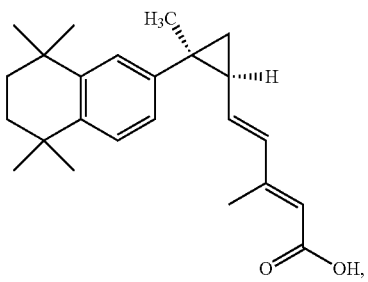

Compound A

To a cold (−78° C.) solution of Compound 12 (290 mg, 1.1 mmol) in anhydrous tetrahydrofuran (6 mL) is added n-BuLi (1.6 M solution, 0.7 mL). The cold reaction is stirred for 20 min, then a solution of Compound 32 (264 mg, 1 mmol) in anhydrous tetrahydrofuran (3 mL) is added and stirred the mixture for 3 hours or until the reaction is complete. The reaction is quenched by adding water (1 mL), diluted with ethylacetate (30 mL), washed with brine (5 mL) dried and solvent is distilled off. Compound 37 is isolated after column chromatographic purification.

Example 10: Synthesis of Compound 38

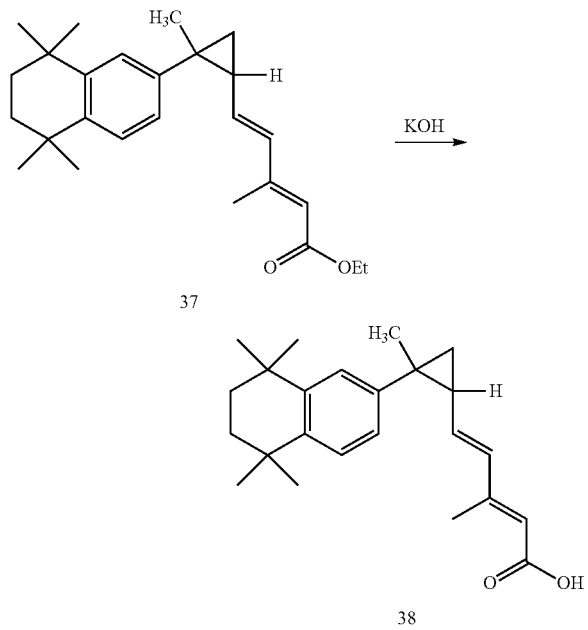

To a solution of Compound 37 (290 mg, 1.1 mmol), methanol (2 mL), is added $KOH_{(aq)}$ (1 M solution, 3 mL) and heated to 80° C. for 2 hours or until the reaction is complete. The reaction mixture is cooled to ambient temperature and acidified with dilute HCl in water (10%, 3 mL), The reaction is extracted with Ethylacetate (3×10 mL), dried and solvent is distilled off. Compound 38 is isolated by recrystallization or chromatographic purification.

In some embodiments provided herein, Compound 38 has an enantiomeric excess of Compound A.

of at least about 80.0% (e.g., at least about 85%, 90%, 91%, 92%, 93%, 94%, 95%, 96%, 97%, 98%, or 99%). In some embodiments Compound 38 has an enantiomeric excess of at least about 98.0% (e.g., at least about 98.5%, 99.0%. 99.5%, 99.6%, 99.7%, 99.8%, 99.9%, 99.99%, or 99.999%).

Example 11: Synthesis of Compound 9

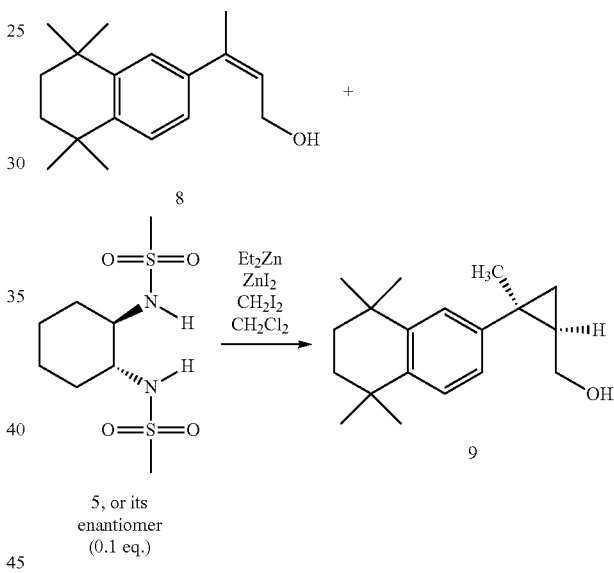

To a cold flask (Flask A) (0° C.) containing Compound 8 (256 mg, 1 mmol), and the sulfonamide catalyst (Compound 5 or its enantiomer, 27 mg, 0.1 mmol) is added $CH_2Cl_2$ (3 mL) under inert atmosphere. To this solution, is added $Et_2Zn$ (113 μL, 1.1 mmol), and stirred for 10 min. To another flask (Flask B), is added iodine (508 mg, 2 mmol) and $CH_2Cl_2$ (10 mL), this suspension is cooled to 0° C. and $Et_2Zn$ (103 μL, 1 mmol) is added and stirred for 10 min. In another flask (Flask C), $CH_2I_2$ (161 μL, 2 mmol) and $CH_2Cl_2$ (24 mL) is added, the solution is cooled to 0° C. and $Et_2Zn$ (103 μL, 1 mmol) is added and stirred for 5 min. The contents of Flask A is cannulated into Flask B at 0° C. and stirred for 2 min, then these contents is cannulated to Flask C, the reaction contents in Flask C is stirred at 0° C. until the reaction is complete. The reaction is quenched by adding $NaOH_{(aq)}$ (2 M solution, 13 mL). The aq. layer is separated and extracted with $CH_2Cl_2$ (2×15 mL), combined organic layer is dried and solvent removed and purified by silicagel column chromatography and the product (Compound 9) is isolated (Denmark, S. E.; Christenson, B. L.; O Connor, S. P.; Tetrahedron Letts, 1995, 36, 2219; Denmark, S. E.; Chris-

Example 12: Synthesis of Compound 11

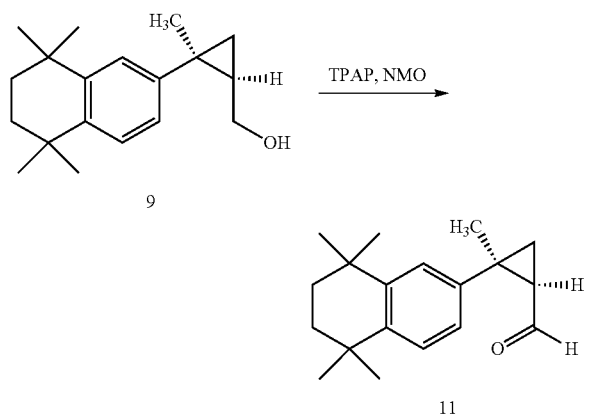

To a solution of Compound 9 (270 mg, 1 mmol) in CH$_2$Cl$_2$ (6 mL) is added molecular sieves (1 g), TPAP (3 mg), NMO (141 mg, 1.2 mmol) and is stirred at ambient temperature until the reaction is complete. The reaction is passed through a short silica gel column and eluted with ethylacetate-hexane mixture. The product (Compound 11) is isolated after removal of the solvent.

Example 13: Synthesis of Compound 12

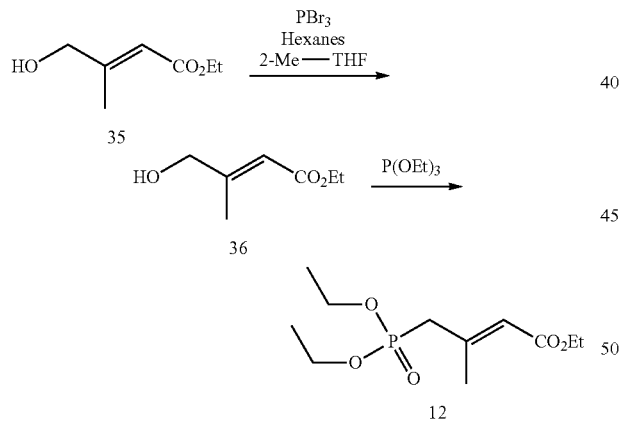

Compound 36: The supplied procedure uses PBr$_3$ in a mixture of hexane and ethyl ether to convert alcohol 35 into bromide 36 in 79% yield. Work up reveals that the product is contaminated with substantial amounts of ring opened materials derived from 2-MeTHF (NMR).

Results: Compound 36 Run 1. To a solution of 26 g (0.18 mol) of 35 in 400 mL of heptane and 150 mL of MeTHF at −5 to −10° C. is added PBr$_3$ (exothermic, 51.3 g, 0.189 mol), The mixture is stirred cold for 1 h, then at room temp overnight. Ion paired chromatography (IPC) shows peak to peak conversion. The mixture is quenched (cold) by adding 225 mL of brine (exothermic). The organic layer is stripped to give 51 g (138%) of an oil that showed (NMR) substantial impurities derived from reaction with the MeTHF. The oil is redissolved in 400 mL of heptane and washed with 8% NaHCO$_3$ (2×100 mL). The solution is dried (MgSO$_4$), filtered and stripped to give 41 g (110%) of oil. The NMR is substantially purer but not clean. This material is chromatographed or distilled to purify it.

Alternatively, dichloromethane is used as the sole solvent. Since 1 eq of PBr$_3$ gives clean conversion to 36 (above) and reacts with the MeTHF, more than one Br might be reactive to the alcohol. Thus, on 0.1× the above scale, 2.6 g of 35 in 40 mL of DCM is treated with 0.5 eq of PBr$_3$ at <−5° C. Ion paired chromatography (IPC) shows that an intermediate forms and decreases over time going to product. However, starting material and a polar intermediate are not fully consumed. Another 0.25 eq (total 0.75 eq) is added and the reaction is run overnight. Work up gave 3.7 g (quantitative) of product. However, the longer retention time impurity (Z isomer) is at a significantly higher level (7%) than in the previous run. Looking at the liquid chromatography traces, it can be seen to grow over time. These data suggest that the ether in the original procedure functions as a weak Lewis base to temper the effects of HBr byproduct.

Results: Compound 36 Run 2. To a solution of 2.6 g (0.018 mol) of 35 in 40 mL of DCM at −5 to −10° C. is added PBr$_3$ (exothermic, 2.3 g, 0.009 mol, 0.5 eq). The mixture is stirred at room temp for 5 h but does not go to completion. The mixture is chilled and another 0.25 eq is added and the reaction is stirred overnight at room temp. The reaction is chilled and quenched with 10 mL of water (exothermic), dried (MgSO$_4$) and stripped to give 3.7 g (quantitative) of a clear oil. HPLC shows the undesired Z isomer (NMR, GCMS) at about 7%.

Example 14: Synthesis of Compound 9

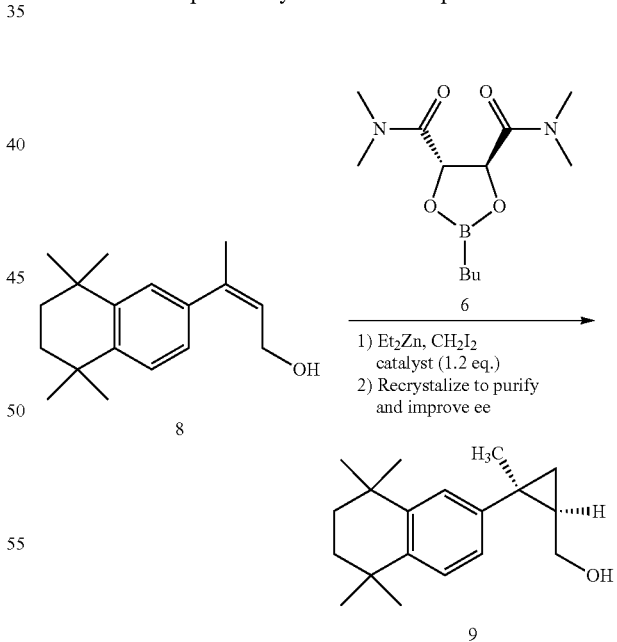

Compound 9 (Simmons-Smith Reaction): all additions are done over at least 20 minutes and at about −5° C. Procedure: purge the reactor with N$_2$. Charge the 10 L reactor with 8 (200 g), DCM (4 L), and boronate catalyst (250 g). Turn on the stirrer. Cool to −5 to 10° C., Add the first Et$_2$Zn solution (800 mL, 1.1 eq) holding −5 to 10° C. (exothermic) over 20-60 min. Stir ca 20-30 min cold. Add the first charge of CH$_2$I$_2$ (228 g) holding −5 to 10° C. (mildly exothermic) over 20-60 min (pot darkens as CH$_2$I$_2$ addition started). Add the second charge of Et$_2$Zn solution (800 mL, 1.1 eq) holding −5 to −10° C. (mildly exothermic) over 20-60 min. Stir ca 20-30 min cold. Add the second charge CH$_2$I$_2$ (228 g) holding −5 to 10° C. (slightly exothermic) over 20-60 min. After the second addition of CH$_2$I$_2$, a gummy solid coagulates as a stirrable mass. The gummy solid appears to thin out as temperature is raised to 0° C. After overnight, the mass completely breaks up; the pot is a well-stirred slurry of insolubles. Stir overnight at 0° C. Pull IPC. Warm to 20° C. Pull IPC. Add the third charge of Et$_2$Zn solution (800 mL, 1.1 eq) holding −4 to −7° C. (not exothermic) over 20-60 min. Stir ca 20-30 min cold. Add the third charge of CH$_2$I$_2$ (228 g) holding −5 to 10° C. (slightly exothermic) over 20-60 min. Stir ca 20-30 min cold. Warm to 20° C. Stir 30 min. An additional 12% of the 1.1 eq charge is added and the reaction is complete after a second overnight period. When complete, cool to 0-5° C. and add 3N HCl (2 L). The first 200 mL is exothermic (to 20° C.) with some foaming and off gas (easily controlled). After cooling again to 0° C., the remaining acid is charged with only a 9° C. exotherm. Stir 30 min at 15-25° C. and cut layers. The lower layer is orange and turbidity free. There is a dark rag layer that migrates to the interface and mostly dissolves. To the extent possible, the rag is taken with the aqueous. Distill off (vacuum) most of the DCM. This run is done in a rotovap for mechanical reasons. Vacuum is used to keep the temperature down as a general safety precaution. The DCM removal is done to, at least, a) decrease the working volume, and, more importantly, b) to control the density of the organic solution and prevent subsequent layer inversion. A total of 3.2 L of the initial 4.0 L is removed. The exact amount is not critical. Removal of the DCM at this point also makes the final strip (toluene) easier (little to no low boiler), Wash with 1 N HCl (1 L). Cut layers and charge NaOH solution (250 g of 50%+890 g water-total: 1 L). Cool to 5° C. Add 35% H$_2$O$_2$ (200 g). The first 80 mL of the addition is exothermic: temperature held <12° C. The rest of the addition is not noticeably exothermic. Warm to 20° C. Cut layers, Charge 20% Na$_2$SO$_3$ (625 g), stir 5-15 min and cut layers. The addition is not exothermic. This wash is later combined with the H$_2$O$_2$ waste fraction in a separate flask producing a slow (5-10 min) exotherm from 25° C. to 40° C. The small controlled exotherm indicates that the Na$_2$SO$_3$ can be added to the reactor without prior separation of the H$_2$O$_2$. Wash 250 mL of brine. Filter organic layer through Solka floc 40 to remove turbidity. Strip off solvents with vacuum (bath 50° C., 7 Torr).

Work up gives 238 g (113%) of an orange oil that contains 20 mol % (8 wt %) of toluene. Chiral HPLC shows 11% of the wrong enantiomer, in contrast to the 4% seen in an analogous 20 g run.

The enantioselectivity is improved by the above-described sequential addition of the reagents in the cyclopropanation step. Additionally, the equivalents of reagents is minimized, which leads to cost savings and easier work up conditions.

Example 15: Synthesis of Butylboronic Acid (Compound 25)

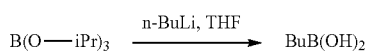

Butylboronic acid is prepared on a medium scale in a 10 L reactor by adding the BuLi to triisopropyl borate at −42 to −50° C. to give 197 g (76%). The V$_{max}$ was 6.5 L (32.5 L/kg).

Example 16: Synthesis of Compound 27

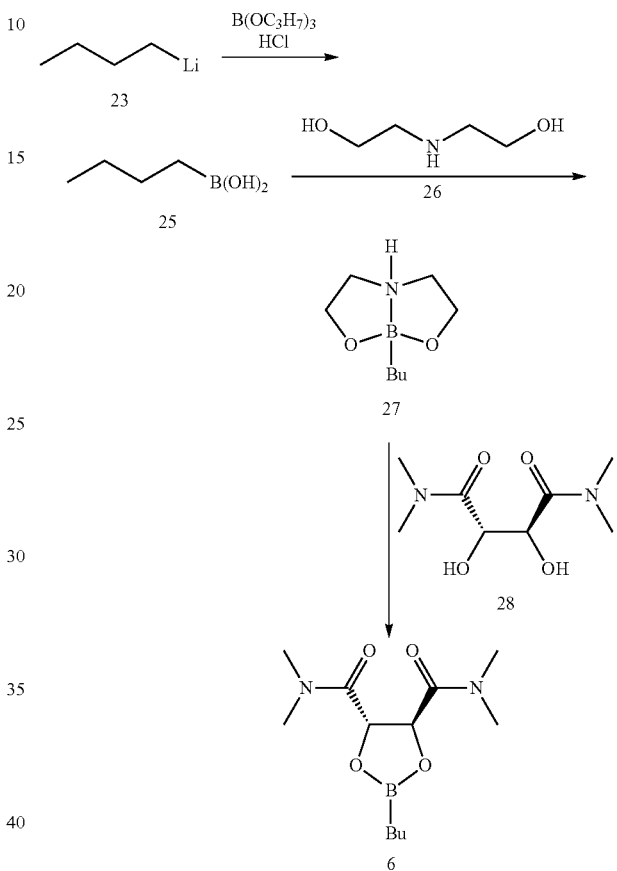

Diethanolamine Complex (27) is prepared from the above butylboronic acid by reaction with 1.1 eq of diethanolamine (DEA) in the mixed solvent system of MTBE and DCM with 4 Å molecular sieves as a dehydrating agent. Procedure: purge the reactor with N$_2$. Charge the 10 L reactor with B(OiPr)$_3$ (530 g) and THF (3750 mL). Cool to −45° C. (the reactor must be heavily insulated). Add the BuLi soln (1587 mL) holding −42 to −50° C. (3 h) (exothermic; a precipitate forms at 3 h). Stir 10-30 min. Warm to 15° C. over 3-18 h (overnight is acceptable; insolubles become notably thicker at ca −42° C. during warm up). Charge 4N HCl (440 mL) charged to the reactor, which results in only a 12° C. temperature rise. All solids dissolve to two clear layers. Stir 10 min. Drain aqueous. Strip off the solvents from the organic layer; white semi-solid. Take up the residue in 1.2 L of water, which is added to the rotovap flask and heated to 80-85° C. to give a highly turbid solution (two liquid layers). The flask contents were transferred to a 4 L beaker fitted with a mechanical stirrer and thermocouple. The mixture was cooled slowly with a N$_2$ stream to remove residual THF and IPA. Solids formed at 50-55° C. The solids were filtered off in a 1 L coarse frit funnel, washed with minimal water and the cake pressed with a rubber sheet and/or elephant's foot. The sheet was removed and vacuum continued to deliquor the cake. The solids were fluffed up and vacuum continued for another 30 min (N₂ stream): 230 g of wet cake. Vacuum drying (no heat, 1-2 L/min N₂ stream) overnight gave 197 g (76%) of white non-sticky flakes. General: There is no IPC analysis for completion. NMR (DMSO-d) of the final compound matches the reference and shows no water (not definitive for dryness). Boronic acids are known to partially dehydrate depending on conditions and are also susceptible to air oxidation. Therefore, they should be stored under N₂.

In some embodiments, Compound 6 is formed (e.g., in situ) by contacting Compound 27 with Compound 28 in a suitable solvent to form Compound 6.

Yield: 258 g, 79% (purity 96%, NMR). A second crop (49 g, 15%) is also taken with only 75% purity (NMR). Compound 27 serves as a stable solid for holding the potentially unstable butylboronic acid.

Example 17: Synthesis of Compound 27

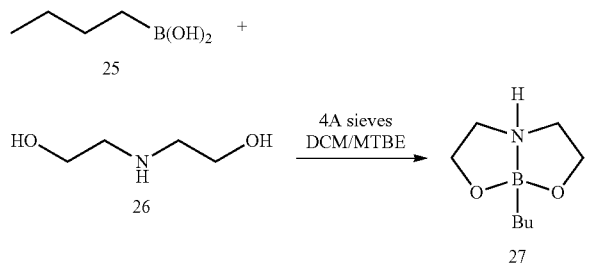

Procedure: purge the reactor with N₂. Charge the 10 L reactor with BuB(OH)₂ (196 g), DEA (222 g), DCM (2.1 L) and MTBE (2.1 L). Charge the mol sieves (345 g). Diethanolamine (DEA) is a viscous liquid (mp=27-31° C.) and difficult to pour and transfer completely. Some solvent is reserved for rinsing the charging funnel after the sieves. Stir 2-24 h. Pull IPC. Filter off the solids and wash with DCM (0.5 L). Strip off the solvents. Take up the residue in DCM (1.1 L). The residue is soluble in the DCM. Charge MTBE (2.5 L). The mixture becomes turbid when charging the MTBE. Allow to stand in cold room overnight. Good well separated crystals after standing (no stirring) overnight. Break up chunks. Filter off solids, and wash with minimal MTBE. Vacuum dry (30° C., N₂) to constant weight: 258 g (79%). Concentrate the filtrates to incite further crystallization and take a second crop: 49 g (15%).

Example 18: Recrystallization of Compound 9

Crystallization comprises the following procedure: dissolve the crude in MeOH and strip to remove residual solvent from the crude that might affect the crystallization. Dissolve the crude in 3 volumes of MeOH (filtered to remove turbidity). Dilute with 7.6 volumes of ethylene glycol (EG, seeding). Adding the EG slowly or rapidly produces only turbidity (no crystals with or without seeding). Dilute slowly with 2 volumes of water (seeding). Adding the water dropwise produces insoluble (oil) material as each drop hits the liquid (no crystals with or without seeding). Gradually, over the course of the addition, gummy material separates that may stick to the walls and stirrer. Eventually, a well-stirred slurry develops (gummy material remains stuck to walls; i.e. does not redissolve or resuspend). Age overnight. Filter off solids. Wash with 5:1 EG:MeOH, then slurry wash with water.

This process is not crystallization, but gummification, which mostly turns over to crystals. It does improve the enantiomeric purity although not as much as desired.

The water wet cake from the crystallization cannot be directly subjected to a second crystallization but must be dried (air or redissolving) first. The ratio of solvents seems to be important.

The second crystallization improves the enantiomeric purity but not sufficiently (Need 99:1).

An aliquot of the final slurry (before filtration) is heated (gun) to give a complete solution. On standing, some amorphous mass plus some crystals form.

Compound 9 (Recrystallization): The stripped crude (238 g, 113%) of Example 14 was dissolved in 0.9 L of MeOH and stripped to dryness (116 g) in order to remove residual toluene which would be expected to interfere with the crystallization. Target solvent ratios are MeOH-3, ethylene glycol-7.6, water-2 (vol. relative to the theoretical weight of 9). Thus, in a 5 L mechanically stirred flask, the newly stripped crude is dissolved in MeOH (600 mL) and ethylene glycol added rapidly until the mixture becomes turbid (ca 90% of the 1520 mL). The remainder is added slowly (1-2 h) with seeding; no crystals form. Ca 50 mL of the 400 mL of water is added slowly (1-2 h) with seeding, then stirred overnight; no crystals form. The remainder is added slowly (2-3 h) with seeding. Gummy cotton-like crystals separate and stir well (no coagulation). After stirring overnight, the solids are filtered off (2 L coarse frit) and washed with 5:1 EG:MeOH (2×250 mL, displacement) the water (3×700 mL, slurry). The chiral HPLC is not pure enough so a second crystallization is needed. Compound 9 is recovered by dissolving in hexanes (separating the water) and stripping to give 183 g (see Table 1) after a second crystallization.

Example 19: Synthesis of Compound 4

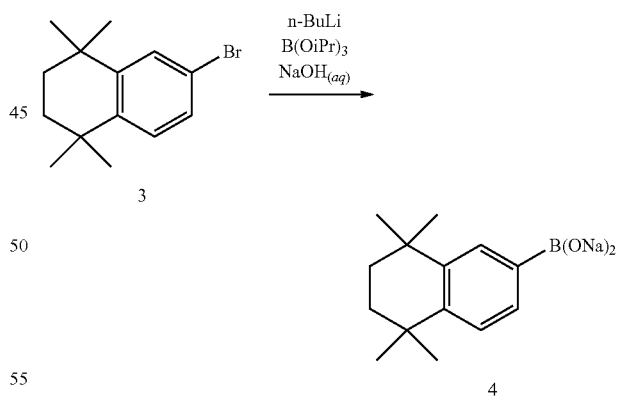

Procedure: purge the reactor with N₂. Charge the 2 L reactor with Bromide 3 (106.7 g) and THF (350 mL). Cool to −55° C. Exothermic. Hold temperature with addition rate (ca 50 min: clear solution). Add the BuLi soln (275 mL) holding <−50° C. (50 min). Stir 20-45 min. Insolubles form during aging as a thin slurry. While stirring the suspension add the isopropyl borate (116 mL) holding <−50° C. (50 min). Endothermic. Hold temperature with addition rate (ca 50 min). Stir 30 min. Warm to 15° C. over 1-2 h (overnight is acceptable). Charge 3N HCl (440 mL). 10° C. exotherm on charging. Insolubles dissolved to two clear layers. Stir 10 min. Drain aqueous (ca 750 mL) to a separatory funnel. Extract with MeTHF (350 mL) and combine organic layers. Stir to equilibrate. Drain residual aqueous. Transfer organic layer to rotovap and strip to dryness (bath 45° C., end vacuum 30 Torr); 145 g residue. Charge heptane (100 mL) and again strip to dryness; 125 g residue that solidifies on standing. Redissolve in 450 mL of heptane (in rotovap flask, bath 45° C.) and transfer back to the 2 L reactor (turbid solution). Add NaOH solution (prepared from 55 mL of 50% NaOH and 268 mL of water) at 45-55° C. over ca 20 min; solids precipitated. Cool to 40° C. and filter off the solids. 800 mL medium frit filter is used with a medium to slow filtration rate. The cake is washed with heptane before the surface is exposed to avoid the cake contracting from the walls; the cake is pressed with silicone sheet. Wet cake: 200 g. Wash the cake with heptane (3×100 mL). Dry weight: 105 g (95%). Vacuum dry 40-45° C. The heptane layer is stripped to dryness giving 17 g of an oil shown (GCMS) to be an 87:13 mixture of starting material where the Br was replaced with butyl and H (see GC/MS).

Example 20: Synthesis of Compound 8

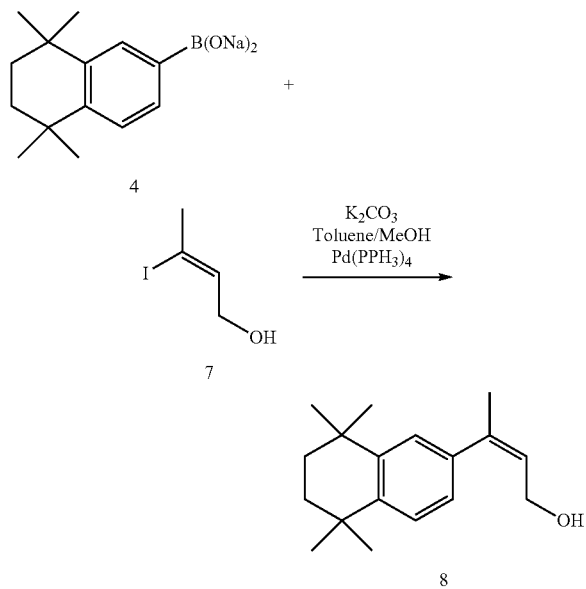

Procedure: purge the reactor with $N_2$. Charge the 2 L reactor with Boronate 4 (110 g), toluene (400 mL), MeOH (260 mL) and water (140 mL), Turn on the stirrer. Charge the $K_2CO_3$ (115 g). Sparge ($N_2$) for 10 min. Charge the iodide 7 (83 g). Sparge ($N_2$) for 15 min. Charge the catalyst (2.5 g) (the mixture is two liquid phases plus solids). Heat to 70-72° C. Stir 1 h and pull sample for IPC. Stir another 2 h. Cool to 20-25° C. Charge 200 mL of water and stir 5 min. Stop the stirrer and cut the aqueous layer. Extract the aqueous with 300 mL of toluene. Wash the combined organic layers with water (3×200 mL), then 2×50 mL of brine. Strip to dryness (turbidity-free yellow oil, which starts to crystallize on standing overnight). Charge 150 mL of heptane and strip to dryness to remove residual toluene. Take up in hot (60° C.) heptane and filter hot; product is very soluble hot. Filter off 1.4 g of dull orange powder. Seeds do not hold until 31° C. Product comes out as cotton-like fibers at 25° C. Continued stirring at ca 20° C. for 6-8 h changes the form of the fibrous appearance to a finer slurry (a powder-like suspension). Cool to 40° C. then cool slowly adding seeds every 2° C. Cool slowly to room temp and stir overnight. Cool to −10° C. Filter off the solids. Wash the cake with <−10° C. heptane. Vacuum dry 40-45° C. Final dry yield: 49 g (48%).

Example 21: Synthesis of Compound 9

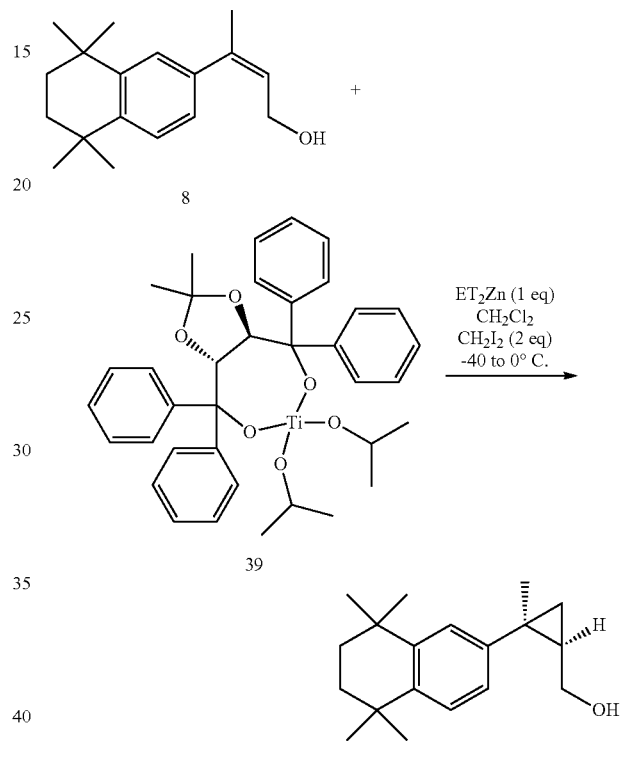

To a solution of $CH_2I_2$ (160 mL, 2 mmol) in $CH_2Cl_2$ (5 mL) is added dropwise $Et_2Zn$ (100 mL, 1 mmol). The resulting solution is stirred at 0° C. for 15 min and a white precipitate is formed. The solution is cooled to −40° C. and a solution of the TADDOL-Ti catalyst (Compound 39; prepared by mixing (4R,5R)-2,2-dimethyl-a,a,a',a'-Tetraphenyl-1,3-dioxolane-4,5-dimethanol (TADDOL) (140 mg, 0.29 mmol) (or its corresponding enantiomer) and 4 Å molecular sieves (1 g) in $CH_2Cl_2$ (5 mL) is added $Ti(Oi-Pr)_4$ (74 mL, 0.25 mmol). After 1.5 h of stirring at room temperature, the solvent is removed under reduced pressure and dried under high vacuum for 2 h. $CH_2Cl_2$ (5 mL) is added immediately followed by a solution of compound 1 (268 mg, 1.04 mmol) in $CH_2Cl_2$ (5 mL). After 90 min of stirring at 0° C., the resulting solution is cooled to −40° C. and poured into 30 mL of a saturated aqueous $NH_4Cl$. The layers is separated and the aqueous layer is washed with EtOAc (3×). The combined organic layers is washed with saturated aqueous $NH_4Cl$, saturated aqueous NaCl, dried over $MgSO_4$ and concentrated under reduced pressure. The residue is purified by flash chromatography (20% EtOAc/hexanes) to afford the desired product, Compound 9 is isolated.

Example 22: Synthesis of Compound 8

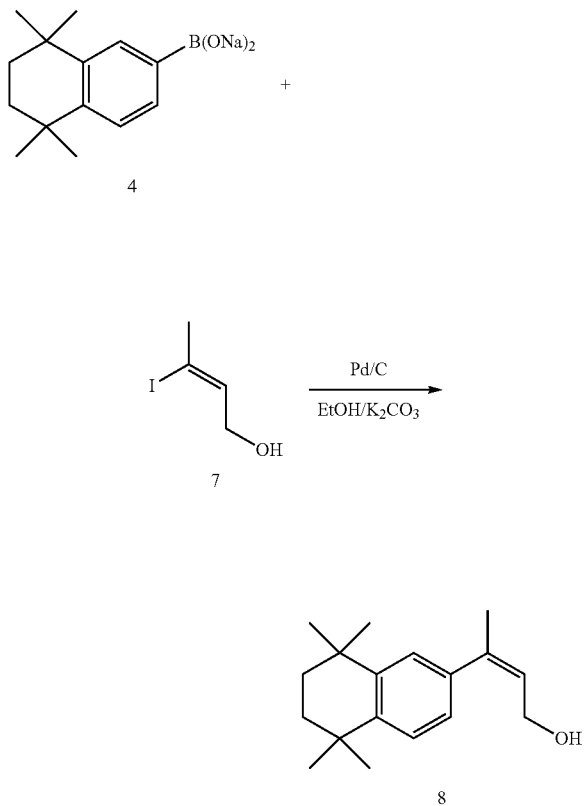

Into a nitrogen purged reactor charged with compound 4 (1.651 kg), 3-iodo-but-2-en (Z) of (compound 7) (1.408 Kg, 7.11 moles) and EtOH (14 L). While stirring this mixture, potassium carbonate (1.962 Kg, 14.22 moles), Pd—C (0.115 Kg) and water (0.75 Kg) were added to the reactor and the reaction was sparged with nitrogen gas for 5 min. The reaction was heated to 65-70° C. for 2 h. The reaction was continued until the boronate 4 was less than 1% of the reaction mixture. The reaction mixture was cooled to room temperature and was filtered through Solka Floc 40 (0.8 Kg). The cake was washed with EtOH (8 L), the combined organic layer solvent was removed on a rotavapor under reduced pressure. This crude product was charged with water (3.4 L), methyl t-butyl ether (MTBE) (0.8 L) and heptane (7.8 L). The mixture was heated to 45-55° C. and the layers were separated, and the organic layer was washed with water (2×2 L). The organic layer was filtered through Solka Floc 40. Solvent was distilled off from the filtrate to dryness. This crude product was taken up in heptane (4.4 L) at a temperature of 60° C. and the solution was cooled slowly to 40° C. adding seeds every 1° C. The slurry was stirred overnight at 30° C. Then the mixture was cooled between −10 and −12° C. for 30 min. and the solids were filtered off using Solka Floc 40 (coarse frit). The solid cake was washed with cold (0° C.) heptane and dried under vacuum between 40-45° C. The product (compound 8) was isolated as a white solid, 1.62 Kg (84% yield).

Example 23: Synthesis of Compound 9

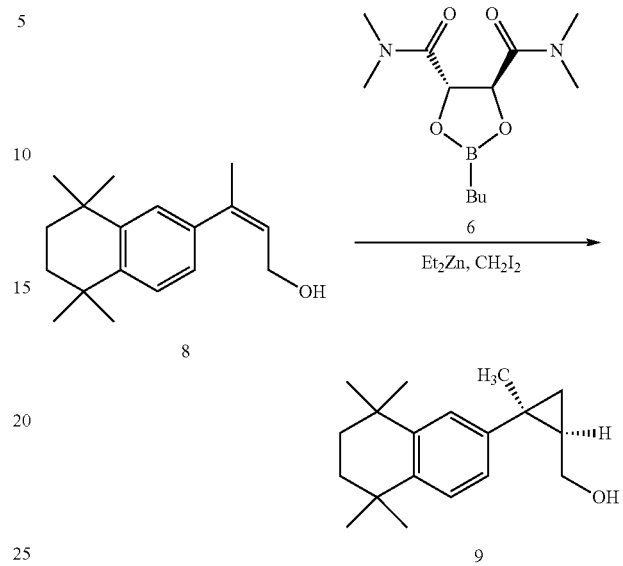

To a 50 L reactor equipped with an addition funnel, thermocouple and $N_2$ inlet, was charged $CH_2Cl_2$ (12.8 L), DME (2.76 L) and the resulting solution cooled to −25 to −15° C. with stirring. A solution of $ZnEt_2$ 15% in toluene, (17.8 L, 19.4 mol, 3.6 eq.) was added using an addition funnel in a steady stream holding <−15 C, followed by a toluene (70 mL rinse of the addition funnel). $CH_2I_2$ (3.25 L, 40.37 mol, 7.46 eq.) was added slowly, keeping the temperature at −15±5° C. during the addition (delayed exotherm). After stirring for 20-30 minutes at −15±5° C., the boronate catalyst (1.755 Kg, 6.5 mol, 1.2 eq) was charged as a solution in $CH_2Cl_2$ (200 mL) followed immediately by dropwise addition of alcohol 8 (1.4 Kg, 5.418 mol, 1.0 eq) in $CH_2Cl_2$ (2.1 L) over 35 minutes. After stirring at −15±5° C. the mixture was warmed to −5° C. for an overnight stir period.

A solution of 3M HCl (6 L) was carefully added and the mixture stirred vigorously until all solids had dissolved (15-30 minutes). The phases were separated and the DCM stripped off. The organic layer was washed with water, stirred with NaOH (aq) (7.6 L of 50% solution; 18.75 mol in water). At this point an oxidative work up was employed with 0.6 L 30% $H_2O_2$ added (Note; VERY exothermic reaction. Cooled and added slowly). After stirring for 15-30 minutes, the aqueous layer was cut, and the organic phase washed with 2.4 L of 10% $Na_2SO_3$ and half sat. brine (3 L). The mixture was then stripped to an oil, dissolved in 8 L of heptane and stripped (2×) to give a syrup (1.98 Kg, 130%), compound 9. This was recrystallized from methanol and ethylene glycol.

1) Dissolved the crude in 3 volumes of MeOH (filtered to remove turbidity).

2) Diluted with 7.6 volumes of ethylene glycol (EG, seeding).

3) Diluted slowly with 2 volumes of water (seeding).

4) Aged overnight.

5) Solids collected by filtration.

Recrystallized yield is 87.5%, with 98.3% ee.

Example 24: Synthesis of Compound 9

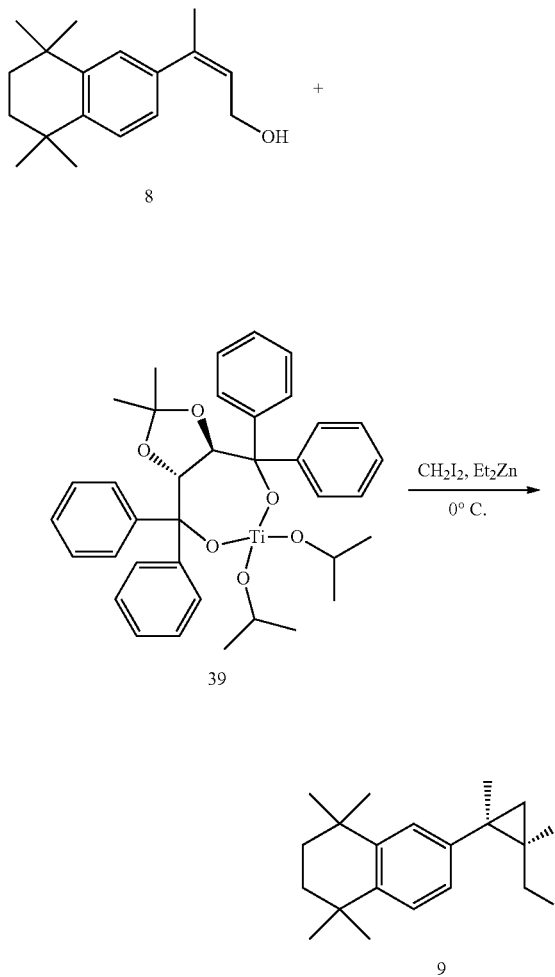

To a solution of $CH_2I_2$ (160 μL, 2 mmol) in $CH_2Cl_2$ (5 mL) is added dropwise $Et_2Zn$ (100 mL, 1 mmol). The resulting solution is stirred at 0° C. for 15 min and a white precipitate is formed. The solution is cooled to −40° C. and a solution of the TADDOL-Ti catalyst (Compound 39; prepared by mixing (4R,5R)-2,2-dimethyl-a,a,a',a'-Tetraphenyl-I,3-dioxolane-4,5dimethanol(TADDOL) (140 mg, 0.29 mmol) (or its corresponding enantiomer) and 4 Å molecular sieves (1 g) in $CH_2Cl_2$ (5 mL) is added Ti(Oi-Pr)$_4$ (74 mL, 0.25 mmol). After 1.5 h of stirring at room temperature, the solvent is removed under reduced pressure and dried under high vacuum for 2 h. $CH_2Cl_2$ (5 mL) is added immediately followed by a solution of compound 8 (268 mg, 1.04 mmol) in $CH_2Cl_2$ (5 mL). After 90 min of stirring at 0° C., the resulting solution is cooled to −40° C. and poured into 30 mL of a saturated aqueous $NH_4Cl$. The layers is separated and the aqueous layer is washed with EtOAc (3×). The combined organic layers is washed with saturated aqueous $NH_4Cl$, saturated aqueous NaCl, dried over $MgSO_4$ and concentrated under reduced pressure. The residue is purified by flash chromatography (20% EtOAc/hexanes) to afford the desired product, Compound 9 is isolated.

Example 25: Synthesis of Compound 9

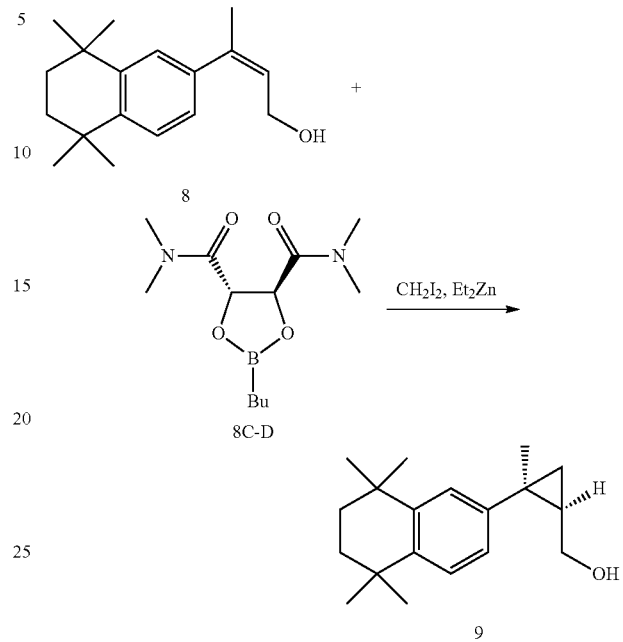

A 250 mL RBF was charged with $CH_2Cl_2$ (50 mL), DME (10 mL) and cooled in a cooling bath to 20±5° C. A solution of $ZnEt_2$ (70 mL, 1.0 M in heptane, 70 mmoles, 3.5 eq.) was added followed by $CH_2I_2$ (38.0 g, 142 mmoles, 7.1 eq) added to the flask neat, with a 2×2 mL $CH_2Cl_2$ rinse, over about 30 minutes. The resulting solution was stirred for an additional 20 minutes, and the chiral tartaramide catalyst, 8C-D, was dissolved in a $CH_2Cl_2$ and added to the flask, keeping the temperature at −15±3° C. A solution of allylic alcohol 8 (5.16 g, 20 mmoles, 1.0 eq.) in $CH_2Cl_2$ (20 mL) was then added over 15 minutes. Upon the end of the addition the cooling bath was removed and the reaction mixture allowed to slowly warm to ambient temperature for an overnight stir period. The next morning the mixture was analyzed by HPLC and approximately 2% of 8 was found in the mixture so the work up was commenced. A solution of HCl(aq), (3 M, 40 mL, 6 eq.) was added and the mixture allowed to stir until all solids had been dissolved. Agitation was stopped and the layers separated. The aqueous layer was back-extracted with $CH_2Cl_2$ (some product was detected in the aqueous phase) and the combined organic extracts washed with NaOH(aq) (20%, 30 mL), $Na_2SO_3$(aq) (30 mL, saturated), and then brine (2×15 mL). The resulting oil was taken up in warm heptane/2-MeTHF (80 mL/15 mL), the solids filtered off, and the solution concentrated to provide 6.0 g of light yellow oil (Yield: 112%; HPLC purity: 97.9%; Chiral purity: 88%, which equals 76% ee (enantiomeric excess)).

Example 26: Compound A Analysis

Compound 38 (e.g., Compound A), an off-white solid, as prepared herein was analyzed by LC/MS (ESI+), $^1$H-NMR (300 MHz/CDCl$_3$), and HPLC, (area %). Compound A had an enantiomeric purity of 99.9% (by HPLC area), with no detectable presence of Compound B(by HPLC area). The melting point (DSC) was also determined, which had an onset at 142.7° C., and a peak at 144.7° C.

Unless otherwise indicated, all numbers expressing quantities of ingredients, properties such as molecular weight, reaction conditions, and so forth used in the specification and claims are to be understood as being modified in all instances by the term "about," As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific Examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all embodiments, or exemplary language (e.g., "such as") provided herein is intended merely to better illuminate the subject-matter provided herein. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments iscome apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of embodiment, but not of limitation, alternative configurations of the present invention may be utilized in accordance with the teachings herein. Accordingly, the present invention is not limited to that precisely as shown and described.

Embodiments

Embodiment 1

A compound, wherein the compound is:

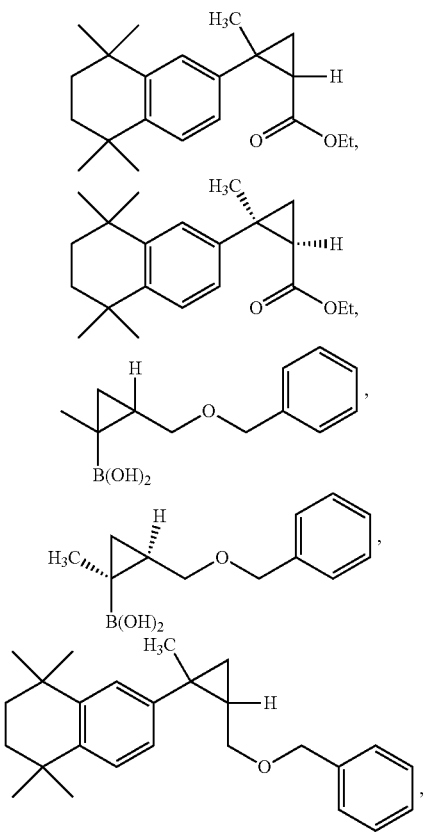

-continued

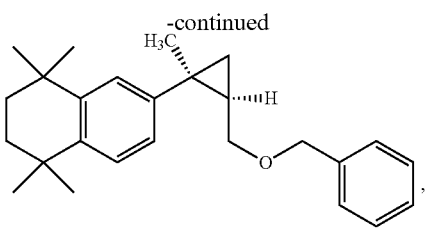

or a hydrate or a solvate thereof.

Embodiment 2

A process of preparing a compound of Formula IX

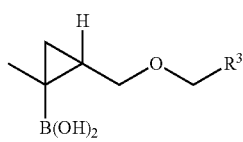
(IX)

or a solvate thereof
comprising:
contacting a compound of Formula VIII

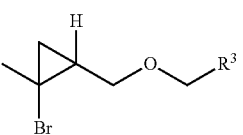
(VIII)

or a solvate thereof
with n-BuLi or t-BuLi, and B(OMe)$_3$
such that a compound of Formula IX or a solvate thereof is formed,
wherein R$^3$ is aryl, or aryl substituted with one or more substituents independently selected from —OH, halogen, —C$_{1-10}$-alkyl, —C$_{1-10}$-haloalkyl, or —O—(C$_{1-10}$-alkyl).

Embodiment 3

The process of embodiment 2, wherein R$^3$ is C$_{6-14}$-aryl, or C$_{6-14}$-aryl substituted with one or more substituents independently selected from —OH, halogen, —C$_{1-10}$-alkyl, —C$_{1-10}$-haloalkyl, —O(—C$_{1-10}$-alkyl), or —O—(C$_{1-10}$-haloalkyl).

Embodiment 4

The process of embodiment 2, wherein:
the compound of Formula IX is

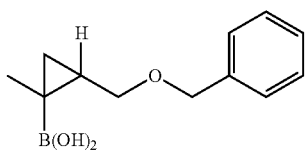 [SMILES: CC1(B(O)O)CC1COCc1ccccc1]

or a solvate thereof; and
the compound of Formula VIII is

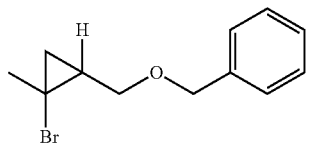

or a solvate thereof.

Embodiment 5

A process of preparing a compound of Formula X (X)

or a solvate thereof
comprising:
contacting a compound of Formula IX (IX)

or a solvate thereof
with Pd$_{(0)}$ and or a solvate thereof,
such that a compound of Formula X or a solvate thereof is formed,
wherein R$^3$ is aryl, or aryl substituted with one or more substituents independently selected from —OH, halogen, —C$_{1-10}$-alkyl, —C$_{1-10}$-haloalkyl, or —O—(C$_{1-10}$-alkyl).

Embodiment 6

The process of embodiment 5, wherein R$^3$ is C$_{6-14}$ aryl, or C$_{6-14}$-aryl substituted with one or more substituents independently selected from —OH, halogen, —C$_{1-10}$-alkyl, —C$_{1-10}$-haloalkyl, —O—(C$_{1-10}$-alkyl), or —O—(C$_{1-10}$-haloalkyl).

Embodiment 7

The process of embodiment 5, wherein:
the compound of Formula IX is

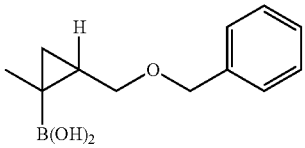 [SMILES: CC1(B(O)O)CC1COCc1ccccc1]

or a solvate thereof; and
the compound of Formula X is

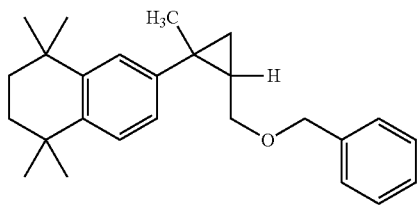 [SMILES: CC1(C)CCC(C)(C)c2cc(C3(C)CC3COCc3ccccc3)ccc21]

or a solvate thereof.

Embodiment 8

The process of embodiment 5, wherein:
the compound of Formula IX is

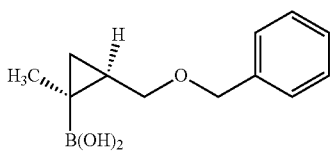 [SMILES: C[C@]1(B(O)O)C[C@H]1COCc1ccccc1]

or a solvate thereof; and
the compound of Formula X is

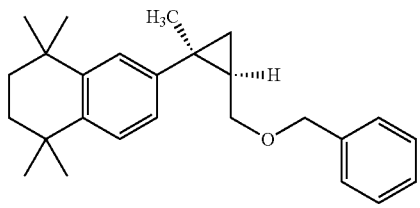 [SMILES: CC1(C)CCC(C)(C)c2cc([C@@]3(C)C[C@H]3COCc3ccccc3)ccc21]

or a solvate thereof.

Embodiment 9

A process of preparing ethyl 2-methyl-2-(5,5,8,8-tetramethyl-5,6,7,8-tetrahydronaphthalen-2-yl)cyclopropanecarboxylate

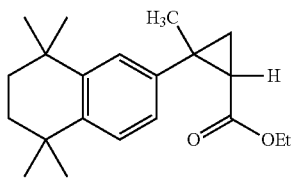 [SMILES: CCOC(=O)C1CC1(C)c1ccc2c(c1)C(C)(C)CCC2(C)C]

or a solvate thereof
comprising:
contacting 1,1,4,4-tetramethyl-6-(prop-1-en-2-yl)-1,2,3,4-tetrahydronaphthalene

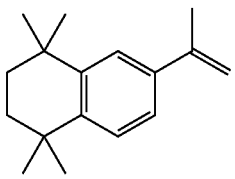 [SMILES: C=C(C)c1ccc2c(c1)C(C)(C)CCC2(C)C]

or a solvate thereof
with Rh(OAc)$_2$ and ethyl 2-diazoacetate or a solvate thereof,
such that ethyl 2-methyl-2-(5,5,8,8-tetramethyl-5,6,7,8-tetrahydronaphthalen-2-yl)cyclopropanecarboxylate or a solvate thereof is formed.

Embodiment 10

The process of embodiment 9, wherein the ethyl 2-methyl-2-(5,5,8,8-tetramethyl-5,6,7,8-tetrahydronaphthalen-2-yl)cyclopropanecarboxylate or a solvate thereof is

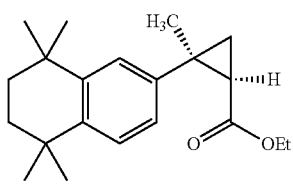

or a solvate thereof.

Embodiment 11

A process of preparing (2-methyl-2-(5,5,8,8-tetramethyl-5,6,7,8-tetrahydronaphthalen-2-yl)cyclopropyl)methanol

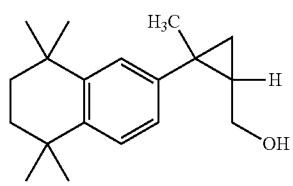 [SMILES: CC1(C)CCC(C)(C)c2cc(C3(C)CC3CO)ccc21]

or a solvate thereof
comprising:
contacting (Z)-3-(5,5,8,8-tetramethyl-5,6,7,8-tetrahydronaphthalen-2-yl)but-2-en-1-ol

75

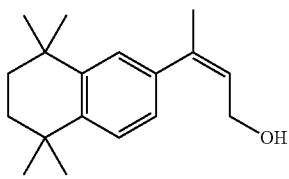 [SMILES: C/C(=C/CO)c1ccc2c(c1)C(C)(C)CCC2(C)C]

or a solvate thereof
with CH$_2$I$_2$, Et$_2$Zn, ZnI$_2$, and N,N'-(cyclohexane-1,2-diyl)dimethanesulfonamide

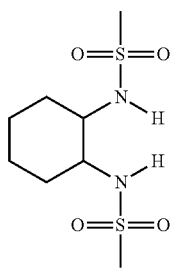 [SMILES: CS(=O)(=O)NC1CCCCC1NS(C)(=O)=O]

or a solvate thereof,
such that (2-methyl-2-(5,5,8,8-tetramethyl-5,6,7,8-tetrahydronaphthalen-2-yl)cyclopropyl)methanol or a solvate thereof is formed.

Embodiment 12

The process of embodiment 11, wherein:
the (2-methyl-2-(5,5,8,8-tetramethyl-5,6,7,8-tetrahydronaphthalen-2-yl)cyclopropyl)methanol or a solvate thereof is

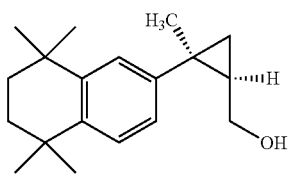 [SMILES: CC1(C)CCC(C)(C)c2cc([C@@]3(C)C[C@H]3CO)ccc21]

or a solvate thereof; and
the N,N'-(cyclohexane-1,2-diyl)dimethanesulfonamide or a solvate thereof is

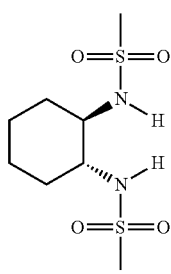 [SMILES: CS(=O)(=O)N[C@@H]1CCCC[C@H]1NS(C)(=O)=O]

or a solvate thereof.

76

Embodiment 13

A process of preparing a compound of Formula III

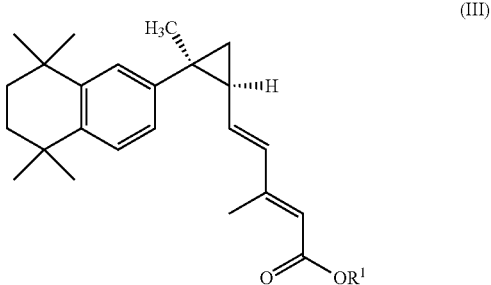

(III)

or a solvate thereof
comprising:
contacting (1R,2S)-2-methyl-2-(5,5,8,8-tetramethyl-5,6,7,8-tetrahydronaphthalen-2-yl)cyclopropanecarbaldehyde

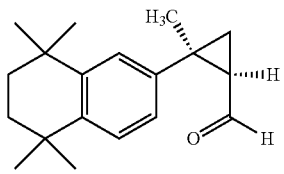 [SMILES: CC1(C)CCC(C)(C)c2cc([C@@]3(C)C[C@H]3C=O)ccc21]

or a hydrate or solvate thereof
with potassium t-butoxide and a compound of Formula

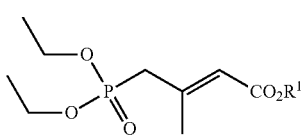

(I)

or a solvate thereof,
such that a compound of Formula III or a solvate thereof is formed,
wherein R$^1$ is C$_{1-20}$-alkyl; C$_{1-20}$-alkyl substituted with one or more substituents independently selected from —NH$_2$, —NH(C$_{1-10}$-alkyl), —N(C$_{1-10}$-alkyl)(C$_{1-10}$-alkyl), —OH, halogen, —C$_{1-10}$-alkyl, —C$_{1-10}$-haloalkyl, —O—(C$_{1-10}$-alkyl), or —O—(C$_{1-10}$-haloalkyl); C$_{1-20}$-alkenyl; C$_{1-20}$-alkenyl substituted with one or more substituents independently selected from —NH$_2$, —NH(C$_{1-10}$-alkyl), —N(C$_{1-10}$-alkyl)(C$_{1-10}$-alkyl), —OH, halogen, —C$_{1-10}$ alkyl, —C$_{1-10}$ haloalkyl, —O—(C$_{1-10}$-alkyl), or —O—(C$_{1-30}$-haloalkyl); C$_{6-14}$-aryl; or C$_{6-14}$-aryl substituted with one or more substituents independently selected from —NH$_2$, —NH(C$_{1-10}$-alkyl), —N(C$_{1-10}$-alkyl)(C$_{1-10}$-alkyl), —OH, halogen, —C$_{1-10}$-alkyl, —C$_{1-10}$-haloalkyl, —O—(C$_{1-10}$-alkyl), or —O—(C$_{1-10}$-haloalkyl).

Embodiment 14

The process of embodiment 13, wherein R$^1$ is C$_{1-20}$-alkenyl, or C$_{6-14}$-aryl.

Embodiment 15

The process of any one of embodiments 2-14, wherein the process is performed in a solvent or a combination of solvents.

Embodiment 16

The process of embodiment 15, wherein the solvent is a non-polar solvent or a polar non-aqueous solvent, an aqueous solvent, or a combination thereof.

Embodiment 17

A process of preparing a compound of Formula (XI):

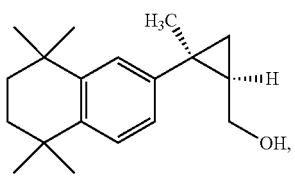

(XI)

or a solvate thereof,
comprising:
(i) contacting a compound of Formula (XII);

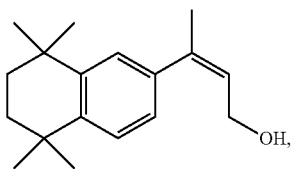

(XII)

or a solvate thereof,
with a compound of Formula (XIII);

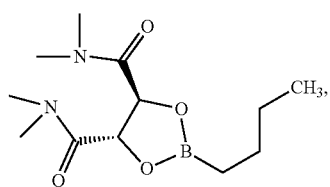

(XIII)

or a solvate thereof,
in a solution in the presence of $CH_2I_2$ and $Et_2Zn$; and
(ii) subsequently, contacting the solution of step (i) with $H_2O_2$, such that a compound of Formula (XI) or a solvate thereof is prepared, wherein the compound of Formula (XI) has an enantiomeric excess of at least 98%.

Embodiment 18

A process of preparing a compound of formula (XI):

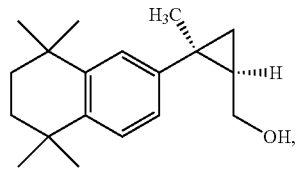

(XI)

or a solvate thereof,
comprising:
contacting a compound of Formula (XII);

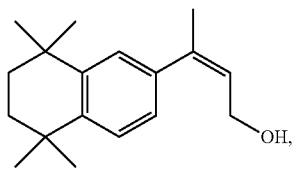

(XII)

or a solvate thereof,
with a compound of Formula (XIV) (or its enantiomer);

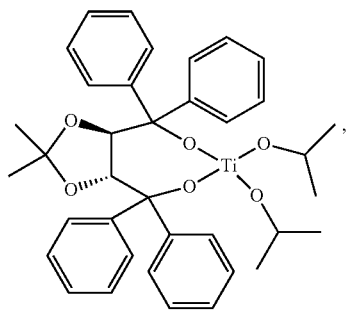

(XIV)

or a solvate thereof,
in the presence of $CH_2I_2$ and dialkylzinc such that a compound of Formula (XI) or a solvate thereof is prepared.

Embodiment 19

The process of embodiment 18, wherein the dialkylzinc is $ZnEt_2$.

Embodiment 20

A process of preparing a compound of Formula (XI):

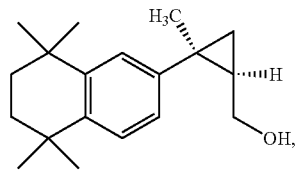

(XI)

or a solvate thereof, comprising:
contacting a compound of Formula (XII);

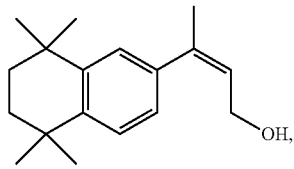
(XII)

or a solvate thereof,
with a compound of Formula (XV) or its enantiomer;

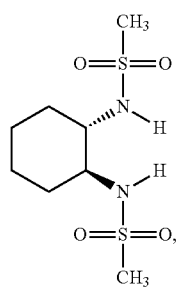
(XV)

or a solvate thereof,
in the presence of CH$_2$I$_2$ and Et$_2$Zn at about 0° C. such that the compound of Formula (XI) or a solvate thereof is prepared.

Embodiment 21

The process of embodiment 20, wherein the molar ratio of Formula (XII) to Formula (XV) is about 1.0:0.05 to about 1.0:0.3.

Embodiment 22

The process of embodiment 20, wherein the molar ratio of Formula (XII) to Formula (XV) is about 1.0:0.1.

Embodiment 23 A process of preparing a compound of Formula (XII):

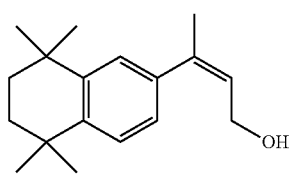
(XII)

or a solvate thereof, comprising:
contacting a compound of Formula (XVI);

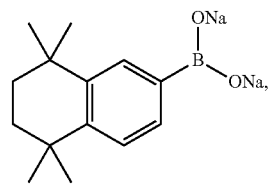
(XVI)

or a solvate thereof,
with a compound of Formula (XVII);

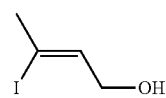
(XVII)

or a solvate thereof,
in the presence of Pd/C and a base, such that the compound of Formula (XII) or a solvate thereof is prepared.

Embodiment 24

The process of embodiment 23, wherein the base is K$_2$CO$_3$.

Embodiment 25

A process of preparing a compound of Formula (XVII):

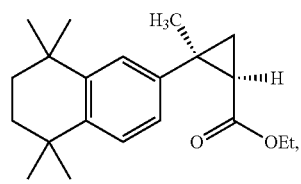
(XVII)

or a solvate thereof,
comprising:
contacting a compound of Formula (XVIII);

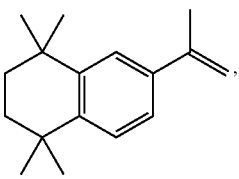
(XVIII)

or a solvate thereof, with a compound of Formula (XIX);

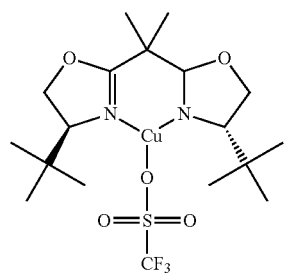
(XIX)

or a solvate thereof,
in the presence of N₂CH₂CO₂Et such that a compound of Formula (XVII) or a solvate thereof is prepared.

Embodiment 26

The process of embodiment 18 or embodiment 20, wherein the compound of Formula (XI) has an enantiomeric excess of at least about 98%.

Embodiment 27

The process of embodiment 25, wherein the compound of Formula (XVII) has an enantiomeric excess of at least about 98%.

Embodiment 28

A compound of Formula (XI):

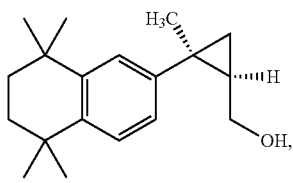
(XI)

or a hydrate or a solvate thereof,
wherein the compound of Formula (XI) has an enantiomeric excess of at least about 80.0%.

Embodiment 29

The compound of embodiment 28, wherein the compound of Formula (XI) has an enantiomeric excess of at least about 98%.

Embodiment 30

The compound of embodiment 28, wherein the compound is prepared by the process of embodiments 11, 12, 17, 18, or 20.

Embodiment 31

A composition comprising the compound of embodiment 28.

Embodiment 32

A compound of Formula (XVII):

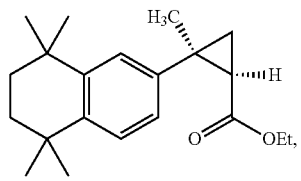
(XVII)

or a hydrate or a solvate thereof,
wherein the compound of Formula (XVII) has an enantiomeric excess of at least about 80.0%.

Embodiment 33

The compound of embodiment 32, wherein the compound of Formula (XVII) has an enantiomeric excess of at least about 98%.

Embodiment 34

The compound of embodiment 32, wherein the compound is prepared by the process of embodiments 9, 10, or 25.

Embodiment 35

A composition comprising the compound of embodiment 32.

What is claimed is:
1. A method of making Compound 38,

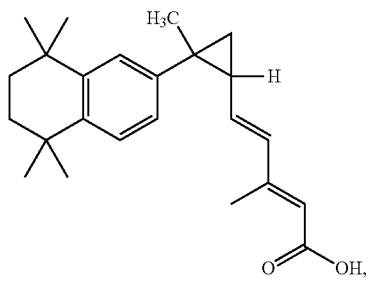
Compound 38 or a pharmaceutically acceptable salt thereof,
wherein:
Compound 38 has an enantiomeric excess of Compound A,

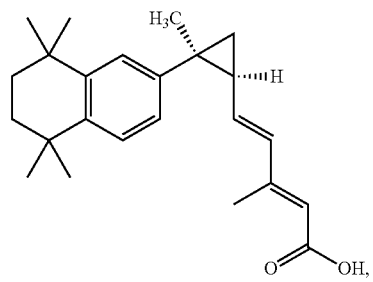
Compound A of least about 98.0%;

comprising a synthetic process of preparing an intermediate compound, wherein the intermediate compound is Formula (XIa),

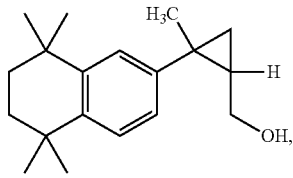
(XIa)

or a hydrate or a solvate thereof,
wherein the intermediate compound has an enantiomeric excess of a compound of Formula (XI),

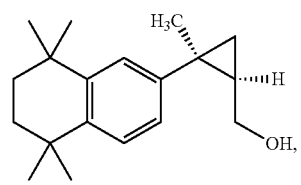
(XI)

or a hydrate or a solvate thereof,
of at least about 80.0%; wherein the process of preparing the intermediate compound, comprises contacting a compound of Formula (XII),

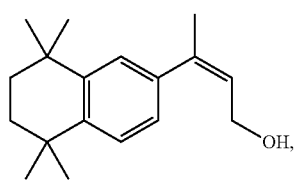
(XII)

or a solvate thereof, with:
a) $CH_2I_2$, $Et_2Zn$, $ZnI_2$, and an enantioselectivity inducer of Formula (XV) or its enantiomer,

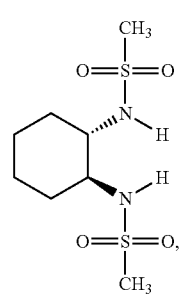
(XV)

or a solvate thereof, such that the intermediate compound is prepared; or
b) (i) an enantioselectivity inducer of Formula (XIII),

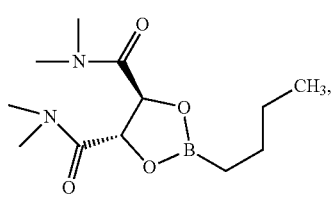
(XIII)

or a solvate thereof,
in a solution in the presence of $CH_2I_2$ and $Et_2Zn$ to form a reaction product of the compound of Formula (XII), or a solvate thereof; and
(ii) subsequently, contacting the solution of step (i) with $H_2O_2$, such that the compound of Formula (XI) or a solvate thereof is prepared; or
c) an enantioselectivity inducer of Formula (XIV) or its enantiomer,

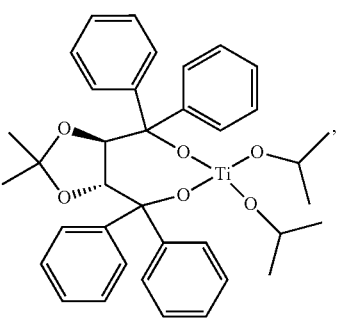
(XIV)

or a solvate thereof,
in the presence of $CH_2I_2$ and dialkylzinc such that the intermediate compound is prepared,
wherein the entire method of making Compound 38 comprises only a single synthetic step to produce the compound of Formula (XI).

2. The method of claim 1, wherein the process of preparing the intermediate compound, comprises:
contacting a compound of Formula (XII),

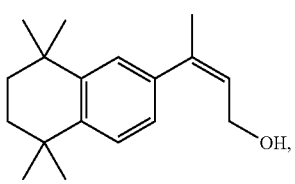
(XII)

or a solvate thereof,
with $CH_2I_2$, $Et_2Zn$, $ZnI_2$, and the enantioselectivity inducer of Formula (XV) or its enantiomer, (XV)

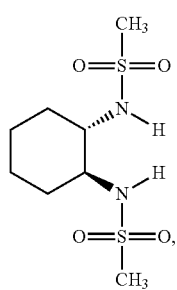

or a solvate thereof,
such that the intermediate compound is prepared.

3. The method of claim 2, wherein the enantioselectivity inducer or a solvate thereof, is (XV)

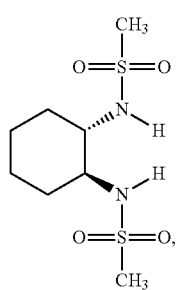

or a solvate thereof.

4. The method of claim 1, wherein the process of preparing the intermediate compound, comprises:
(i) contacting a compound of Formula (XII), (XII)

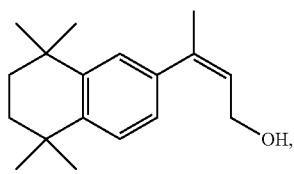

or a solvate thereof,
with the enantioselectivity inducer of Formula (XIII), (XIII)

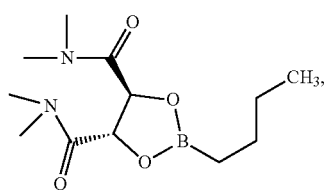

or a solvate thereof,
in a solution in the presence of $CH_2I_2$ and $Et_2Zn$ to form a reaction product of the compound of Formula (XII), or a solvate thereof; and
(ii) subsequently, contacting the solution of step (i) with $H_2O_2$, such that the compound of Formula (XI) or a solvate thereof is prepared.

5. The method of claim 1, wherein the process of preparing the intermediate compound, comprises:
contacting a compound of Formula (XII), (XII)

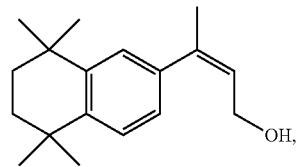

or a solvate thereof,
with the enantioselectivity inducer of Formula (XIV) or its enantiomer, (XIV)

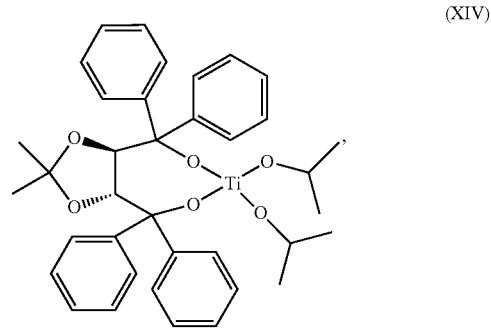

or a solvate thereof,
in the presence of $CH_2I_2$ and dialkylzinc such that the intermediate compound is prepared.

6. The method of claim 2, wherein the $ZnI_2$ is formed by reacting $Et_2Zn$ with $I_2$.

7. A method of synthesizing and working-up a compound of, Formula (XI), (XI)

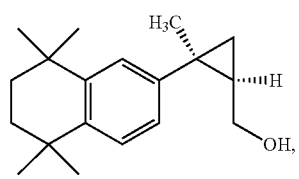

or a hydrate or a solvate thereof,
having an enantiomeric excess of at least about 85% over its enantiomer wherein the of Formula (XI) compound is prepared by a process comprising:
contacting a compound of Formula (XII), (XII)

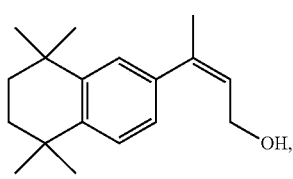

or a solvate thereof, a) CH$_2$I$_2$, Et$_2$Zn, ZnI$_2$, and an enantioselectivity inducer of Formula (XV) or its enantiomer,

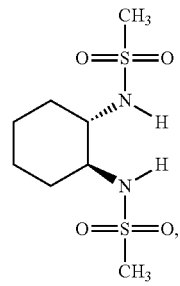
(XV)

or a solvate thereof,
such that the compound of Formula (XI) is prepared; or
b) (i) an enantioselectivity inducer of Formula (XIII),

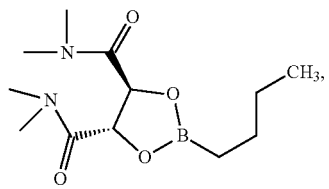
(XIII)

or a solvate thereof,
in a solution in the presence of CH$_2$I$_2$ and Et$_2$Zn to form a reaction product of the compound of Formula (XII), or a solvate thereof; and
(ii) subsequently, contacting the solution of step (i) with H$_2$O$_2$, such that the compound of Formula (XI) or a solvate thereof is prepared; or
c) an enantioselectivity inducer of Formula (XIV) or its enantiomer,

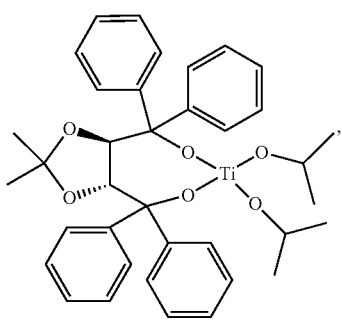
(XIV)

or a solvate thereof,
in the presence of CH$_2$I$_2$ and dialkylzinc such that the compound of Formula (XI) is prepared,
wherein the synthesis and work-up comprise a single synthetic step.

8. The method of claim 7, wherein the compound is present in an enantiomeric excess is at least about 98.0% over its enantiomer.

9. The method of claim 7, wherein the compound is synthesized and worked-up by a process comprising:

contacting a compound of Formula (XII),

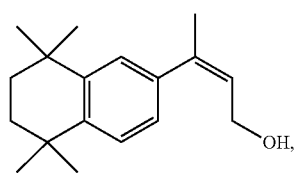
(XII)

or a solvate thereof,
with CH$_2$I$_2$, Et$_2$Zn, ZnI$_2$, and the enantioselectivity inducer of Formula (XV) or its enantiomer,

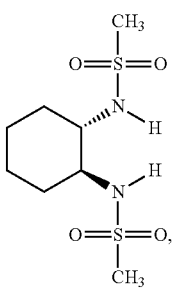
(XV)

or a solvate thereof,
such that the compound is prepared.

10. The method of claim 9, wherein the enantioselectivity inducer is

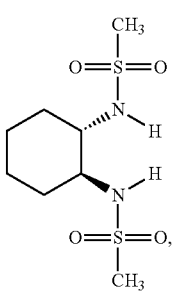
(XV)

or a solvate thereof.

11. The method of claim 7, wherein the compound is synthesized and worked-up by a process comprising:
(i) contacting a compound of Formula (XII),

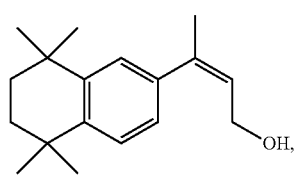
(XII)

or a solvate thereof, with the enantioselectivity inducer of Formula (XIII),

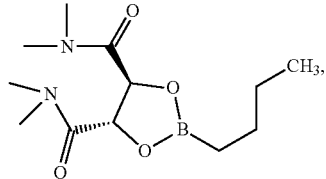
(XIII)

or a solvate thereof,
in a solution in the presence of $CH_2I_2$ and $Et_2Zn$ to form a reaction product of the compound of Formula (XII), or a solvate thereof; and
(ii) subsequently, contacting the solution of step (i) with $H_2O_2$, such that the compound of Formula (XI) or a solvate thereof is prepared.

12. The method of claim 7, wherein the compound is synthesized and worked-up by a process comprising:
contacting a compound of Formula (XII),

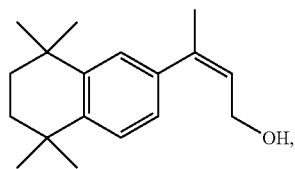
(XII)

or a solvate thereof,
with the enantioselectivity inducer of Formula (XIV) or its enantiomer,

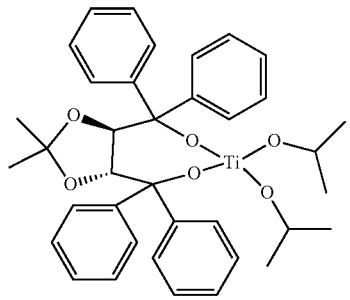
(XIV)

or a solvate thereof,
in the presence of $CH_2I_2$ and dialkylzinc such that the compound of claim 7 is prepared.

13. The method of claim 9, wherein the $ZnI_2$ is formed by reacting $Et_2Zn$ with $I_2$.

14. The method of claim 1, further comprising purification of the compound of Formula (XI), wherein said purification comprises recrystallization.

15. The method of claim 4, further comprising purification of the compound of Formula (XI), wherein said purification consists of solvent stripping, filtration, extraction, distillation, evaporation, recrystallization, or combinations thereof.

16. The method of claim 7, wherein said working-up comprises purification of the compound of Formula (XI), wherein said purification comprises recrystallization.

17. The method of claim 11, wherein said working-up comprises purification of the compound of Formula (XI), wherein said purification consists of solvent stripping, filtration, extraction, distillation, evaporation, recrystallization, or combinations thereof.

* * * * *